US012612649B2

(12) United States Patent
Bendezu et al.

(10) Patent No.: US 12,612,649 B2
(45) Date of Patent: Apr. 28, 2026

(54) SELECTION MARKER FREE METHODS FOR MODIFYING THE GENOME OF BACILLUS AND COMPOSITIONS THEREOF

(71) Applicant: DANISCO US INC., Palo Alto, CA (US)

(72) Inventors: Felipe Oseas Bendezu, Chadds Ford, PA (US); Stacey Irene Robida Stubbs, Woolwich Township, NJ (US)

(73) Assignee: DANISCO US INC., Palo Alto, CA (US)

( * ) Notice: Subject to any disclaimer, the term of this patent is extended or adjusted under 35 U.S.C. 154(b) by 983 days.

(21) Appl. No.: 17/775,490

(22) PCT Filed: Nov. 18, 2020

(86) PCT No.: PCT/US2020/060988
§ 371 (c)(1),
(2) Date: May 9, 2022

(87) PCT Pub. No.: WO2021/101950
PCT Pub. Date: May 27, 2021

(65) Prior Publication Data
US 2022/0389459 A1     Dec. 8, 2022

Related U.S. Application Data

(60) Provisional application No. 62/937,372, filed on Nov. 19, 2019.

(51) Int. Cl.
*C12N 15/90* (2006.01)

(52) U.S. Cl.
CPC ...... *C12N 15/902* (2013.01); *C12N 2800/101* (2013.01); *C12N 2800/24* (2013.01)

(58) Field of Classification Search
None
See application file for complete search history.

(56) References Cited

U.S. PATENT DOCUMENTS

2022/0177923 A1* 6/2022 Frisch ................... C12N 15/11

FOREIGN PATENT DOCUMENTS

WO     0214490 A2     2/2002

OTHER PUBLICATIONS

Price et al., CRISPR-Cas9 In Situ engineering of subtilisin E in *Bacillus subtilis*. PLoS ONE (2019), 14(1): e0210121, and supplemental tables; published Jan. 7, 2019 (Year: 2019).*
*Bacillus subtilis* subsp. subtilis str. 168 complete genome, Accession NC_000964, https://www.ncbi.nlm.nih.gov/nuccore/255767013, available at least as early as Sep. 18, 2018 [retrieved Jan. 31, 2025]—includes amyE locus (Year: 2018).*
*Bacillus subtilis* subsp. subtilis str. 168 complete genome, Accession NC_000964, https://www.ncbi.nlm.nih.gov/nuccore/255767013, available at least as early as Sep. 18, 2018 [retrieved Jan. 31, 2025]—includes aprE locus (Year: 2018).*
Rahmer et al., Construction of a Super-Competent *Bacillus subtilis* 168 Using the PmtIA-comKS Inducible Cassette. Frontiers in Microbiology (2015), 6: 1431, pp. 1-11 (Year: 2015).*
Dong et al., Current development in genetic engineering strategies of Bacillus species. Microbial Cell Factories (2014), 13:63, pp. 1-11 (Year: 2014).*
Wu et al., Fast genome editing in *Bacillus subtilis*. Eng. Life Sci. (2019), 19: 471-477 (Year: 2019).*
Altenbuchner, "Editing of the *Bacillus subtilis* Genome by the CRISPR-Cas9 System", Applied and Environmental Microbiology, vol. 82, No. 17, Sep. 2016, pp. 5421-5427.
Davis et al, "Homology-directed repair of DNA nicks via pathways distinct from canonical double-strand break repair", Proc Natl Acad Sci USA, vol. 111, No. 10, Mar. 11, 2014 (Mar. 11, 2014), pp. E924-E932.
Dubnau, "Genetic Competence in *Bacillus subtilis*", Microbiological Reviews, vol. 55, No. 3, Sep. 1991, pp. 395-424.
Ferrari et al, "Isolation of an Alanine Racemase Gene from *Bacillus subtilis* and its Use for Plasmid Maintenance in *B. subtilis*", Nature Biotechnology, vol. 3, 1985, pp. 1003-1007.
Hamoen et al, "Controlling competence in *Bacillus subtilis*: shared use of regulators", Microbiology, vol. 149, 2003, pp. 9-17.
Hsu et al, "Development and Applications of CRISPR-Cas9 for Genome Engineering", Cell, vol. 157, Jun. 5, 2014 (Jun. 5, 2014), pp. 1262-1278.
Jarmer et al, "Transcriptome analysis documents induced competence of *Bacillus subtilis* during nitrogen limiting conditions", FEMS Microbiology Letters, vol. 206, 2002, pp. 197-200.
Lovett et al, "Crossing Over Between Regions of Limited Homology in *Escherichia coli*: RecA-Dependent and RecA-Independent Pathways", Genetics, vol. 160, Mar. 2002, pp. 851-859.

(Continued)

*Primary Examiner* — Catherine Konopka

(57) ABSTRACT

Methods and compositions are provided for modifying the genome of *Bacillus* sp. cells without the use of a selectable marker and without the use of a guided Cas endonuclease. The disclosure includes methods for integrating donor DNA sequences into the genome of a *Bacillus* sp. cell without the use of a selectable marker and without the use of Cas endonucleases into said genome, as well as methods for deleting genes of interest and/or providing point mutations into the genome of *Bacillus* sp. cells.

17 Claims, 1 Drawing Sheet

Specification includes a Sequence Listing.

(56)                    References Cited

OTHER PUBLICATIONS

Makarova et al, "An updated evolutionary classification of CRISPR-Cas systems", Nature Reviews Microbiology, vol. 13, Nov. 2015, pp. 722-736.

Papadopoulou et al, "Parameters controlling the rate of gene targeting frequency in the protozoan parasite Leishmania", Nucleic Acids Research, vol. 25, No. 21, 1997, pp. 4278-4286.

So et al, "A Highly Efficient CRISPR-Cas9-Mediated Large Genomic Deletion in *Bacillus subtilis*", Frontiers in Microbiology, vol. 8, Article 1167, Jun. 2017, pp. 1-12.

Zhang et al, "Multigene disruption in undomesticated *Bacillus subtilis* ATCC 6051a using the CRISPR/Cas9 system", Scientific Reports, vol. 6, Article 27943, Jun. 2016, pp. 1-11.

International Search Report from PCT App. No. PCT/US2020/060988 dated Feb. 17, 2021, 5 pages.

Written Opinion from PCT App. No. PCT/US2020/060988 dated Feb. 17, 2021, 4 pages.

International Preliminary Report on Patentability from PCT App. No. PCT/US2020/060988 dated May 17, 2022, 5 pages.

* cited by examiner

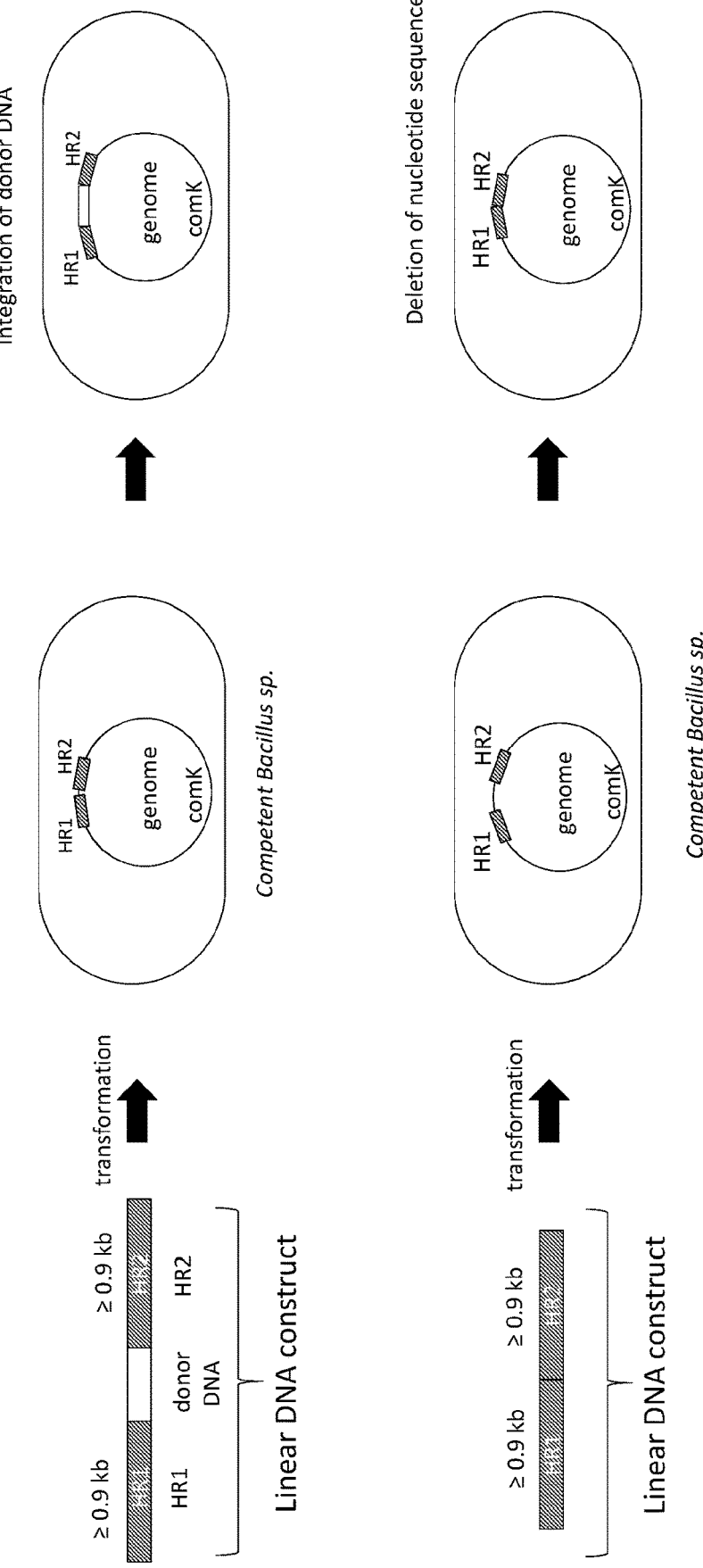

1

SELECTION MARKER FREE METHODS FOR MODIFYING THE GENOME OF BACILLUS AND COMPOSITIONS THEREOF

CROSS REFERENCE TO RELATED APPLICATIONS

The present application is a U.S. National Stage Application under 35 U.S.C. § 371 of International Application No. PCT/US2020/060988, filed Nov. 18, 2020, which claims priority to U.S. Provisional Patent Application No. 62/937,372, filed Nov. 19, 2019, all of which are incorporated herein by reference in their entirety.

FIELD OF INVENTION

The invention relates to the field of bacterial molecular biology, in particular, to compositions and methods for modifying the genome of *Bacillus* sp. cells without the use of a selectable marker and without the use of Cas endonucleases.

REFERENCE TO SEQUENCE LISTING SUBMITTED ELECTRONICALLY

The official copy of the sequence listing is submitted electronically via EFS-Web as an ASCII formatted sequence listing with a file named NB41425-WO-PCT_SequenceListing.txt created on Nov. 2, 2020, and having a size of 188 kilobytes and is filed concurrently with the specification. The sequence listing contained in this ASCII-formatted document is part of the specification and is herein incorporated by reference in its entirety.

BACKGROUND

Commercial production of enzymes in *Bacillus* species (*Bacillus* sp.) require methods for the construction of antibiotic resistance marker-free strains. These methods should fit several criteria; (i) be useful for both insertion of the gene of interest and for host modification, (ii) fast and efficient, and (iii) easy to use.

A widely used known method for altering the chromosome of *Bacillus* sp. involves building plasmid constructs and transforming them into *Escherichia coli* (*E. coli*). Subsequently, the plasmids are isolated from *E. coli* and transformed into *Bacillus* sp. using selectable markers. Widespread use of this method can be attributed, at least in part, to the notion that *E. coli* is easier to transform than *Bacillus*. In this regard, the in-vitro ligation of plasmids results in nicked products that can transform *E. coli* but do not transform *Bacillus*. The conventional approach to introduce donor DNA in *Bacillus* sp. is based on replicating plasmids. Such an approach, unfortunately, is generally associated with a number of disadvantages, including the need for an antibiotic or other selectable marker to maintain the plasmid in the cells. This is not desirable for production strains and it constrains the choice of screening conditions. Another disadvantage for using replicating plasmids is that genes on the plasmid are often present in multiple copies, affects gene regulation and expression.

Alternatively, integrating plasmids or vectors may be used. Integrating vectors do not contain an origin of replication and therefore require insertion into the host chromosome to be stably maintained. However, these are not without problems. Integration occurs via a Campbell-type recombination event that results in a duplication of the cloned region at either end of the inserted (now linear) vector. Depending on the position of the integration genes may be disrupted resulting in poor transformation efficiency.

Non-antibiotic selection cassettes can currently be used to construct ARM-free strains (Ferrari et al. 1985, Nat. Biotechnol. Vol. 3:1003-1007). This however is time consuming and the cassette needs to be removed to be useful in the same strain.

Previous methods for gene modification and gene integration into the genome of *Bacillus* sp. cells relied on spontaneous double strand break occurrence and use of selectable markers co-located on linear DNA fragments with short homology arms (comprising both the gene of interest (GOI) to be inserted into the genome as well as a selectable marker that was also inserted into the genome to enable identification of *Bacillus* sp. cells that had the gene of interest integrated into its genome (WO02/14490, published on Feb. 21, 2002). The selectable marker and GOI were typically flanked by two short homology arms such that upon recombination with the DNA within the cell both the GOI and the selectable marker would be integrated in the DNA of the cell. The use of selectable markers during transformation of such linear fragments with short homology arms for genome integration into *Bacillus* sp. cells is required to select for efficient modification of a specific locus of the genome. The selectable marker must integrate into the correct locus for expression and this integration relies on rare, spontaneous DNA damage that occurs in a stochastic manner within the population and within the genome. This rare event can only be selected for by combining the use of a marker and chromosomal integration. (WO02/14490, published on Feb. 21, 2002).

In *Bacillus subtilis,* use of a single plasmid system in combination with Cas endonuclease/RNA guided system has been described for allowing gene deletions and introduction of point mutations in genes (Altenbuchner J., 2016, Applied and Environmental Microbiology, vol.82 (17) pg. 5421-5427). Although Cas-based genome engineering techniques have been applied to a number of different host cell types, these techniques have known limitations. A CRISPR/Cas9 method has been used to construct ARM-free markerless strains (So et al. 2017, Front Microbiol, Vol. 8:1167, Zhang et al. 2016, Sci Rep, Vol. 6:27943). This approach requires access to Cas9 technology, construction of plasmids or linear fragments encoding Cas9 and a guide RNA for every site on the genome to be modified. It also requires removal of Cas9 at the end of the procedure. Although an improvement of previous methods the Cas9-based method still has many steps involved.

Thus, there remains a need for developing effective, efficient or otherwise more robust methods for genome modification, as well as gene integration of donor DNA sequences (such as but not limiting to a polynucleotide of interest, a single copy gene expression cassette or multi-copy gene expression cassette) into the genome of a *Bacillus* sp. cells without the use of selectable markers and/or Cas endonucleases.

BRIEF SUMMARY

The present disclosure includes methods and compositions for modifying the genome of *Bacillus* sp. cells without the use of a selectable marker and without the use of a guided Cas endonuclease system. The disclosure includes methods for integrating donor DNA sequences into the genome of a *Bacillus* sp. cell without the use of a selectable marker and without the use of a Cas endonuclease into said genome, as well as methods for deleting genes of interest and/or providing mutations into the genome of *Bacillus* sp. cells.

Without wishing to be bound by any particular theory, mechanism, or mode of action, Applicant has surprisingly and unexpectedly discovered that when a linear DNA construct comprising at its extremities long homology arms (each homology arm having at least 900 nucleotides) is introduced into competent *Bacillus* sp. cells, a high efficiency in genome modification (such as but not limited to donor DNA sequence integration, nucleotide deletions, mutations) is observed, wherein the introduction and genome modification occurs without the use of a selectable marker or a guided Cas endonuclease system.

The methods employ introducing linear DNA constructs into competent *Bacillus* sp. cells, wherein said linear DNA constructs are flanked by homology arms of at least 900 bps, optionally comprising a donor DNA flanked by said homology arms, wherein said DNA construct does not comprise a DNA fragment encoding for an endonuclease and wherein said DNA construct does not comprise a DNA sequence encoding for a selectable marker.

In one embodiment, the method is a method for integrating a donor DNA into the genome of a *Bacillus* sp. cell without the use of a selectable marker, the method comprising providing a population of competent *Bacillus* sp. cells and introducing a linear DNA construct into at least one *Bacillus* sp. cell of said population of cells, wherein said DNA construct comprises a donor DNA flanked by an upstream homology arm (HR1) and a downstream homology arm (HR2), wherein each homology arm is at least 900 nucleotides in length, wherein said DNA construct does not comprise a selectable marker, and optionally further comprising growing progeny cells from said at least one *Bacillus* sp. cell on media that do not comprise a selectable marker, and identifying a *Bacillus* sp. progeny cell that has the donor DNA sequence stably integrated in its genome.

In one embodiment, the method is a method for deleting a nucleotide sequence in the genome of a *Bacillus* sp. cell without the use of a selectable marker, the method comprising providing a population of competent *Bacillus* sp. cells, and introducing a linear DNA construct into at least one *Bacillus* sp. cell of said population of cells, wherein said DNA construct comprises an upstream homology arm (HR1) and a downstream homology arm (HR2), wherein each homology arm is at least 900 nucleotides in length and has sequence homology to a genomic DNA region flanking said nucleotide sequence to be deleted, wherein said DNA construct does not comprise a selectable marker.

In some embodiments each homology arm is at least 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 5000, 6000 nucleotides and up to 7000 nucleotides in length.

The linear DNA construct as described herein can be a double strand DNA.

In one embodiment, the competent *Bacillus* sp. cell is a *Bacillus* sp. cell selected from the group consisting of *Bacillus subtilis, Bacillus licheniformis, Bacillus lentus, Bacillus brevis, Bacillus stearothermophilus, Bacillus alkalophilus, Bacillus amyloliquefaciens, Bacillus clausii, Bacillus. halodurans, Bacillus. megaterium, Bacillus coagulans, Bacillus circulans, Bacillus lautus,* and *Bacillus thuringiensis.*

In one embodiment, the competent *Bacillus* sp. cells were made competent by at least one copy of an introduced nucleic acid construct comprising a promoter operably linked to a polynucleotide encoding a polypeptide selected from the group consisting of ComK, ComS or any one combination thereof.

In one embodiment, the competent *Bacillus* sp. cells are from a super-competent *Bacillus* sp. strain, such as but not limited to a Pxyl-ComK strain.

In one embodiment, the method is a method for introducing a mutation into the genome of a *Bacillus* sp. cell without the use of a selectable marker, the method comprising providing a population of competent *Bacillus* sp. cells and introducing a linear DNA construct into at least one *Bacillus* sp. cell of said population of cells, wherein said DNA construct comprises a nucleotide sequence having the desired mutation flanked by an upstream homology arm (HR1) and a downstream homology arm (HR2), and wherein each homology arm is at least 900 nucleotides in length, wherein said DNA construct does not comprise a selectable marker.

BRIEF DESCRIPTION OF THE DRAWINGS AND SEQUENCES

FIG. 1 depicts methods for modifying a genome of a *Bacillus* sp. cell using a linear DNA construct comprising at its extremities long homology arms (HR1 and HR2, each homology arm having at least 900 nucleotides (≥0.9 kb)) is introduced into competent *Bacillus* sp. cells. In the top illustration (FIG. 1), the linear DNA construct comprises a donor DNA flanked by two homology arms (one 5' upstream arm, HR1, and one 3' downstream arm HR2) at least 900 nucleotides in length. The donor DNA can comprise an expression cassette expressing a gene of interest. Once the donor construct is introduced into the cell, homologous recombination can occur which integrates the donor DNA into the genomic locus of interest. In the bottom illustration (FIG. 1), the linear DNA construct comprises two homology arms (one 5' upstream arm, HR1, and one 3' downstream arm HR2) of at least 900 nucleotides in length with no additional DNA in between the HR arms. Once this linear DNA construct is introduced into the cell, homologous recombination can occur which can result in a nucleotide deletion (gene deletion). The linear DNA constructs can be introduced into the *Bacillus* sp. cell by any mechanism know to one skilled in the art.

DETAILED DESCRIPTION

The present disclosure includes methods and compositions for modifying the genome of *Bacillus* sp. cells without the use of a selectable marker and without the use of a guide RNA/Cas endonuclease system. The present disclosure includes methods and compositions for integrating donor DNA sequences into the genome of a competent *Bacillus* sp. cell without the integration of a selectable marker into said genome. In one aspect, the methods employ a linear DNA construct comprising a donor DNA sequence flanked by long homology arms 900 nucleotides in length) for the introduction of said donor DNA into the genome of a competent *Bacillus* sp. cell, and as such provides a highly effective system for integrating donor DNA sequences into the genome of said competent *Bacillus* sp. cell, without the need to integrate a selectable marker in the genome of said *Bacillus* sp. cell, and without the need of a guided Cas system.

The present disclosure further includes methods and compositions for deleting a nucleotide sequence in the genome of a *Bacillus* sp. cell without the use of a selectable marker, the method comprising providing a population of competent *Bacillus* sp. cells, and introducing a linear DNA construct into at least one *Bacillus* sp. cell of said population of cells, wherein said DNA construct comprises an upstream homology arm (HR1) and a downstream homology arm (HR2), wherein each homology arm is at least 900 nucleotides in length and has sequence homology to a genomic DNA region flanking said nucleotide sequence to be deleted, wherein said DNA construct does not comprise a selectable marker.

The present document is organized into a number of sections for ease of reading; however, the reader will appreciate that statements made in one section may apply to other sections. In this manner, the headings used for different sections of the disclosure should not be construed as limiting.

The headings provided herein are not limitations of the various aspects or embodiments of the present compositions and methods which can be had by reference to the specification as a whole. Accordingly, the terms defined immediately below are more fully defined by reference to the specification as a whole.

Unless defined otherwise, all technical and scientific terms used herein have the same meaning as commonly understood by one of ordinary skill in the art to which the present compositions and methods belongs. Although any methods and materials similar or equivalent to those described herein can also be used in the practice or testing of the present compositions and methods, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited.

As used herein, the term "disclosure" or "disclosed disclosure" is not meant to be limiting, but applies generally to any of the disclosures defined in the claims or described herein. These terms are used interchangeably herein.

Cas Genes and Proteins

CRISPR (clustered regularly interspaced short palindromic repeats) loci refers to certain genetic loci encoding components of DNA cleavage systems, for example, used by bacterial and archaeal cells to destroy foreign DNA (Horvath and Barrangou, 2010, Science 327:167-170; WO2007/025097, published Mar. 1, 2007). A CRISPR locus can consist of a CRISPR array, comprising short direct repeats (CRISPR repeats) separated by short variable DNA sequences (called 'spacers'), which can be flanked by diverse Cas (CRISPR-associated) genes. The number of CRISPR-associated genes at a given CRISPR locus can vary between species. Multiple CRISPR/Cas systems have been described including Class 1 systems, with multisubunit effector complexes (comprising type I, type III and type IV subtypes), and Class 2 systems, with single protein effectors (comprising type II and type V subtypes, such as but not limiting to Cas9, Cpf1, C2c1, C2c2, C2c3). Class 1 systems (Makarova et al. 2015, Nature Reviews; Microbiology Vol. 13:1-15; Zetsche et al., 2015, Cell 163, 1-13; and WO 2013/176772 A1 published on Nov. 23, 2013 incorporated by reference herein). The type II CRISPR/Cas system from bacteria employs a crRNA (CRISPR RNA) and tracrRNA (trans-activating CRISPR RNA) to guide the Cas endonuclease to its DNA target. The crRNA contains a spacer region complementary to one strand of the double strand DNA target and a region that base pairs with the tracrRNA (trans-activating CRISPR RNA) forming a RNA duplex that directs the Cas endonuclease to cleave the DNA target. Spacers are acquired through a not fully understood process involving Cas1 and Cas2 proteins. All type II CRISPR/Cas loci contain casl and cas2 genes in addition to the cas9 gene (Chylinski et al., 2013, RNA Biology 10:726-737; Makarova et al. 2015, Nature Reviews Microbiology Vol. 13:1-15). Type II CRISPR-Cas loci can encode a tracrRNA, which is partially complementary to the repeats within the respective CRISPR array, and can comprise other proteins such as Csn1 and Csn2. The presence of cas9 in the vicinity of Cas 1 and cas2 genes is the hallmark of type II loci (Makarova et al. 2015, Nature Reviews Microbiology Vol. 13:1-15). Type I CRISPR-Cas (CRISPR-associated) systems consist of a complex of proteins, termed Cascade (CRISPR-associated complex for antiviral defense), which function together with a single CRISPR RNA (crRNA) and Cas3 to defend against invading viral DNA (Brouns, S. J. J. et al. Science 321:960-964; Makarova et al. 2015, Nature Reviews; Microbiology Vol. 13:1-15, which are incorporated in their entirety herein).

The term "Cas gene" herein refers to a gene that is generally coupled, associated or close to, or in the vicinity of flanking CRISPR loci. The terms "Cas gene", "cas gene", "CRISPR-associated (Cas) gene" and "Clustered Regularly Interspaced Short Palindromic Repeats-associated gene" are used interchangeably herein. The term "Cas protein" or "Cas polypeptide" refers to a polypeptide encoded by a Cas (CRISPR-associated) gene. A Cas protein includes a Cas endonuclease.

A Cas protein may be a bacterial or archaeal protein. Type I-III CRISPR Cas proteins herein are typically prokaryotic in origin; type I and III Cas proteins can be derived from bacterial or archaeal species, whereas type II Cas proteins (i.e., a Cas9) can be derived from bacterial species, for example. In other aspects, Cas proteins include one or more of Cas1, Cas1B, Cas2, Cas3, Cas4, Cas5, Cas6, Cas7, Cas8, Cas9, Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologs thereof, or modified versions thereof. A Cas protein includes a Cas9 protein, a Cpf1 protein, a C2c1 protein, a C2c2 protein, a C2c3 protein, Cas3, Cas3-HD, Cas 5, Cas7, Cas8, Cas10, or combinations or complexes of these.

The term "Cas endonuclease" refers to a Cas polypeptide (Cas protein) that, when in complex with a suitable polynucleotide component, is capable of recognizing, binding to, and optionally nicking or cleaving all or part of a specific DNA target sequence. A Cas endonuclease is guided by the guide polynucleotide to recognize, bind to, and optionally nick or cleave all or part of a specific target site in double stranded DNA (e.g., at a target site in the genome of a cell). A Cas endonuclease described herein comprises one or more nuclease domains. The Cas endonucleases employed in donor DNA insertion methods described herein are endonucleases that introduce single or double-strand breaks into the DNA at the target site. Alternatively, a Cas endonuclease may lack DNA cleavage or nicking activity, but can still specifically bind to a DNA target sequence when complexed with a suitable RNA component.

As used herein, a polypeptide referred to as a "Cas9" (formerly referred to as Cas5, Csn1, or Csx12) or a "Cas9 endonuclease" or having "Cas9 endonuclease activity"

refers to a Cas endonuclease that forms a complex with a crNucleotide and a tracrNucleotide, or with a single guide polynucleotide, for specifically binding to, and optionally nicking or cleaving all or part of a DNA target sequence. A Cas9 endonuclease comprises a RuvC nuclease domain and an HNH (H-N-H) nuclease domain, each of which can cleave a single DNA strand at a target sequence (the concerted action of both domains leads to DNA double-strand cleavage, whereas activity of one domain leads to a nick). In general, the RuvC domain comprises subdomains I, II and III, where domain I is located near the N-terminus of Cas9 and subdomains II and III are located in the middle of the protein, flanking the HNH domain (Makarova et al. 2015, Nature Reviews Microbiology Vol. 13:1-15, Hsu et al., 2013, Cell 157:1262-1278). Cas9 endonucleases are typically derived from a type II CRISPR system, which includes a DNA cleavage system utilizing a Cas9 endonuclease in complex with at least one polynucleotide component. For example, a Cas9 can be in complex with a CRISPR RNA (crRNA) and a trans-activating CRISPR RNA (tracrRNA). In another example, a Cas9 can be in complex with a single guide RNA (Makarova et al. 2015, Nature Reviews Microbiology Vol. 13:1-15).

Guided Cas systems

The terms "guide RNA/Cas endonuclease complex", "guide RNA/Cas endonuclease system", "guide RNA/Cas complex", "guide RNA/Cas system", "gRNA/Cas complex", "gRNA/Cas system", "RNA-guided endonuclease", "RGEN" are used interchangeably herein and refer to at least one RNA component and at least one Cas endonuclease, that are capable of forming a complex, wherein said guide RNA/Cas endonuclease complex can direct the Cas endonuclease to a DNA target site, enabling the Cas endonuclease to recognize, bind to, and optionally nick or cleave (introduce a single or double-strand break) the DNA target site.

DNA Constructs and Donor DNAs

Homology-directed repair (HDR) is a mechanism in cells to repair double-stranded and single stranded DNA breaks. Homology-directed repair includes homologous recombination (HR) and single-strand annealing (SSA) (Lieber, 2010 Annu. Rev. Biochem. 79:181-211). The most common form of HDR is called homologous recombination (HR), which has the longest sequence homology requirements between the donor and acceptor DNA. Other forms of HDR include single-stranded annealing (SSA) and breakage-induced replication, and these require shorter sequence homology relative to HR. Homology-directed repair at nicks (single-stranded breaks) can occur via a mechanism distinct from HDR at double-strand breaks (Davis and Maizels. PNAS (0027-8424), 111 (10), p. E924-E932).

Homologous recombination includes the exchange of DNA fragments between two DNA molecules at the sites of homology. The frequency of homologous recombination is influenced by a number of factors. Different organisms vary with respect to the amount of homologous recombination and the relative proportion of homologous to non-homologous recombination. The length of the homology region (homology arm) needed to observe homologous recombination varies among organisms. Alteration of the genome of a prokaryotic organism (cell), for example, through homologous recombination (HR), is a powerful tool for genetic engineering. Homologous recombination has also been accomplished in other organisms. For example, at least 150-200 bp of homology was required for homologous recombination in the parasitic protozoan Leishmania (Papadopoulou and Dumas, (1997) Nucleic Acids Res 25:4278-

86) and 150-200bp of homology is required for efficient recombination in the protobacterium *E. coli* (Lovett et al. (2002) Genetics 160:851-859).

By "homology" is meant DNA sequences that are similar. For example, a "region of homology to a genomic region" that is found on the DNA construct described herein is a region of DNA that has a similar sequence to a given "genomic region" in the cell or organism genome. A region of homology can be of any length that is sufficient to promote homologous recombination. For example, the region of homology on a linear DNA construct describe herein can comprise at least about between 900 base pairs (bps) and 2000 bps; 900 base pairs (bps) and 3000 bps; between 1000 base pairs (bps) and 2000 bps; between 1000 base pairs (bps) and 3000 bps; between 1000 base pairs (bps) and 4000 bps; between 2000 bps and 3000 bps; between 2000 bps and 4000 bps; between 2000 bps and 5000 bps; between 2000 bps and 6000 bps, between 3000 bps and 4000 bps; between 3000 bps and 5000 bps; between 3000 bps and 6000 bps, between 4000 bps and 5000 bps; between 4000 bps and 6000 bps, between 5000 bps and up to 6000 bps in length such that the region of homology has sufficient homology to undergo homologous recombination with the corresponding genomic region. "Sufficient homology" indicates that two polynucleotide sequences have sufficient structural similarity to act as substrates for a homologous recombination reaction. The structural similarity includes overall length of each polynucleotide fragment, as well as the sequence similarity of the polynucleotides. Sequence similarity can be described by the percent sequence identity over the whole length of the sequences, and/or by conserved regions comprising localized similarities such as contiguous nucleotides having 100% sequence identity, and percent sequence identity over a portion of the length of the sequences.

The amount of homology can also be described by percent sequence identity over the full aligned length of the two polynucleotides which includes percent sequence identity of about at least 50%, 55%, 60%, 65%, 70%, 71° A, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%. Sufficient homology includes any combination of polynucleotide length, global percent sequence identity, and optionally conserved regions of contiguous nucleotides or local percent sequence identity, for example sufficient homology can be described as a region of 900-7000 bp having at least 80% sequence identity to a region of the genome. Sufficient homology can also be described by the predicted ability of two polynucleotides to specifically hybridize under high stringency conditions, see, for example, Sambrook et al., (1989) *Molecular Cloning: A Laboratory Manual*, (Cold Spring Harbor Laboratory Press, NY); *Current Protocols in Molecular Biology*, Ausubel et al., Eds (1994) Current Protocols, (Greene Publishing Associates, Inc. and John Wiley & Sons, Inc.); and, Tijssen (1993) *Laboratory Techniques in Biochemistry and Molecular Biology—Hybridization with Nucleic Acid Probes*, (Elsevier, New York).

As used herein, a "genomic region" is a segment of a chromosome in the genome of a cell that is present on either side of the genomic sequence to be modified or, alternatively, also comprises a portion of the genomic region to be modified. The genomic region as described herein can be at least 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 5000, 6000 nucleotides and up to 7000 nucleotides in length.

The genomic region as described herein can comprise at least about between 900 base pairs (bps) and 2000 bps ,900 base pairs (bps) and 3000 bps; between 1000 base pairs (bps) and 2000 bps, between 1000 base pairs (bps) and 3000 bps, between 1000 base pairs (bps) and 4000 bps, between 2000 bps and 3000 bps; between 2000 bps and 4000 bps; between 2000 bps and 5000 bps; between 2000 bps and 6000 bps, between 3000 bps and 4000 bps; between 3000 bps and 5000 bps; between 3000 bps and 6000 bps, between 4000 bps and 5000 bps; between 4000 bps and 6000 bps, between 5000 bps and up to 6000 bps in length or more bases such that the genomic region has sufficient homology to undergo homologous recombination with the corresponding region of homology.

As described herein, the genomic sequence to be modified includes a single base to be modified (such as a point mutation described herein) and a gene or chromosome fragment to be deleted. In the aspect where it is desired to integrate a donor DNA into the genome of a *Bacillus* sp. cell, the genomic regions are directly located next to one another on the *Bacillus* sp. genome.

The structural similarity between a given genomic region and the corresponding region of homology found on the DNA construct (HR1, HR2) can be any degree of sequence identity that allows for homologous recombination to occur. For example, the amount of homology or sequence identity shared by the "region of homology" of the DNA construct and the "genomic region" of the organism genome can be at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, such that the sequences undergo homologous recombination As used herein a "DNA construct" refers to a DNA sequence comprising at least a first homology arm (HR1, also referred to as the 5 prime homology arm, 5'HR) and a second homology arm (HR2, also referred to as a 3 prime Homology arm,3'HR. The DNA construct can further comprise a donor DNA in between the first and second homology arm (donor DNA flanked by homology arms).

As used herein a "linear DNA construct" refers to a single stranded or double stranded DNA construct that is linear.

As used herein, "homology arm" refers to a nucleic acid sequence, which is homologous to a genomic region in the *Bacillus* sp. genome. The structural similarity between a given genomic region and the corresponding homology arm (HR1, HR2) found on the DNA construct can be any degree of sequence identity that allows for homologous recombination to occur. For example, the amount of homology or sequence identity shared by the "region of homology" of the HR1 and/or HR2 of the DNA construct and the "genomic region" of the organism genome can be at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, such that the sequences undergo homologous recombination In one aspect, the homology arms of the present disclosure, flanking a double stranded donor DNA comprising a nucleotide sequence of interest to be integrated into the *Bacillus* sp. genome, and located on a linear double stranded DNA construct described herein, include about between 900 base pairs (bps) and 2000 bps , 900 base pairs (bps) and 3000 bps, between 1000 base pairs (bps) and 2000 bps, between 1000 base pairs (bps) and 3000 bps, between 1000 base pairs (bps) and 4000 bps, 900 base pairs (bps) and 2000 bps;

between 2000 bps and 3000 bps; between 2000 bps and 4000 bps; between 2000 bps and 5000 bps; between 2000 bps and 6000 bps, between 3000 bps and 4000 bps; between 3000 bps and 5000 bps; between 3000 bps and 6000 bps, between 4000 bps and 5000 bps; between 4000 bps and 6000 bps, between 5000 bps and up to 7000 bps.

In one aspect, the homology arms of the present disclosure, flanking a single stranded donor DNA comprising a nucleotide sequence of interest to be integrated into the *Bacillus* sp. genome, and located on a linear single stranded DNA construct, include about between 900 nucleotides and 2000 nucleotides, 900 nucleotides and 3000 nucleotides, between 1000 nucleotides and 2000 nucleotides, between 1000 nucleotides and 3000 nucleotides, between 1000 nucleotides and 4000 nucleotides, between 900 nucleotides and 2000 nucleotides; between 2000 nucleotides and 3000 nucleotides; between 2000 nucleotides and 4000 nucleotides; between 2000 nucleotides and 5000 nucleotides; between 2000 nucleotides and 6000 nucleotides; between 3000 nucleotides and 4000 nucleotides; between 3000 nucleotides and 5000 nucleotides; between 3000 nucleotides and 6000 nucleotides; between 4000 nucleotides and 5000 nucleotides; between 4000 nucleotides and 6000 nucleotides; between 5000 nucleotides, between 6000 nucleotides and up to 7000 nucleotides.

As used herein, "donor DNA" and "donor DNA sequence" refers to a DNA sequence that comprises a nucleotide sequence of interest to be inserted into the genome of a *Bacillus* sp. cell.

The donor DNA as described herein is flanked by a first homology arm (HR1, also referred to as the 5 prime homology arm, 5'HR) and a second homology arm (HR2, also referred to as a 3 prime Homology arm,3'HR), which determine the location of the integration of the donor DNA into the competent *Bacillus* sp. genome In one aspect, the nucleotide sequence of interest of the donor DNA sequence include a polynucleotide of interest, a recombinant DNA, a synthetic sequence of interest, a heterologous sequence of interest, a homologous sequence of interest, a gene of interest, one or more expression cassettes, one or more recombinant DNA constructs, one or more expression cassettes, a nucleotide sequence (such as but not limiting to a single base) having a desired modification/mutation (such as a base substitution) when compared to the native non-transformed genomic sequence, a transcriptional regulatory sequence, a translational regulatory sequence, a promoter sequence, a terminator sequence, a transgenic nucleic acid sequence, an antisense sequence complementary to at least a portion of the messenger RNA, a heterologous sequence, or any one combination thereof.

Polynucleotides of interests described herein can be provided in an expression cassette for expression in an organism of interest.

The term "expression", as used herein, refers to the production of a functional end-product (e.g., a crRNA, a tracrRNA, a mRNA, a guide RNA, sRNA, siRNA, antisense RNA, or a polypeptide (protein) in either precursor or mature form. The term "expression" includes any step involved in the production of a polypeptide including, but not limited to, transcription, post-transcriptional modification, translation, post-translational modification, and secretion.

The expression cassette can include 5' and 3' regulatory sequences and or tags and synthetic sequences operably linked to a polynucleotide as disclosed herein.

The expression cassettes disclosed herein may include in the 5'-3' direction of transcription, a transcriptional and translational initiation region (i.e., a promoter), a 5' untranslated region, polynucleotides encoding various proteins tags and sequences, a polynucleotide of interest, and a transcriptional and translational termination region (i.e., termination region) functional in the *Bacillus* sp. (host) cell. Expression cassettes are also provided with a plurality of restriction sites and/or recombination sites for insertion of the polynucleotide to be under the transcriptional regulation of the regulatory regions described elsewhere herein. The regulatory regions (i.e., promoters, transcriptional regulatory regions, and translational termination regions) and/or the polynucleotide of interest may be native/analogous to the host cell or to each other. Other polynucleotide sequences encoding various protein sequences may be appended to either the 5' or 3' end of the polynucleotide of interest. Alternatively, the regulatory regions and/or the polynucleotide of interest may be heterologous to the host cell or to each other.

In certain embodiments the polynucleotides disclosed herein can be stacked with any combination of polynucleotide sequences of interest or expression cassettes as disclosed elsewhere herein or known in the art. The stacked polynucleotides may be operably linked to the same promoter as the initial polynucleotide, or may be operably linked to a separate promoter polynucleotide.

Expression cassettes may comprise a promoter operably linked to a polynucleotide of interest, optionally along with a corresponding termination region. The termination region may be native to the transcriptional initiation region, may be native to the operably linked polynucleotide of interest or to the promoter sequences, may be native to the host organism, or may be derived from another source (i.e., foreign or heterologous). Convenient termination regions are available from phage sequences, e.g., lambda phage t0 termination region or strong terminators from prokaryotic ribosomal RNA operons or genes involved in the secretion of extracellular proteins (e.g., aprE from *B. subtilis,* aprL from *B. licheniformis*). Convenient termination regions are available from the Ti-plasmid of *A. tumefaciens,* such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639.

Where appropriate, the polynucleotides of interest may be optimized for increased expression in the transformed or targeted organism. For example, the polynucleotides can be synthesized or altered to use organism-preferred codons for improved expression.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences. Such leader sequences can act to enhance translation or the level of RNA stability. 5' leader sequences used interchangeably with 5' untranslated regions could come from well-known and well characterized bacterial UTRs such as those from the *Bacillus subtilis* aprE gene or the *Bacillus licheniformis* amyL gene or any bacterial ribosomal protein gene. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86:6126-6130); potyvirus leaders, for example, TEV leader (Tobacco Etch Virus) (Gallie et al. (1995) *Gene* 165(2):233-238), MDMV leader (Maize Dwarf Mosaic Virus) (Johnson et al. (1986) *Virology* 154:9-20), and human immunoglobulin heavy-chain binding protein (BiP) (Macejak et al. (1991) *Nature* 353:90-94); untranslated leader from the coat protein mRNA of alfalfa mosaic virus (AMV RNA 4) (Jobling et al. (1987) Nature 325:622-625); tobacco mosaic virus leader (TMV) (Gallie et al. (1989) in *Molecular Biology of RNA,* ed. Cech (Liss, New York), pp. 237-256); and maize chlorotic mottle virus leader (MCMV) (Lommel et al. (1991) *Virology* 81:382-385). See also, Della-Cioppa et al. (1987) *Plant Physiol.* 84:965-968. Other methods known to enhance translation can also be utilized, for example, introns, and the like.

In preparing the expression cassette, the various DNA fragments may be manipulated so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, re-substitutions, e.g., transitions and transversions, may be involved.

In some embodiments, a nucleotide sequence encoding a lipase or protease protein is operably linked to a control element, e.g., a transcriptional control element, such as a promoter. The transcriptional control element may be functional in either a eukaryotic cell or a prokaryotic cell (e.g., bacterial or *Bacillus* sp. cell).

Non-limiting examples of suitable prokaryotic promoters (promoters functional in a prokaryotic cell) and promoter sequence regions for use in the expression of genes, open reading frames (ORFs) thereof and/or variant sequences thereof in *Bacillus* sp. cells are generally known on one of skill in the art. Promoter sequences of the disclosure are generally chosen so that they are functional in the *Bacillus* sp. cells (e.g., *B. licheniformis* cells, *B. subtilis* cells and the like). Likewise, promoters useful for driving gene expression in *Bacillus* sp. cells include, but are not limited to, the promoters of the *Bacillus licheniformis* amylase gene (amyL), the promoters of the *Bacillus stearothermophilus* maltogenic amylase gene (amyM), the promoters of the *Bacillus amyloliquefaciens* amylase (amyQ), the promoters of the *Bacillus subtilis* xylA and xylB genes, the *Bacillus subtilis* alkaline protease (aprE) promoter (Stahl et al., 1984), the α-amylase promoter of *Bacillus subtilis* (Yang et al., 1983), the α-amylase promoter of *Bacillus amyloliquefaciens* (Tarkinen et al., 1983), the neutral protease (nprE) promoter from *Bacillus subtilis* (Yang et al., 1984), a mutant aprE promoter (PCT Publication No. WO2001/51643) or any other promoter from *Bacillus licheniformis* or other related *Bacilli.* In certain other embodiments, the promoter is a ribosomal protein promoter or a ribosomal RNA promoter (e.g., the rrnI promoter) disclosed in U.S. Patent Publication No. 2014/0329309. Synthetic promoters like spac can be both constitutive or inducible depending on other accessory factors. Phage promoters like n25, lambda pL or pR can be constitutive or inducible much in the same way. Methods for screening and creating promoter libraries with a range of activities (promoter strength) in *Bacillus* sp. cells is describe in PCT Publication No. WO2003/089604.

Constitutive promoters functional in *Bacillus* sp. include, but are not limited to , the promoters of the *Bacillus licheniformis* amylase gene (amyL), the promoters of the *Bacillus stearothermophilus* maltogenic amylase gene (amyM), the promoters of the *Bacillus amyloliquefaciens* amylase (amyQ), the *Bacillus subtilis* alkaline protease (aprE) promoter, the a-amylase promoter of *Bacillus subtilis* (Yang et al., 1983), the α-amylase promoter of *Bacillus amyloliquefaciens* (Tarkinen et al., 1983), the neutral protease (nprE) promoter from *Bacillus subtilis* (Yang et al., 1984).

In one aspect, the donor DNA comprises a recombinant DNA to be integrated into the *Bacillus* sp. genome.

As used herein, "recombinant" refers to an artificial combination of two otherwise separated segments of sequence, e.g., by chemical synthesis or by the manipulation of isolated segments of nucleic acids by genetic engineering techniques. The term "recombinant," when used in reference to a biological component or composition (e.g., a cell, nucleic acid, polypeptide/enzyme, vector, etc.) indicates that the biological component or composition is in a state that is not found in nature. In other words, the biological component or composition has been modified by human intervention from its natural state. For example, a recombinant cell encompasses a cell that expresses one or more genes that are not found in its native (i.e., non-recombinant) cell, a cell that expresses one or more native genes in an amount that is different than its native cell, and/or a cell that expresses one or more native genes under different conditions than its native cell. Recombinant nucleic acids may differ from a native sequence by one or more nucleotides, be operably linked to heterologous sequences (e.g., a heterologous promoter, a sequence encoding a non-native or variant signal sequence, etc.), be devoid of intronic sequences, and/or be in an isolated form. Recombinant polypeptides/enzymes may differ from a native sequence by one or more amino acids, may be fused with heterologous sequences, may be truncated or have internal deletions of amino acids, may be expressed in a manner not found in a native cell (e.g., from a recombinant cell that over-expresses the polypeptide due to the presence in the cell of an expression vector encoding the polypeptide), and/or be in an isolated form. It is emphasized that in some embodiments, a recombinant polynucleotide or polypeptide/enzyme has a sequence that is identical to its wild-type counterpart but is in a non-native form (e.g., in an isolated or enriched form).

As used herein, "recombinant DNA " refers to a DNA sequence comprising at least one expression cassette comprising an artificial combination of nucleic acid fragments. The recombinant DNA can include 5' and 3' regulatory sequences operably linked to a polynucleotide of interest as disclosed herein. For example, a recombinant DNA may comprise regulatory sequences and coding sequences that are derived from different sources.

Standard recombinant DNA and molecular cloning techniques used herein are well known in the art and are described more fully in Sambrook et al., *Molecular Cloning: A Laboratory Manual; Cold Spring Harbor Laboratory:* Cold Spring Harbor, NY (1989).

A variety of methods are available to identify those cells having an altered genome without using a screenable marker phenotype. Such methods can be viewed as directly analyzing a target sequence to detect any change in the genome sequence, including but not limited to PCR methods, sequencing methods, nuclease digestion, Southern blots, and any combination thereof.

Use of Linear DNA Constructs Comprising Long Homology Arms of at Least 900 Nucleotides in Length for Efficient Genome Modification in Competent *Bacillus* sp.

The present disclosure includes methods for modifying the genome of *Bacillus* sp. cells without the use or integration of a selectable marker and without the use or integration of a Cas endonuclease.

Without wishing to be bound by any particular theory, mechanism, or mode of action, Applicant has surprisingly and unexpectedly discovered that when a linear DNA construct comprising long homology arms (each homology arm having at least 900 nucleotides) is introduced into competent *Bacillus* sp. cells, a high efficiency in genome modification (such as but not limited to donor DNA sequence integration, gene deletions, and mutations depending on the type of linear DNA construct used) is observed, wherein the introduction and genome modification occurs without the use of a selectable marker or a guided Cas endonuclease system.

The present disclosure includes methods and compositions for integrating donor DNA sequences into the genome of a competent *Bacillus* sp. cell using a linear DNA construct comprising a donor DNA and without the use of a guided Cas endonuclease system and without the integration of a selectable marker into said genome.

In one embodiment, the method is a method for integrating a donor DNA into the genome of a *Bacillus* sp. cell without the use of a selectable marker, the method comprising providing a population of competent *Bacillus* sp. cells and introducing a linear DNA construct into at least one *Bacillus* sp. cell of said population of cells, wherein said DNA construct comprises a donor DNA flanked by an upstream homology arm (HR1) and a downstream homology arm (HR2), wherein each homology arm is at least 900 nucleotides in length, wherein said DNA construct does not comprise a selectable marker, and optionally further comprising growing progeny cells from said at least one *Bacillus* sp. cell on media that do not comprise a selectable marker, and identifying a *Bacillus* sp. progeny cell that has the donor DNA sequence stably integrated in its genome.

As described herein, integration of a donor DNA into the genome of a *Bacillus* sp. cell without the use of a selectable marker and without the use of a guided Cas systems can occur at a high frequency by introducing a linear DNA construct comprising a donor DNA flanked by an upstream homology arm (HR1) and a downstream homology arm (HR2), wherein each homology arm is at least 900 nucleotides in length into a competent *Bacillus* sp. cell.

The disclosure includes methods for deleting genes of interest into the genome of *Bacillus* sp. cells.

In one embodiment, the method is a method for deleting a nucleotide sequence in the genome of a *Bacillus* sp. cell without the use of a selectable marker, the method comprising providing a population of competent *Bacillus* sp. cells, and introducing a linear DNA construct into at least one *Bacillus* sp. cell of said population of cells, wherein said DNA construct comprises an upstream homology arm (HR1) and a downstream homology arm (HR2), wherein each homology arm is at least 900 nucleotides in length and has sequence homology to a genomic DNA region flanking said nucleotide sequence to be deleted, wherein said DNA construct does not comprise a selectable marker.

The disclosure includes methods for providing mutations (such as but not limiting to point mutations) into the genome of *Bacillus* sp. cells.

In one embodiment, the method is a method for introducing a mutation into the genome of a *Bacillus* sp. cell without the use of a selectable marker, the method comprising providing a population of competent *Bacillus* sp. cells and introducing a linear DNA construct into at least one *Bacillus* sp. cell of said population of cells, wherein said DNA construct comprises a nucleotide sequence having the desired mutation flanked by an upstream homology arm (HR1) and a downstream homology arm (HR2), wherein each homology arm is at least 900 nucleotides in length, and wherein said DNA construct does not comprise a selectable marker. In one embodiment, the above method further comprising growing progeny cells from said at least one *Bacillus* sp. cell on media that do not comprise a selectable marker, and identifying a *Bacillus* sp. progeny cell that has mutation in its genome. In one aspect, the nucleotide sequence having the desired mutation comprises of at least 1, 2, 3, 4, 5, 6, 7, 8, 9, or 10 base modifications or substitutions compared to the native sequence of the *Bacillus* sp. cell (genomic *Bacillus* sp. DNA sequence prior to the modification). In one aspect, the nucleotide sequence having the desired mutation (base substitutions) consists of 1, 2, 3, 4, 5, 6, 7, 8, 9, or 10 bases.

The disclosure includes methods for Introducing multiple copies of a gene expression cassette. One of the bottlenecks in development of *Bacillus* sp. hosts for enzyme production is an antibiotic resistant marker (ARM)-free integration of multi-copy enzyme expression cassettes in the chromosome. Existing approaches such as using an integration vector, Cre/loxP system, and auxotrophic marker are time consuming, and the editing efficiencies are relatively low.

Methods described herein allow for the integration of multiple copies of a gene of interest (gene expression cassettes of interest) using a donor DNA flanked by an upstream homology arm (HR1) and a downstream homology arm (HR2), wherein each homology arm is at least 900 nucleotides in length, resulting in a high efficiency of gene integration.

A multi-copy gene expression cassette or multi-copy expression cassette are used interchangeably herein and refer to multiple copies of the same expression cassette comprising at least one gene of interest. In one aspect, the multiple copies of said gene expression cassette are selected from the group consisting of 2 copies, 3 copies, 4 copies, 5 copies, 6 copies, 7 copies, 8 copies, 9 copies and up to 10 copies.

Definitions

Unless defined otherwise, all technical and scientific terms used herein have the same meaning as commonly understood by one of ordinary skill in the art to which the present compositions and methods apply.

An "allele" or "allelic variant" is one of several alternative forms of a gene occupying a given locus on a chromosome. When all the alleles present at a given locus on a chromosome are the same, that organism is homozygous at that locus. If the alleles present at a given locus on a chromosome differ, that organism is heterozygous at that locus. An allelic variant of a polypeptide is a polypeptide encoded by an allelic variant of a gene.

As used herein, "host cell" refers to a cell that has the capacity to act as a host or expression vehicle for a newly introduced DNA sequence. Thus, in certain embodiments of the disclosure, the host cells are *Bacillus* sp. cells.

A "recombinant host cell" (also referred to as a "genetically modified host cell") is a host cell into which has been introduced a heterologous nucleic acid, e.g., a recombinant DNA construct, or which has been introduced and comprises a genome modification system such as the guide RNA/Cas endonuclease system described herein. For example, a subject bacterial host cell includes a genetically modified *Bacil-*

*lus* sp. cell by virtue of introduction into a suitable *Bacillus* sp. cell of an exogenous nucleic acid (e.g., a plasmid or circular recombinant DNA construct).

As defined herein, a "parental cell" or a "parental (host) cell" may be used interchangeably and refer to "unmodified" parental cells. For example, a "parental" cell refers to any cell or strain of microorganism in which the genome of the "parental" cell is altered (e.g., via one or more mutations/modifications introduced into the parental cell) to generate a modified "daughter" cell thereof.

As used herein, a "modified cell" or a "modified (host) cell" may be used interchangeably and refer to recombinant (host) cells that comprise at least one genetic modification which is not present in the "parental" host cell from which the modified cells are derived.

As used herein, "the genus *Bacillus*" or "*Bacillus* sp." cells include all species within the genus "*Bacillus*'" as known to those of skill in the art, including but not limited to *Bacillus subtilis, Bacillus licheniformis, Bacillus lentus, Bacillus brevis, Bacillus stearothermophilus, Bacillus alkalophilus, Bacillus amyloliquefaciens, Bacillus clausii, Bacillus. halodurans, Bacillus. megaterium, Bacillus coagulans, Bacillus circulans, Bacillus lautus,* and *Bacillus thuringiensis.* It is recognized that the genus *Bacillus* continues to undergo taxonomical reorganization. Thus, it is intended that the genus include species that have been reclassified, including but not limited to such organisms as *B. stearothermophilus,* which is now named "*Geobacillus stearothermophilus*".

As used herein "competent *Bacillus* sp. cells" or "cells from a competent *Bacillus* sp. strain" are used interchangeable and refer to *Bacillus* sp. cells that were made competent by any method know in the art. In one aspect, the *Bacillus* sp. cells is made competent by at least one copy of an introduced nucleic acid construct comprising a promoter operably linked to a polynucleotide encoding a polypeptide selected from the group of ComK, ComS, ComS1, ComG, ComC, ComDE, Spo0H, AbrB, Spo0A, Spo0K, Sin, DegU, Com A, ComP, ComQ, COmB, srfA, ComK, or any one combination thereof (Dubnau D., 1991, Microbiological Reviews, Vol 55, No. 3, p. 395-424; Hamoen et al., 2003, Microbiology, 149, pg. 9-17).

In one aspect, the *Bacillus* sp. cells is made competent through natural competence, artificial competence or induced competence (Dubnau D., 1991, Microbiological Reviews, Vol 55, No. 3, p. 395-424; Hamoen et al., 2003, Microbiology, 149, pg. 9-17; Jarmer Hanne et al. FEMS Microbiology Letters 206, pg. 197-200).

In one aspect, methods for making non-competent *Bacillus* sp. cells competent include the introduction and expression of ComS, ComS1, ComK, or any combination of these polypeptide (or genes encoding these polypeptides) in *Bacillus* sp. cells such that the cells become more competent for the uptake of DNA.

In one aspect, methods for making non-competent *Bacillus* sp. cells competent include the introduction into a non-competent *Bacillus* sp. cells at least one copy of a nucleic acid construct comprising an inducible promoter operably linked to a polynucleotide encoding a polypeptide selected from the group of ComK, ComS, ComS1, ComG, ComC, ComDE, Spo0H, AbrB, Spo0A, Spo0K, Sin, DegU, Com A, ComP, ComQ, COmB, srfA, ComK, or any one combination thereof.

Examples of such inducible promoter include, but are not limited to, xylAp; promoters induced with sugars such as maltose, mannitol or arabinose; small molecules such as the tetA or spac promoters; temperature induced promoters such as the ydhl promoter); tandem promoters (see WO99/043835 and 05/098016) preferably the tandem promoter is Pconsensus amyQ-PcryIIIA-cryIIIA , or PamyL4199-Pconsensus amyQ-PcryIIIA-cryIIIA (see PCT/US2007/088186); or any one combination thereof.

As used herein "super competent *Bacillus* sp. cells" or "cells from a super competent *Bacillus* sp. strain" are used interchangeable and refer to competent *Bacillus* sp. cells wherein greater than 1% of a cell population is transformable with chromosomal *Bacillus* sp. DNA. Alternatively, super competent means that greater than 10% of a cell population is transformable with a self-replicating *Bacillus* plasmid. Preferably, the super competent *Bacillus* sp. cells will be transformed at a rate greater than observed for the wild-type or parental cell population.

In one aspect the *Bacillus* sp. cells is made super competent by at least one copy of an introduced nucleic acid construct comprising a xylose-inducible promoter (Pxyl) operably linked to a polynucleotide encoding a ComK polypeptide (Pxyl-ComK) producing the super-competent *Bacillus* sp. Pxyl-ComK strain.

In one aspect the super competent *Bacillus* sp. strain is a strain that is made supercompetent by introduction into a *Bacillus* sp. cells at least one copy of a nucleic acid construct comprising an promoter (such as but not limiting to an inducible promoter) operably linked to a polynucleotide encoding a polypeptide selected from the group of ComK, ComS, ComS1, ComG, ComC, ComDE, Spo0H, AbrB, Spo0A, Spo0K, Sin, DegU, Com A, ComP, ComQ, COmB, srfA, ComK, or any one combination thereof.

In one aspect the competent or supercompetent *Bacillus* sp. strain is selected from the group consisting of *Bacillus subtilis* 168 (BGSC1A1), *Bacillus subtilis* 168delta4 with deletions of spollAC, aprE, nprE, and amyE genes, *Bacillus subtilis* A164delta5 (as above but with the additional deletion of srfAC U.S. Pat. No. 5,891,701), *Bacillus subtilis* MDT101 (expressing the DNA meythltransferase of *B. licheniformis* SJ1904) and *Bacillus licheniformis* SJ1904 (U.S. Pat. No. 5,733,753).

The term "increased" as used herein may refer to a quantity or activity that is at least 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 100%, or at least about 2, 3, 4, 5, 6, 7, 8, 9, 10, 11, 12, 13,14, 15, 16, 17, 18, 19, 20, 21, 22, 23, 24, 25, 26, 27, 28, 29, 30, 31, 32, 33, 34, 35, 36, 37, 38, 39, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390,400, 410, 420,430, 440, 440, 450, 460, 470, 480, 490, or 500 fold more than the quantity or activity for which the increased quantity or activity is being compared. The terms "increased", "greater than", and "improved" are used interchangeably herein. The term "increased" can be used to characterize the transformation or gene editing efficiency obtained by a multicomponent method described herein when compared to a control or reference method described herein, As used herein, the term "integration efficiency" is defined by diving the number of transformed cells having the desired gene of interest integrated into its genome by the total number of transformed cells. This number can be multiplied by 100 to express it as a %.

Integration efficiency (%)=(number of transformed
cells having gene of interest integrated in its
genome/number of total transformed cells)*100

The term "conserved domain" or "motif" means a set of amino acids conserved at specific positions along an aligned sequence of evolutionarily related proteins. While amino acids at other positions can vary between homologous proteins, amino acids that are highly conserved at specific positions indicate amino acids that are essential to the structure, the stability, or the activity of a protein. Because they are identified by their high degree of conservation in aligned sequences of a family of protein homologues, they can be used as identifiers, or "signatures", to determine if a protein with a newly determined sequence belongs to a previously identified protein family.

As used herein, "nucleic acid" means a polynucleotide and includes a single or a double-stranded polymer of deoxyribonucleotide or ribonucleotide bases. Nucleic acids may also include fragments and modified nucleotides. Thus, the terms "polynucleotide", "nucleic acid sequence", "nucleotide sequence" and "nucleic acid fragment" are used interchangeably to denote a polymer of RNA and/or DNA and/or RNA-DNA that is single- or double-stranded, optionally containing synthetic, non-natural, or altered nucleotide bases. Nucleotides (usually found in their 5'-monophosphate form) are referred to by their single letter designation as follows: "A" for adenosine or deoxyadenosine (for RNA or DNA, respectively), "C" for cytosine or deoxycytosine, "G" for guanosine or deoxyguanosine, "U" for uridine, "T" for deoxythymidine, "R" for purines (A or G), "Y" for pyrimidines (C or T), "K" for G or T, "H" for A or C or T, "I" for inosine, and "N" for any nucleotide (nucleotide (e.g., N can be A, C, T, or G, if referring to a DNA sequence; N can be A, C, U, or G, if referring to an RNA sequence).

It is understood that the polynucleotides (or nucleic acid molecules) described herein include "genes", "vectors" and "plasmids".

The term "gene", refers to a polynucleotide that codes for a functional molecule such as, but not limited to, a particular sequence of amino acids, which comprise all, or part of a protein coding sequence, and may include regulatory (non-transcribed) sequences, such as promoter sequences, which determine for example the conditions under which the gene is expressed. The transcribed region of the gene may include untranslated regions (UTRs), including introns, 5'-untranslated regions (UTRs), and 3'-UTRs, as well as the coding sequence. "Native gene" refers to a gene as found in nature with its own regulatory sequences.

A "codon-modified gene" or "codon-preferred gene" or "codon-optimized gene" is a gene having its frequency of codon usage designed to mimic the frequency of preferred codon usage of the host cell. The nucleic acid changes made to codon-optimize a gene are "synonymous", meaning that they do not alter the amino acid sequence of the encoded polypeptide of the parent gene. However, both native and variant genes can be codon-optimized for a particular host cell, and as such no limitation in this regard is intended. Methods are available in the art for synthesizing codon-preferred genes. See, for example, U.S. Pat. Nos. 5,380,831, and 5,436,391, and Murray et al. (1989) *Nucleic Acids Res.* 17:477-498, herein incorporated by reference.

Additional sequence modifications are known to enhance gene expression in a host organism. These include, for example, elimination of: one or more sequences encoding spurious polyadenylation signals, one or more exon-intron splice site signals, one or more transposon-like repeats, and other such well-characterized sequences that may be deleterious to gene expression. The G-C content of the sequence may be adjusted to levels average for a given host organism, as calculated by reference to known genes expressed in the host cell. When possible, the sequence is modified to avoid one or more predicted hairpin secondary mRNA structures.

As used herein, the term "coding sequence" refers to a nucleotide sequence, which directly specifies the amino acid sequence of its (encoded) protein product. The boundaries of the coding sequence are generally determined by an open reading frame (hereinafter, "ORF"), which usually begins with an ATG start codon. The coding sequence typically includes DNA, cDNA, and recombinant nucleotide sequences.

As defined herein, the term "open reading frame" (hereinafter, "ORF") means a nucleic acid or nucleic acid sequence (whether naturally occurring, non-naturally occurring, or synthetic) comprising an uninterrupted reading frame consisting of (i) an initiation codon, (ii) a series of two (2) or more codons representing amino acids, and (iii) a termination codon, the ORF being read (or translated) in the 5' to 3' direction.

The term "chromosomal integration" as used herein refers to a process where the polynucleotide of interest is integrated into the *Bacillus* sp. chromosome. The homology arms of the linear donor DNA construct (linear donor DNA flanked by homology arms) will align with homologous regions of the *Bacillus* sp. chromosome. Subsequently, the sequence between thee homology arms is replaced by the polynucleotide of interest in a double crossover (i.e., homologous recombination).

"Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences include, but are not limited to, promoters, translation leader sequences, 5' untranslated sequences, 3' untranslated sequences, introns, polyadenylation target sequences, RNA processing sites, effector binding sites, and stem-loop structures.

The term "promoter" as used herein refers to a nucleic acid sequence capable of controlling the expression of a coding sequence or functional RNA. In general, a coding sequence is located 3' (downstream) to a promoter sequence. Promoters may be derived in their entirety from a native gene, or be composed of different elements derived from different promoters found in nature, or even comprise synthetic nucleic acid segments. It is understood by those skilled in the art that different promoters may direct the expression of a gene in different cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

"Operably linked" is intended to mean a functional linkage between two or more elements. For example, an operable linkage between a polynucleotide of interest and a regulatory sequence (e.g., a promoter) is a functional link that allows for expression of the polynucleotide of interest (i.e., the polynucleotide of interest is under transcriptional control of the promoter). Operably linked elements may be contiguous or non-contiguous. Coding sequences (e.g., an ORF) can be operably linked to regulatory sequences in sense or antisense orientation. When used to refer to the joining of two protein coding regions, by operably linked is intended that the coding regions are in the same reading frame.

A nucleic acid is "operably linked" when it is placed into a functional relationship with another nucleic acid sequence. For example, DNA encoding a secretory leader (i.e., a signal peptide), is operably linked to DNA for a polypeptide if it is expressed as a pre-protein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous.

Linking is accomplished by ligation at convenient restriction sites. If such sites do not exist, the synthetic oligonucleotide adaptors or linkers are used in accordance with conventional practice.

As used herein, "a functional promoter sequence controlling the expression of a gene of interest (or open reading frame thereof) linked to the gene of interest's protein coding sequence" refers to a promoter sequence which controls the transcription and translation of the coding sequence in *Bacillus*. For example, in certain embodiments, the present disclosure is directed to a polynucleotide comprising a 5' promoter (or 5' promoter region, or tandem 5' promoters and the like), wherein the promoter region is operably linked to a nucleic acid sequence encoding a protein of interest. Thus, in certain embodiments, a functional promoter sequence controls the expression of a gene of interest encoding a protein of interest. In other embodiments, a functional promoter sequence controls the expression of a heterologous gene or an endogenous gene encoding a protein of interest in a *Bacillus* sp. cell.

The promoter sequence consists of proximal and more distal upstream elements, the latter elements often referred to as enhancers. An "enhancer" is a DNA sequence that can stimulate promoter activity, and may be an innate element of the promoter or a heterologous element inserted to enhance the level or tissue-specificity of a promoter.

The linear recombinant DNAs and circular recombinant DNAs disclosed herein can be introduced into a *Bacillus* sp. Cell using any method known in the art.

As defined herein, the term "introducing", as used in phrases such as "introducing into a bacterial cell" or "introducing into a *Bacillus* sp. cell" at least one linear DNA construct, polynucleotide, or a gene thereof, or a vector thereof, includes methods known in the art for introducing DNA constructs into a competent *Bacillus* sp. cell, including, but not limited to mixing the linear DNA construct to be introduced into the *Bacillus* sp. cell with a population of the competent *Bacillus* sp. cells.

"Introducing" is intended to mean presenting to the organism, such as a cell or organism, the linear DNA construct disclosed herein, in such a manner that the component(s) gains access to the interior of a cell of the organism or to the cell itself. The methods and compositions do not depend on a particular method for introducing a sequence into an organism or cell, only that the linear DNA construct disclosed herein gains access to the interior of at least one cell of the organism. Introducing includes reference to the incorporation of a nucleic acid into a competent *Bacillus* sp. cell where the nucleic acid may be incorporated (integrated) into the genome of the cell, and includes reference to the transient (direct) provision of a nucleic acid to the cell.

Stable transformation is intended to mean that the nucleotide construct introduced into an organism integrates into a genome of the organism and is capable of being inherited by the progeny thereof. Transient transformation is intended to mean that a polynucleotide is introduced (directly or indirectly) into the organism and does not integrate into a genome of the organism or a polypeptide is introduced into an organism. Transient transformation indicates that the introduced composition is only temporarily expressed or present in the organism.

A variety of methods are available for identifying those cells with modification of and/or insertion into the genome of *Bacillus* sp. cells. Identification of transformed cells having the desired modification of interest can be determined by any method known to one skilled in the art. For example, identification of *Bacillus* sp. cells having a modification in their genome obtained by the methods described herein can be identified by any phenotypic or genotypic screen known in the art. A screenable phenotype include a phenotypic screen where the presence of a halo around colonies growing on LB agar containing skim milk, indicate the integration of an expression cassette into the genome of the *Bacillus* sp. cells (as described in the examples herein), an antimicrobial susceptibility screen, integration of an expression cassette that results in the hydrolysis of triglycerides in agar resulting in color change of an indicator, integration of an expression cassette that results in the hydrolysis of an indicator substrate that results in a color change, deletion of a gene that influences colony phenotype whereby the difference in colony morphology can be used as genome modification, integration of an expression cassette that results expression of a fluorescent protein, or any one combination thereof.

A screenable genotypic method includes methods for determining the genome sequence of the transformed *Bacillus* sp. cell. Such methods can be viewed as directly analyzing a genomic sequence to detect any change in the genomic nucleotide sequence, including but not limited to PCR methods, sequencing methods, nuclease digestion, Southern blots, and any combination thereof. See, for example, U.S. patent application Ser. No. 12/147,834, herein incorporated by reference to the extent necessary for the methods described herein. The method also comprises recovering an organism from the cell comprising a polynucleotide of interest integrated into its genome. The term "genome", a bacterial (host) cell "genome", or a *Bacillus* (host) cell "genome" includes not only chromosomal DNA found within the nucleus, but organelle DNA found within subcellular components of the cell (extrachromosomal DNA).

As used herein, the terms "plasmid", "vector" and "cassette" refer to extrachromosomal elements, often carrying genes which are typically not part of the central metabolism of the cell, and usually in the form of double-stranded DNA molecules. Such elements may be autonomously replicating sequences, genome integrating sequences, phage or nucleotide sequences, linear or circular, of a single-stranded or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

The term "vector" includes any nucleic acid that can be replicated (propagated) in cells and can carry new genes or DNA segments into cells. Vectors include viruses, bacteriophage, pro-viruses, plasmids, phagemids, transposons, and artificial chromosomes such as BACs (bacterial artificial chromosomes), and the like, that are "episomes" (i.e., replicate autonomously or can integrate into a chromosome of a host organism).

The term "expression cassette" and "expression vector" refer to a nucleic acid construct generated recombinantly or synthetically, with a series of specified nucleic acid elements that permit transcription of a particular nucleic acid in a cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter. In some embodiments, DNA constructs also include a series of specified nucleic acid elements that permit transcription of a particular nucleic acid in a target cell. In certain embodiments, a DNA construct of the disclosure comprises a selective marker and an inactivating chromosomal or gene or DNA segment as defined herein. Many prokaryotic expression vectors are commercially available and know to one skilled in the art. Selection of appropriate expression vectors is within the knowledge of one skilled in the art.

As used herein, a "targeting vector" is a vector that includes polynucleotide sequences that are homologous to a region in the chromosome of a host cell into which the targeting vector is transformed and that can drive homologous recombination at that region. For example, targeting vectors find use in introducing mutations into the chromosome of a host cell through homologous recombination. In some embodiments, the targeting vector comprises other non-homologous sequences, e.g., added to the ends (i.e., stuffer sequences or flanking sequences). The ends can be closed such that the targeting vector forms a closed circle, such as, for example, insertion into a vector. Selection and/or construction of appropriate vectors is well within the knowledge of those having skill in the art.

As used herein, the term "plasmid" refers to a circular double-stranded (ds) DNA construct used as a cloning vector, and which forms an extrachromosomal self-replicating genetic element in many bacteria and some eukaryotes. In some embodiments, plasmids become incorporated into the genome of the host cell.

Polynucleotides of interest are further described herein and include polynucleotides reflective of the commercial markets and interests of those involved in the production of enzymes (such as, but not limiting to, through fermentation of bacteria thereby producing the enzymes.

A polynucleotide of interest can code for one or more proteins of interest. It can have other biological functions. The polynucleotide of interest may or may not already be present in the genome of the *Bacillus* sp. cell to be transformed, i.e., either a homologous or heterologous sequence.

Nucleotides of interest may comprise antisense sequences complementary to at least a portion of the messenger RNA (mRNA) for a targeted gene sequence of interest. Antisense nucleotides are constructed to hybridize with the corresponding mRNA. Modifications of the antisense sequences may be made as long as the sequences hybridize to and interfere with expression of the corresponding mRNA. In this manner, antisense constructions having 70%, 80%, or 85% sequence identity to the corresponding antisense sequences may be used. Furthermore, portions of the antisense nucleotides may be used to disrupt the expression of the target gene. Generally, sequences of at least 50 nucleotides, 100 nucleotides, 200 nucleotides, or greater may be used.

In addition, the polynucleotide of interest may also be used in the sense orientation to suppress the expression of endogenous genes in organisms. Methods for suppressing gene expression in organisms using polynucleotides in the sense orientation are known in the art. The methods generally involve transforming an organism with a DNA construct comprising a promoter that drives expression in an organism operably linked to at least a portion of a nucleotide sequence that corresponds to the transcript of the endogenous gene. Typically, such a nucleotide sequence has substantial sequence identity to the sequence of the transcript of the endogenous gene, generally greater than about 65% sequence identity, about 85% sequence identity, or greater than about 95% sequence identity. See, U.S. Patent Nos. 5,283,184 and 5,034,323; herein incorporated by reference.

A phenotypic marker is a screenable or a selectable marker that includes visual markers and selectable markers whether it is a positive or negative selectable marker. Any phenotypic marker can be used. Specifically, a selectable or screenable marker comprises a DNA segment that allows one to identify, or select for or against a molecule or a cell that contains it, often under particular conditions. These markers can encode an activity, such as, but not limited to, production of RNA, peptide, or protein, or can provide a binding site for RNA, peptides, proteins, inorganic and organic compounds or compositions and the like.

The term "selectable marker" and "selectable marker-encoding nucleotide sequence" refers to a nucleotide sequence which is capable of expression in (host) cells and where expression of the selectable marker confers to cells containing the expressed gene the ability to grow in the presence of a corresponding selective agent or lack of an essential nutrient. In one aspect the selective marker refers to a nucleic acid (e.g., a gene) capable of expression in host cell which allows for ease of selection of those hosts containing the vector. Examples of such selectable markers include, but are not limited to, antimicrobials.

The term "selectable marker" includes genes that provide an indication that a host cell has taken up an incoming DNA of interest or some other reaction has occurred. Typically, selectable markers are genes that confer antimicrobial resistance or a metabolic advantage on the host cell to allow cells containing the exogenous DNA to be distinguished from cells that have not received any exogenous sequence during the transformation.

A "residing selectable marker" is one that is located on the chromosome of the microorganism to be transformed. A residing selectable marker encodes a gene that is different from the selectable marker on the transforming DNA construct. Selective markers are well known to those of skill in the art. As indicated above, the marker can be an antimicrobial resistance marker (e.g., $amp^R$, $phleo^R$, $spec^R$, $kan^R$, $ery^R$, $tet^R$, $cmp^R$ and $neo^R$ (see e.g., Guerot-Fleury, 1995; Palmeros et al., 2000; and Trieu-Cuot et al., 1983). In some embodiments, the present invention provides a chloramphenicol resistance gene (e.g., the gene present on pC194, as well as the resistance gene present in the *Bacillus licheniformis* genome). This resistance gene is particularly useful in the present invention, as well as in embodiments involving chromosomal amplification of chromosomally integrated cassettes and integrative plasmids (See e.g., Albertini and Galizzi, 1985; Stahl and Ferrari, 1984). Other markers useful in accordance with the invention include, but are not limited to auxotrophic markers, such as serine, lysine, tryptophan; and detection markers, such as β-galactosidase.

Polynucleotides of interest includes genes that can be stacked or used in combination with other traits.

As used herein, the terms "polypeptide" and "protein" are used interchangeably, and refer to polymers of any length comprising amino acid residues linked by peptide bonds. The conventional one (1) letter or three (3) letter codes for amino acid residues are used herein. The polypeptide may be linear or branched, it may comprise modified amino acids, and it may be interrupted by non-amino acids. The term polypeptide also encompasses an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

The term "protein of interest" or "POI" refers to a polypeptide of interest that is desired to be expressed in a modified *Bacillus* (daughter) cell. Thus, as used herein, a POI may be an enzyme, a substrate-binding protein, a surface-active protein, a structural protein, a receptor protein, an antibody and the like As used herein, a "gene of interest" or "GOI" refers a nucleic acid sequence (e.g., a polynucleotide, a gene or an ORF) which encodes a POI. A "gene of interest" encoding a "protein of interest" may be a naturally occurring gene, a mutated gene or a synthetic gene.

In certain embodiments, a gene of interest of the instant disclosure encodes a commercially relevant industrial protein of interest, such as an enzyme (e.g., a acetyl esterases, aminopeptidases, amylases, arabinases, arabinofuranosidases, carbonic anhydrases, carboxypeptidases, catalases, cellulases, chitinases, chymosins, cutinases, deoxyribonucleases, epimerases, esterases, α-galactosidases, β-galactosidases, α-glucanases, glucan lysases, endo-β-glucanases, glucoamylases, glucose oxidases, α-glucosidases, β-glucosidases, glucuronidases, glycosyl hydrolases, hemicellulases, hexose oxidases, hydrolases, invertases, isomerases, laccases, lipases, lyases, mannosidases, oxidases, oxidoreductases, pectate lyases, pectin acetyl esterases, pectin depolymerases, pectin methyl esterases, pectinolytic enzymes, perhydrolases, polyol oxidases, peroxidases, phenoloxidases, phytases, polygalacturonases, proteases, peptidases, rhamno-galacturonases, ribonucleases, transferases, transport proteins, transglutaminases, xylanases, hexose oxidases, and combinations thereof).

A "mutation" refers to any change or alteration in a nucleic acid sequence. Several types of mutations exist, including point mutations, deletion mutations, silent mutations, frame shift mutations, splicing mutations and the like. Mutations may be performed specifically (e.g., via site directed mutagenesis) or randomly (e.g., via chemical agents, passage through repair minus bacterial strains).

A "point mutation" described herein refers to a mutation affecting only one or a very few nucleotides in a gene sequence. Point mutations most commonly involve the substitution of one base for another (which changes the complementary base as well in DNA). The term point mutation also includes insertions or deletions of a single base pair. A point mutation or substitution includes a genetic mutation where a single nucleotide base is changed, inserted or deleted from a sequence of DNA or RNA.

Methods are described herein to introduce mutations into the genome of a competent *Bacillus* sp. cell.

In one embodiment, the method is a method for introducing a mutation into the genome of a *Bacillus* sp. cell without the use of a selectable marker, the method comprising providing a population of competent *Bacillus* sp. cells and introducing a linear DNA construct into at least one *Bacillus* sp. cell of said population of cells, wherein said DNA construct comprises a nucleotide sequence having the desired mutation flanked by an upstream homology arm (HR1) and a downstream homology arm (HR2), wherein each homology arm is at least 900 nucleotides in length, and wherein said DNA construct does not comprise a selectable marker. In one embodiment, the above method further comprising growing progeny cells from said at least one *Bacillus* sp. cell on media that do not comprise a selectable marker, and identifying a *Bacillus* sp. progeny cell that has mutation in its genome. In one aspect, the nucleotide sequence having the desired mutation comprises of at least 1, 2, 3, 4, 5, 6, 7, 8, 9, or 10 base modifications or substitutions compared to the native sequence of the *Bacillus* sp. cell (genomic *Bacillus* sp. DNA sequence prior to the modification). In one aspect, the nucleotide sequence having the desired mutation (base substitutions) consists of 1, 2, 3, 4, 5, 6, 7, 8, 9, or 10 bases.

In one aspect of the disclosure, the donor DNA comprises a nucleotide sequence having the desired mutation flanked by two homology arms (one 5' upstream arm, HR1, and one 3' downstream arm HR2) of at least 900 nucleotides in length. Once this donor construct is introduced into the cell, homologous recombination can occur which results in mutation of the original genome sequence.

A "mutated gene" is a gene that has been altered through human intervention. Such a "mutated gene" has a sequence that differs from the sequence of the corresponding non-mutated gene by at least one nucleotide addition, deletion, or substitution. In certain embodiments of the disclosure, the mutated gene comprises an alteration that results from the methods as disclosed herein. A mutated cell or organism is a cell or organism comprising a mutated gene.

As used herein, in the context of a polypeptide or a sequence thereof, the term "substitution" means the replacement (i.e., substitution) of one amino acid with another amino acid.

As defined herein, an "endogenous gene" refers to a gene in its natural location in the genome of an organism.

As used herein, "heterologous" in reference to a polynucleotide or polypeptide sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide. As used herein, unless otherwise specified, a chimeric polynucleotide comprises a coding sequence operably linked to a transcription initiation region that is heterologous to the coding sequence.

As defined herein, a "heterologous" gene, a "non-endogenous" gene, or a "foreign" gene refer to a gene (or ORF) not normally found in the host organism, but that is introduced into the host organism by gene transfer. As used herein, the term "foreign" gene(s) comprise native genes (or ORFs) inserted into a non-native organism and/or chimeric genes inserted into a native or non-native organism.

As defined herein, a "heterologous" nucleic acid construct or a "heterologous" nucleic acid sequence has a portion of the sequence which is not native to the cell in which it is expressed.

As defined herein, a "heterologous control sequence", refers to a gene expression control sequence (e.g., a promoter or enhancer) which does not function in nature to regulate (control) the expression of the gene of interest. Generally, heterologous nucleic acid sequences are not endogenous (native) to the cell, or a part of the genome in which they are present, and have been added to the cell, by infection, transfection, transformation, microinjection, electroporation, and the like. A "heterologous" nucleic acid construct may contain a control sequence/DNA coding (ORF) sequence combination that is the same as, or different, from a control sequence/DNA coding sequence combination found in the native host cell.

As used herein, the terms "signal sequence" and "signal peptide" refer to a sequence of amino acid residues that may participate in the secretion or direct transport of a mature protein or precursor form of a protein. The signal sequence is typically located N-terminal to the precursor or mature protein sequence. The signal sequence may be endogenous or exogenous. A signal sequence is normally absent from the mature protein. A signal sequence is typically cleaved from the protein by a signal peptidase after the protein is transported.

The term "derived" encompasses the terms "originated" "obtained," "obtainable," and "created," and generally indicates that one specified material or composition finds its origin in another specified material or composition, or has features that can be described with reference to the another specified material or composition.

As used herein, a "flanking sequence" refers to any sequence that is either upstream or downstream of the sequence being discussed (e.g., for genes A-B-C, gene B is flanked by the A and C gene sequences). In certain embodiments, the incoming sequence is flanked by a homology arm on each side. In some embodiments, a flanking sequence is present on only a single side (either 3' or 5'), while in other embodiments, it is on each side of the sequence being flanked. The sequence of each homology arm is homologous to a sequence in the *Bacillus* sp. genome (such as the *Bacillus* chromosome).

As used herein, the term "stuffer sequence" refers to any extra DNA that flanks homology arms (typically vector sequences). However, the term encompasses any non-homologous DNA sequence. Not to be limited by any theory, a stuffer sequence provides a non-critical target for a cell to initiate DNA uptake.

Sequence identity" or "identity" in the context of nucleic acid or polypeptide sequences refers to the nucleic acid bases or amino acid residues in two sequences that are the same when aligned for maximum correspondence over a specified comparison window.

The term "percentage of sequence identity" refers to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. Useful examples of percent sequence identities include, but are not limited to, 50%, 55%, 60%, 65%, 70%, 75%, 80%, 85%, 90% or 95%, or any integer percentage from 50% to 100%. These identities can be determined using any of the programs described herein. Sequence alignments and percent identity or similarity calculations may be determined using a variety of comparison methods designed to detect homologous sequences including, but not limited to, the MegAlign™ program of the LASERGENE bioinformatics computing suite (DNASTAR Inc., Madison, Wis.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

The "Clustal V method of alignment" corresponds to the alignment method labeled Clustal V (described by Higgins and Sharp, (1989) *CABIOS* 5:151-153; Higgins et al., (1992) *Comput Appl Biosci* 8:189-191) and found in the MegAlign™ program of the LASERGENE bioinformatics computing suite (DNASTAR Inc., Madison, Wis.). For multiple alignments, the default values correspond to GAP PENALTY=10 and GAP LENGTH PENALTY=10. Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program.

The "Clustal W method of alignment" corresponds to the alignment method labeled Clustal W (described by Higgins and Sharp, (1989) *CABIOS* 5:151-153; Higgins et al., (1992) *Comput Appl Biosci* 8:189-191) and found in the MegAlign™ v6.1 program of the LASERGENE bioinformatics computing suite (DNASTAR Inc., Madison, Wis.). Default parameters for multiple alignment (GAP PENALTY=10, GAP LENGTH PENALTY=0.2, Delay Divergen Seqs (%)=30, DNA Transition Weight=0.5, Protein Weight Matrix=Gonnet Series, DNA Weight Matrix=IUB). After alignment of the sequences using the Clustal W program, it is possible to obtain a "percent identity" by viewing the "sequence distances" table in the same program.

Unless otherwise stated, sequence identity/similarity values provided herein refer to the value obtained using GAP Version 10 (GCG, Accelrys, San Diego, Calif.) using the following parameters: % identity and % similarity for a nucleotide sequence using a gap creation penalty weight of 50 and a gap length extension penalty weight of 3, and the nwsgapdna.cmp scoring matrix; % identity and % similarity for an amino acid sequence using a GAP creation penalty weight of 8 and a gap length extension penalty of 2, and the BLOSUM62 scoring matrix (Henikoff and Henikoff, (1989) *Proc. Natl. Acad. Sci. USA* 89:10915). GAP uses the algorithm of Needleman and Wunsch, (1970) *J Mol Biol* 48:443-53, to find an alignment of two complete sequences that maximizes the number of matches and minimizes the number of gaps. GAP considers all possible alignments and gap positions and creates the alignment with the largest number of matched bases and the fewest gaps, using a gap creation penalty and a gap extension penalty in units of matched bases.

"BLAST" is a searching algorithm provided by the National Center for Biotechnology Information (NCBI) used to find regions of similarity between biological sequences. The program compares nucleotide or protein sequences to sequence databases and calculates the statistical significance of matches to identify sequences having sufficient similarity to a query sequence such that the similarity would not be predicted to have occurred randomly. BLAST reports the identified sequences and their local alignment to the query sequence.

It is well understood by one skilled in the art that many levels of sequence identity are useful in identifying polypeptides from other species or modified naturally or synthetically wherein such polypeptides have the same or similar function or activity. Useful examples of percent identities include, but are not limited to, 50%, 55%, 60%, 65%, 70%, 75%, 80%, 85%, 90% or 95%, or any integer percentage from 50% to 100%. Indeed, any integer amino acid identity from 50% to 100% may be useful in describing the present disclosure, such as $51^{0/6, 52}$%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%.

"Translation leader sequence" refers to a polynucleotide sequence located between the promoter sequence of a gene and the coding sequence. The translation leader sequence is present in the mRNA upstream of the translation start sequence. The translation leader sequence may affect processing of the primary transcript to mRNA, mRNA stability or translation efficiency. Examples of translation leader sequences have been described (e.g., Turner and Foster, (1995) *Mol Biotechnol* 3:225-236).

"3' non-coding sequences", "transcription terminator" or "termination sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., (1989) *Plant Cell* 1:671-680.

As used herein, "RNA transcript" refers to the product resulting from RNA polymerase-catalyzed transcription of a DNA sequence. When the RNA transcript is a perfect complimentary copy of the DNA sequence, it is referred to as the primary transcript or pre-mRNA. A RNA transcript is referred to as the mature RNA or mRNA when it is a RNA sequence derived from post-transcriptional processing of the primary transcript pre-mRNA. "Messenger RNA" or "mRNA" refers to the RNA that is without introns and that can be translated into protein by the cell. "cDNA" refers to a DNA that is complementary to, and synthesized from, an mRNA template using the enzyme reverse transcriptase. The cDNA can be single-stranded or converted into double-stranded form using the Klenow fragment of DNA polymerase I. "Sense" RNA refers to RNA transcript that includes the mRNA and can be translated into protein within a cell or in vitro. "Antisense RNA" refers to an RNA transcript that is complementary to all or part of a target primary transcript or mRNA, and that blocks the expression of a target gene (see, e.g., U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that may not be translated but yet has an effect on cellular processes. The terms "complement" and "reverse complement" are used interchangeably herein with respect to mRNA transcripts, and are meant to define the antisense RNA of the message.

"Mature" protein refers to a post-translationally processed polypeptide (i.e., one from which any pre- or propeptides present in the primary translation product have been removed). "Precursor" protein refers to the primary product of translation of mRNA (i.e., with pre- and propeptides still present). Pre- and propeptides may be but are not limited to intracellular localization signals.

Proteins may be altered in various ways including amino acid substitutions, deletions, truncations, and insertions. Methods for such manipulations are generally known. For example, amino acid sequence variants of the protein(s) can be prepared by mutations in the DNA. Methods for mutagenesis and nucleotide sequence alterations include, for example, Kunkel, (1985) *Proc. Natl. Acad. Sci. USA* 82:488-92; Kunkel et al., (1987) *Meth Enzymol* 154:367-82; U.S. Pat. No. 4,873,192; Walker and Gaastra, eds. (1983) *Techniques in Molecular Biology* (MacMillan Publishing Company, New York) and the references cited therein. Guidance regarding amino acid substitutions not likely to affect biological activity of the protein is found, for example, in the model of Dayhoff et al., (1978) *Atlas of Protein Sequence and Structure* (Natl Biomed Res Found, Washington, D.C.). Conservative substitutions, such as exchanging one amino acid with another having similar properties, may be preferable. Conservative deletions, insertions, and amino acid substitutions are not expected to produce radical changes in the characteristics of the protein, and the effect of any substitution, deletion, insertion, or combination thereof can be evaluated by routine screening assays.

Standard DNA isolation, purification, molecular cloning, vector construction, and verification/characterization methods are well established, see, for example Sambrook et al., (1989) *Molecular Cloning: A Laboratory Manual*, (Cold Spring Harbor Laboratory Press, NY). Vectors and constructs include circular plasmids, and linear polynucleotides, comprising a polynucleotide of interest and optionally other components including linkers, adapters, regulatory or analysis. In some examples a nucleotide of interest can be contained within an intron, coding sequence, 5' UTRs, 3' UTRs, and/or regulatory regions.

The meaning of abbreviations is as follows: "sec" means second(s), "min" means minute(s), "h" means hour(s), "d" means day(s), "μL" means microliter(s), "mL" means milliliter(s), "L" means liter(s), "μM" means micromolar, "mM" means millimolar, "M" means molar, "mmol" means millimole(s), "μmole" mean micromole(s), "g" means gram(s), "μg" means microgram(s), "ng" means nanogram(s), "U" means unit(s), "bp" means base pair(s) and "kb" means kilobase(s).

Non-limiting embodiments of compositions and methods disclosed herein are as follows:

1. A method for integrating a donor DNA into the genome of a *Bacillus* sp. cell without the use of a selectable marker, the method comprising providing a population of competent *Bacillus* sp. cells and introducing a linear DNA construct into at least one *Bacillus* sp. cell of said population of cells, wherein said DNA construct comprises a donor DNA flanked by an upstream homology arm (HR1) and a downstream homology arm (HR2), wherein each homology arm is 900 nucleotides in length, or greater than 900 nucleotides in length, wherein said DNA construct does not comprise a selectable marker.

2. A method for integrating a donor DNA into the genome of a *Bacillus* sp. cell without the use of a selectable marker, the method comprising providing a population of competent *Bacillus* sp. cells and introducing a linear DNA construct into at least one *Bacillus* sp. cell of said population of cells, wherein said DNA construct comprises a donor DNA flanked by an upstream homology arm (HR1) and a downstream homology arm (HR2), wherein each homology arm is at least 900 nucleotides in length, wherein said DNA construct does not comprise a selectable marker.

3. A method for deleting a nucleotide sequence in the genome of a *Bacillus* sp. cell without the use of a selectable marker, the method comprising providing a population of competent *Bacillus* sp. cells, and introducing a linear DNA construct into at least one *Bacillus* sp. cell of said population of cells, wherein said DNA construct comprises an upstream homology arm (HR1) and a downstream homology arm (HR2), wherein each homology arm is at least 900 nucleotides in length and has sequence homology to a genomic DNA region flanking the nucleotide sequence to be deleted, wherein said DNA construct does not comprise a selectable marker.

4. A method for deleting a nucleotide sequence in the genome of a *Bacillus* sp. cell without the use of a selectable marker, the method comprising providing a population of competent *Bacillus* sp. cells, and introducing a linear DNA construct into at least one *Bacillus* sp. cell of said population of cells, wherein said DNA construct consists of an upstream homology arm (HR1) and a downstream homology arm (HR2), wherein each homology arm is at least 900 nucleotides in length and has sequence homology to a genomic DNA region flanking said nucleotide sequence to be deleted, wherein said DNA construct does not comprise a selectable marker.

5. The method of any of embodiments 1-4, wherein each homology arm is at least 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 5000, 6000 nucleotides and up to 7000 nucleotides in length.

6. The method of any of embodiments 1-4, wherein the linear DNA construct is a double strand DNA.

7. The method of any of embodiments 1-4, wherein the competent *Bacillus* sp. cell is selected from the group consisting of *Bacillus subtilis, Bacillus licheniformis, Bacillus lentus, Bacillus brevis, Bacillus stearothermophilus, Bacillus alkalophilus, Bacillus amyloliquefaciens, Bacillus clausii, Bacillus. halodurans, Bacillus. megaterium, Bacillus coagulans, Bacillus circulans, Bacillus lautus,* and *Bacillus thuringiensis.*

8. The method of any of embodiments 1-4, wherein said competent *Bacillus* sp. cells were made competent by at least one copy of an introduced nucleic acid construct comprising a promoter operably linked to a polynucleotide encoding a polypeptide selected from the group consisting of ComK, ComS or any one combination thereof.

9. The method of any of embodiments 1-4, wherein said competent *Bacillus* sp. cells are from a super-competent *Bacillus* sp. strain.

10. The method of embodiment 7, wherein said super-competent *Bacillus* sp. strain is a Pxyl-ComK strain.

11. The method of embodiment 1 or 2, wherein the donor DNA comprises a nucleotide sequence selected from the group consisting of a polynucleotide of interest, a gene of interest, multiple copies of a gene of interest, one or more recombinant DNAs, a transcriptional regulatory sequence, a translational regulatory sequence, a promoter sequence, a terminator sequence, a transgenic nucleic acid sequence, an antisense sequence complementary to at least a portion of the messenger RNA, a heterologous sequence, a nucleotide sequence comprising a point muta- tion to be introduced into the genome, or any one com- bination thereof.

12. The method of embodiment 1 or 2, further comprising growing progeny cells from said at least one *Bacillus* sp. cell on media that do not comprise a selectable marker, and identifying a *Bacillus* sp. progeny cell that has the donor DNA sequence stably integrated in its genome.

13. The method of embodiment 3 or 4, further comprising growing progeny cells from said at least one *Bacillus* sp. cell on media that do not comprise a selectable marker, and identifying a *Bacillus* sp. progeny cell that has the nucleotide sequence deleted from its genome.

14. The method of embodiment 3 or 4, wherein the linear DNA construct further comprises a donor DNA flanked by said upstream homology arm (HR1) and downstream homology arm (HR2), wherein said donor DNA is inserted in the genome of said *Bacillus* sp. cell while said nucleotide sequence is deleted in said genome of said *Bacillus* sp. cell.

15. The method of embodiment 14, further comprising growing progeny cells from said at least one *Bacillus* sp. cell on media that do not comprise a selectable marker, and identifying a *Bacillus* sp. progeny cell that has the nucleotide sequence deleted from its genome and had the donor DNA integrated into its genome.

16. A method for introducing a mutation into the genome of a *Bacillus* sp. cell without the use of a selectable marker, the method comprising providing a population of com- petent *Bacillus* sp. cells and introducing a linear DNA construct into at least one *Bacillus* sp. cell of said popu- lation of cells, wherein said DNA construct comprises a nucleotide sequence having the desired mutation flanked by an upstream homology arm (HR1) and a downstream homology arm (HR2), wherein said single base of said DNA construct is different from the corresponding single base in the genome of said at least one *Bacillus* sp., and wherein each homology arm is at least 1200 nucleotides in length, wherein said DNA construct does not comprise a selectable marker.

17. The method of embodiment 16, further comprising growing progeny cells from said at least one *Bacillus* sp. cell on media that do not comprise a selectable marker, and identifying a *Bacillus* sp. progeny cell that has the single base mutation in its genome.

18. The method of claim 16, wherein the nucleotide sequence having the desired mutation comprises of at least 1, 2, 3, 4, 5, 6, 7, 8, 9, or 10 base modifications or substitutions.

19. The method of claim 16, wherein the nucleotide sequence having the desired mutation consists of 1, 2, 3, 4, 5, 6, 7, 8, 9, or 10 bases.

EXAMPLES

The disclosed disclosure is further defined in the follow- ing Examples. It should be understood that these Examples, while indicating certain preferred aspects of the disclosure, are given by way of illustration only. From the above discussion and these Examples, one skilled in the art can ascertain the essential characteristics of this disclosure, and without departing from the spirit and scope thereof, can make various changes and modifications of the disclosure to adapt it to various uses and conditions.

Example 1

Integration of Linear Donor DNA into the Chromosome of *Bacillus subtilis* without Selection This example described the assembly and subsequent transformation of a linear DNA construct comprised of a donor DNA (encoding a gene of interest) flanked by homol- ogy regions (HR1-aprE and HR2-aprE) and the frequency of integration into the chromosome of *Bacillus subtilis* cells induced for expression of ComK. The genes of interest (GOIs) are a lipase and a protease.

Linear DNA constructs were amplified from genomic DNA as follows. The first construct encoding HR1-aprE1 (SEQ ID NO: 1), a lipase from *Proteus vulgaris* (SEQ ID NO: 2) the BPN' terminator (SEQ ID NO: 3) and HR2- aprE1 (SEQ ID NO: 4) was amplified by PCR using oligos (SEQ ID NO: 5) and (SEQ ID NO: 6) yielding product (SEQ ID NO: 7). The second construct encoding HR1- aprE2 (SEQ ID NO: 8), the P2 promoter (SEQ ID NO: 9), the protease from *Bacillus gibsonii* (SEQ ID NO: 10), the BPN' terminator (SEQ ID NO: 3) and HR2-aprE2 (SEQ ID NO: 11) was amplified by PCR using oligos (SEQ ID NO: 12) and (SEQ ID NO: 13) yielding product (SEQ ID NO: 14).

These synthetic linear DNA constructs for integration of a donor DNA encoding a lipase (SEQ ID NO: 7) or a protease (SEQ ID NO: 14) were transformed into *Bacillus subtilis* (*B. subtilis*) as follows. *B. subtilis* cells containing the *B. subtilis* comK gene (SEQ ID NO: 15) introduced at the amyE locus using the PxylA inducible promoter for expression, were grown overnight at 37° C. and 250 RPM in 15 ml of L broth (1% $w \cdot v^{-1}$ Tryptone, 0.5% Yeast extract $w \cdot v^{-1}$, 1% NaCl $w \cdot v^{-1}$), in a 125 ml baffled flask. The overnight culture was diluted to 0.2 ($OD_{600}$ units) in 10 ml fresh L broth in a one hundred twenty-five (125) ml baffle flask. Cells were grown until the culture reached 0.9 ($OD_{600}$ units) at 37° C. (250 RPM). D-xylose was added to 0.1% (w/v) from a 10% (w/v) stock. Cells were grown for an additional 2 hours at 37° C. (250 RPM) and then 4 ml of 50% glycerol in 0.5X L-broth was added, mixed and saved at −80° C. until ready for transformation. Transformations were prepared by adding 100 ng of (SEQ ID NO: 7) and (SEQ ID NO: 14) DNA to 100 µl of competent cells, incubated at 37C 1000 RPM for 1 hour followed by dilution of the cells 10 fold by adding 900 µl LB (this is $10^{-1}$ dilution). Cells were diluted additional 10 fold four times to $10^{-5}$. 100 µl from dilutions $10^{-4}$ and $10^{-5}$ were then plated onto either Rhodamine Olive oil Agar (ROA) for (SEQ ID NO: 7) or LB agar containing 1.6% Skim Milk for (SEQ ID NO: 14). Plates were incubated overnight at 37° C. Cells expressing lipase appear as pink colonies with dark pink halos on ROA while the parent cells appear as white colonies. Cells expressing protease form a clear halo on LB-Skim milk agar.

To determine the frequency of integration of the donor DNA encoding the lipase, the percentage of pink colonies grown non-selectively on ROA were scored (Table 1). The presence of a halo around colonies on the non-selective LB agar containing skim mild was used to determine the fre- quency of protease integration. As shown in Table 1 46% of colonies were found to contain halos indicating protease integration.

TABLE 1

| | | | | |
|---|---|---|---|---|
| Frequency of integration of donor DNA without selection | | | | |
| | SEQ ID NO | Genomic locus | Homology arm length in bp (HR1) | Homology arm length in bp (HR2) | Frequency of integration (%) |
| No DNA | na | na | na | na | 0 |
| Lipase integration | 7 | aprE | 3275 | 2912 | 31 |
| Protease integration | 14 | aprE | 2965 | 2971 | 46 |

Example 2

Integration of Linear Donor DNAs into the Chromosome of *Bacillus subtilis* Using Linear DNA Constructs Comprising Varying Lengths of Homology Arms and without Selection This example described the assembly and subsequent transformation of linear DNA constructs comprised of a donor DNA (encoding a gene of interest) flanked by homology regions of varying lengths, and the frequency of integration into the chromosome of *Bacillus subtilis* cells induced for expression of ComK.

The DNA construct comprising a donor DNA for integration of a lipase at the aprE locus (SEQ ID NO: 7) and protease (SEQ ID NO: 14) were used as a template for PCR to amplify products with homology arms of varying lengths. The template, primers, and HR1 and HR2 homology lengths are listed in Table 2.

TABLE 2

| | | | | | |
|---|---|---|---|---|---|
| Construction of donor DNA with varying length HR | | | | | |
| Template | F primer | R primer | Product | HR1 (bp) | HR2 (bp) |
| SEQ ID NO: 7 | SEQ ID NO: 16 | SEQ ID NO: 17 | SEQ ID NO: 22 | 336 | 755 |
| SEQ ID NO: 7 | SEQ ID NO: 18 | SEQ ID NO: 19 | SEQ ID NO: 23 | 1200 | 1681 |
| SEQ ID NO: 7 | SEQ ID NO: 18 | SEQ ID NO: 13 | SEQ ID NO: 24 | 1200 | 2971 |
| SEQ ID NO: 7 | SEQ ID NO: 12 | SEQ ID NO: 19 | SEQ ID NO: 25 | 3265 | 1681 |
| SEQ ID NO: 7 | SEQ ID NO: 5 | SEQ ID NO: 6 | SEQ ID NO: 26 | 3275 | 2912 |
| SEQ ID NO: 7 | SEQ ID NO: 12 | SEQ ID NO: 20 | SEQ ID NO: 27 | 3265 | 6095 |
| SEQ ID NO: 7 | SEQ ID NO: 16 | SEQ ID NO: 20 | SEQ ID NO: 28 | 336 | 6095 |
| SEQ ID NO: 14 | SEQ ID NO: 21 | SEQ ID NO: 17 | SEQ ID NO: 29 | 289 | 755 |
| SEQ ID NO: 14 | SEQ ID NO: 18 | SEQ ID NO: 19 | SEQ ID NO: 30 | 900 | 1681 |
| SEQ ID NO: 14 | SEQ ID NO: 18 | SEQ ID NO: 13 | SEQ ID NO: 31 | 900 | 2971 |
| SEQ ID NO: 14 | SEQ ID NO: 12 | SEQ ID NO: 19 | SEQ ID NO: 32 | 2965 | 1681 |
| SEQ ID NO: 14 | SEQ ID NO: 12 | SEQ ID NO: 13 | SEQ ID NO: 33 | 2965 | 2971 |

The linear donor DNA constructs described above (SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 and SEQ ID NO: 33) were transformed into *B. subtilis* as follows. *B. subtilis* cells containing the *B. subtilis* comK gene (SEQ ID NO: 15) introduced at the amyE locus using the PxylA inducible promoter for expression, were grown overnight at 37° C. and 250 RPM in 15 ml of L broth (1% w·v$^{-1}$ Tryptone, 0.5% Yeast extract w·v$^{-1}$, 1% NaCl w·v$^{-1}$), in a 125 ml baffled flask. The overnight culture was diluted to 0.2 (OD$_{600}$ units) in 10 ml fresh L broth in a one hundred twenty-five (125) ml baffle flask. Cells were grown until the culture reached 0.9 (OD$_{600}$ units) at 37° C. (250 RPM). D-xylose was added to 0.1% (w/v) from a 10% (w/v) stock. Cells were grown for an additional 2 hours at 37° C. (250

RPM) and then 4 ml of 50% glycerol in 0.5X L-broth was added, mixed and saved at −80° C. until ready for transformation. Transformations were prepared by adding 80 ng DNA to 100 µl of competent cells, incubated at 37C 1000 RPM for 1 hour followed by dilution of the cells 10 fold by adding 900 µl LB (this is 10$^{-1}$ dilution). Cells were diluted additional 10 fold four times to 10$^{-5}$. 100 µl from dilutions 10$^{-3}$, 10$^{-4}$ and 10$^{-5}$ were then plated onto LB agar. Plates were incubated overnight at 37° C.

To determine the frequency of integration of the donor DNA encoding the lipase, the percentage of pink colonies grown non-selectively on ROA were scored (Table 3). The presence of a halo around colonies on the non-selective LB agar containing skim mild was used to determine the frequency of protease integration. As shown in Table 3, homology arm length of less than 900 bp did not yield high frequency integration.

TABLE 3

Frequency of integration of donor DNA without selection requires long homology arms

| | SEQ ID NO | Genomic locus | Homology arm length in bp (HR1) | Homology arm length in bp (HR2) | Frequency of integration (%) |
|---|---|---|---|---|---|
| NO DNA | na | na | na | na | 0 |
| Integration | SEQ ID NO: 22 | aprE | 336 | 755 | 0 |
| Integration | SEQ ID NO: 23 | aprE | 1200 | 1681 | 1 |
| Integration | SEQ ID NO: 24 | aprE | 1200 | 2971 | 2 |
| Integration | SEQ ID NO: 25 | aprE | 3265 | 1681 | 10 |
| Integration | SEQ ID NO: 26 | aprE | 3275 | 2912 | 32 |
| Integration | SEQ ID NO: 27 | aprE | 3265 | 6095 | 37 |
| Integration | SEQ ID NO: 28 | aprE | 336 | 6095 | 0 |
| Integration | SEQ ID NO: 29 | aprE | 289 | 755 | 0 |
| Integration | SEQ ID NO: 30 | aprE | 900 | 1681 | 5 |
| Integration | SEQ ID NO: 31 | aprE | 900 | 2971 | 2 |
| Integration | SEQ ID NO: 32 | aprE | 2965 | 1681 | 9 |
| Integration | SEQ ID NO: 33 | aprE | 2965 | 2971 | 28 |

Example 3

Marker Free Deletions and Point Mutations into the Chromosome of *Bacillus subtilis* Using Linear DNA Constructs Comprising Varying Lengths of Homology Arms and without Selection This example described the assembly and subsequent transformation of linear DNA constructs comprising homology regions of about 3 kb in length for generating deletions and point mutation, and the frequency of deletion or point mutation into the chromosome of *Bacillus subtilis* cells induced for expression of ComK.

For deletion of the skf locus in *B. subtilis,* a linear DNA construct (SEQ ID NO: 34) was amplified by PCR which contains the HR1-skf (SEQ ID NO: 35) and HR2-skf (SEQ ID NO: 36) sequences.

For deletion of the lipA gene locus in *B. subtilis,* a linear DNA construct (SEQ ID NO: 37) was amplified by PCR which contains the HR1-lipA (SEQ ID NO: 38) and the HR2-lipA (SEQ ID NO: 39) sequences.

To introduce an amino acid change of S79 into an integrated copy of the Proteus HR2 lipase (SEQ ID NO: 40) in the *B. subtilis* genome a mutagenic PCR strategy was used. First the genomic sequences (SEQ ID NO: 41) encoding the lipase driven by the synthetic P4 promoter (SEQ ID NO: 42) was used as template for PCR with forward primer (SEQ ID NO: 12) and reverse primer (SEQ ID NO: 43) to generate SEQ ID NO: 44. Next, sequence SEQ ID NO: 41 was used as template for PCR with forward primer (SEQ ID NO: 45) and reverse primer (SEQ ID NO: 46) to generate SEQ ID NO: 47. To generate the final linear DNA construct, 10 ng of both fragments were mixed together and incubated at 98° C. 30 sec, 24 cycles of 98° C. 10 sec, 70 ° C. (−0.5/cycle) 30 sec, 72° C. 3.5 min, followed by 72° C. for 3 min. The resulting product was amplified by PCR using oligos (SEQ ID NO: 12) and (SEQ ID NO: 13) yielding the linear DNA construct of SEQ ID NO: 48.

The linear DNA constructs (SEQ ID NO: 34), (SEQ ID NO: 37) and (SEQ ID NO: 48) were transformed into *B. subtilis* as follows. *B. subtilis* cells containing the *B. subtilis* comK gene (SEQ ID NO: 15) introduced at the amyE locus using the PxylA inducible promoter for expression, were grown overnight at 37° C. and 250 RPM in 15 ml of L broth (1% w·v$^{-1}$ Tryptone, 0.5% Yeast extract w·v$^{-1}$, 1% NaCl w·v$^{-1}$), in a 125 ml baffled flask. The overnight culture was diluted to 0.2 ($OD_{600}$ units) in 10 ml fresh L broth in a one hundred twenty-five (125) ml baffle flask. Cells were grown until the culture reached 0.9 ($OD_{600}$ units) at 37° C. (250 RPM). D-xylose was added to 0.1% (w/v) from a 10% (w/v) stock. Cells were grown for an additional 2 hours at 37° C. (250 RPM) and then 4 ml of 50% glycerol in 0.5X L-broth was added, mixed and saved at −80° C. until ready for transformation. Transformations were prepared by adding 100 ng of DNA to 100 μl of competent cells, incubated at 37C 1000 RPM for 1 hour followed by dilution of the cells 10 fold by adding 900 μl LB (this is $10^{-1}$ dilution). Cells were diluted additional 10 fold four times to $10^{-5}$. 100 μl from dilutions $10^{-3}$, $10^{-4}$ and $10^{-5}$ were then plated onto either LB agar for deletion of skf (SEQ ID NO: 34), or Rhodamine Olive oil Agar (ROA) for deletion of lipA (SEQ ID NO: 37) and lipase point mutation (SEQ ID NO: 48). Plates were incubated overnight at 37° C.

To determine the frequency of skf deletion the DNA from colonies was amplified by PCR using primers specific for the skf locus in *B. subtilis.* Primers (SEQ ID NO: 49) and (SEQ ID NO: 50) generate a 1200 bp product if the skf locus is successfully deleted. Colony PCR of transformants found that 31° A of all colonies had a deletion of the skf locus (Table 4).

The frequency of deletion of the *B. subtilis* lipA gene or the point mutation in the heterologous lipase was determined by the frequency of white colonies on ROA plates. For deletion of lipA, 25% of colonies were found to be white and for the point mutation 32% were white (Table 4). Examples of the white colonies for each transformation were further verified to contain deletion or point mutation by amplifying the chromosomal region and looking for the expected size change for the deletion and by sequencing the site of the point mutation.

TABLE 4

High frequency of deletion and point mutations without selection

| | SEQ ID NO | Genomic locus | Homology arm length in bp (HR1) | Homology arm length in bp (HR2) | Frequency of integration (%) |
|---|---|---|---|---|---|
| No DNA | na | na | na | na | 0 |
| skf deletion | 16 | skf | 3006 | 3032 | 31 |
| lipA deletion | 19 | lipA | 3040 | 3047 | 25 |
| Lipase point | 27 | aprE | 2965 | 2971 | 32 |

TABLE 4-continued

High frequency of deletion and point mutations without selection

| SEQ ID NO | Genomic locus | Homology arm length in bp (HR1) | Homology arm length in bp (HR2) | Frequency of integration (%) | 5 |
|---|---|---|---|---|---| mutation

What is claimed:

1. A method for integrating a donor DNA into the genome of a *Bacillus* sp. cell without introducing a nuclease that introduces a double strand break into the genome, and without introducing any circular recombinant DNA, the method comprising providing a population of competent *Bacillus* sp. cells and introducing only a linear DNA construct into at least one *Bacillus* sp. cell of said population of cells, wherein said DNA construct comprises a donor DNA flanked by an upstream homology arm (HR1) and a downstream homology arm (HR2), wherein each homology arm is at least 900 nucleotides in length, wherein said DNA construct does not comprise a selectable marker and no selection agent is applied during or after transformation.

2. The method of claim 1, wherein each homology arm is at least 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 5000, 6000 nucleotides and up to 7000 nucleotides in length.

3. The method of claim 1, wherein the linear DNA construct is a double strand DNA.

4. The method of claim 1, wherein the competent *Bacillus* sp. cell is selected from the group consisting of *Bacillus subtilis, Bacillus licheniformis, Bacillus lentus, Bacillus brevis, Bacillus stearothermophilus, Bacillus alkalophilus, Bacillus amyloliquefaciens, Bacillus clausii, Bacillus halodurans, Bacillus megaterium, Bacillus coagulans, Bacillus circulans, Bacillus lautus,* and *Bacillus thuringiensis.*

5. The method of claim 1, wherein said competent *Bacillus* sp. cells were made competent by at least one copy of an introduced nucleic acid construct comprising a promoter operably linked to a polynucleotide encoding a polypeptide selected from the group consisting of ComK, ComS or any one combination thereof.

6. The method of claim 1, wherein the donor DNA comprises a nucleotide sequence selected from the group consisting of a recombinant DNA, a transcriptional regulatory sequence, a translational regulatory sequence, a promoter sequence, a terminator sequence, a transgenic nucleic acid sequence, an antisense sequence complementary to at least a portion of a messenger RNA, a heterologous sequence, a nucleotide sequence comprising 1-10 defined base substitutions or any one combination thereof.

7. The method of claim 1, further comprising growing progeny cells from said at least one *Bacillus* sp. cell on media that do not comprise a selection agent, and identifying a *Bacillus* sp. progeny cell that has the donor DNA sequence stably integrated in its genome.

8. A method for deleting a nucleotide sequence in the genome of a *Bacillus* sp. cell without introducing a nuclease that introduces a double strand break into the genome, and without introducing any circular recombinant DNA, the method comprising providing a population of competent *Bacillus* sp. cells and introducing only a linear DNA construct into at least one *Bacillus* sp. cell of said population of cells, wherein said DNA construct comprises an upstream homology arm (HR1) and a downstream homology arm (HR2), wherein each homology arm is at least 900 nucleotides in length and has sequence homology to a genomic DNA region flanking said nucleotide sequence to be deleted, wherein said DNA construct does not comprise a selectable marker and no selection agent is applied during or after transformation.

9. The method of claim 8, further comprising growing progeny cells from said at least one *Bacillus* sp. cell on media that do not comprise a selection agent, and identifying a *Bacillus* sp. progeny cell that has the nucleotide sequence deleted from its genome.

10. The method of claim 8, wherein the linear DNA construct further comprises a donor DNA flanked by said upstream homology arm (HR1) and downstream homology arm (HR2), wherein said donor DNA is inserted in the genome of said *Bacillus* sp. cell while said nucleotide sequence is deleted in said genome of said *Bacillus* sp. cell.

11. The method of claim 10, further comprising growing progeny cells from said at least one *Bacillus* sp. cell on media that do not comprise a selective agent of the selectable marker, and identifying a *Bacillus* sp. progeny cell that has the nucleotide sequence deleted from its genome and has the donor DNA integrated into its genome.

12. The method of claim 2, wherein each homology arm is at least 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 5000, 6000 nucleotides and up to 7000 nucleotides in length.

13. The method of claim 8, wherein the linear DNA construct is a double strand DNA.

14. The method of claim 8, wherein the competent *Bacillus* sp. cell is selected from the group consisting of *Bacillus subtilis, Bacillus licheniformis, Bacillus lentus, Bacillus brevis, Bacillus stearothermophilus, Bacillus alkalophilus, Bacillus amyloliquefaciens, Bacillus clausii, Bacillus halodurans, Bacillus megaterium, Bacillus coagulans, Bacillus circulans, Bacillus lautus*, and *Bacillus thuringiensis.*

15. The method of claim 8, wherein said competent *Bacillus* sp. cells were made competent by at least one copy of an introduced nucleic acid construct comprising a promoter operably linked to a polynucleotide encoding a polypeptide selected from the group consisting of ComK, ComS or any one combination thereof.

16. A method for introducing a mutation in the genome of a *Bacillus* sp. cell without introducing a nuclease that introduces a double strand break into the genome, and without introducing any circular recombinant DNA, the method comprising providing a population of competent *Bacillus* sp. cells and introducing only a linear DNA construct into at least one *Bacillus* sp. cell of said population of cells, wherein said DNA construct comprises a nucleotide sequence having the desired mutation flanked by an up stream homology arm (HR1) and a downstream homology arm (HR2), and wherein each homology arm is at least 900 nucleotides in length, wherein said DNA construct does not comprise a selectable marker and no selection agent is applied during or after transformation.

17. The method of claim 14, further comprising growing progeny cells from said at least one *Bacillus* sp. cell on media that do not comprise a selection agent, and identifying a *Bacillus* sp. progeny cell that has the mutation in its genome.

\* \* \* \* \*

SEQUENCE LISTING

<160> NUMBER OF SEQ ID NOS: 50

<210> SEQ ID NO 1
<211> LENGTH: 3275
<212> TYPE: DNA
<213> ORGANISM: Bacillus subtilis

<400> SEQUENCE: 1

```
ccctgctgac agaaatatcc ggcggtgacc cggagcttca aagcacccgt ctcgtcaacg      60
cctgcctcag caacattgaa tttgcagaag aaaaatggcg gataaaagac tataatatca     120
acagccactt atccggcttt atcaaataag aaaaagacag gcgtttgcct gtctttttctt     180 ttatttctta gcagccggca tctctttttg aagctcgtcc aaaatggcat tcgccccgtc     240
tacactgcgg cgcagagacc acaccgcacg atccacgtgg tatacatgcc cgttttttcac     300 tgccttcagt tttttccaaa ggacattctt ttcgatcggg cgtttaccgt cggcgtcgag     360
gtcatctgtt tttcctgtca tcaggatgat cacatccgga tctgttttca gcagctgctc     420
cagtgtcatt ttcatattca cagagtcgcc gccattgctt gaatcgctat tgcctgacgt     480
actgattgca tatcggtagc cgacctgtgt taaaagtctc gatgtaaaga agttttcatc     540
cctggccata atggtatcat ttgtatttcc gatcaaaagc acggactggc tgttcgcgct     600
gattttctgc tttgtctcgc taagcttttc ttcatgcgcc gtcagctttt tctccatttc     660
cttctccttg ccgactgctt ttgcaatcgt aagcgaagcg tcaattgtat cctgataatc     720
agcatttaaa ttattaagtg caatcgtcgg cgctattttt ttcagctgat cgtacacctt     780
cttatgccgg gtcgtgtcag caataattaa atcgggtttt aatgaagcga tttttttccat     840 gcttggctgt gagcgagtgc cgacagatgt gtagccgtca attttcttca gcacatcctt     900
gttgatcagc tgcttcgctt tgttgtcatc ggcaacccccg acaggcgtaa tgccgagatc     960
aagcagtgta tcaataaaac ctagctcaag aacaacaacc cgcttcggat gctcaggcac    1020
atttgtcttc cctaaatcat gtgttaccgc cactttatgt tctttactgt tttgattgcc    1080
gcttgaagac gagcaagcag ccgttaagac agaaagaagt aaaactgtaa gaataatcag    1140 tgttttttttc atatgttcca gtctctcctg ttggtagttt ctatggttaa gatgtccaag    1200
agtagtataa cacggaatga gaatcattat caccaattat tttttaaaatg agaagagaaa    1260 gttcggctta caggaaaatc ttgtttcgcg acacagcagt tcagcagctg atcatcctgt    1320
ccacaaaaaa gcttgcagaa aaataacatt ctctgcaagc tgatcctgtt aaagcttcac    1380
aatcactctt ccttgaatgc gattttgcaa aatatctttt aacgcacccg gcgtttcttc    1440
caatgatact tccctgtcca cgatggtcag cagctgatca ggcttgagat cagaagacat    1500
gcgctcccaa acagcggctc tgacgtccat cggacaatat actgaatcga ttccgagcag    1560
gcttactccg cgaagaataa aaggatacac ggttgccgga acttctcctc cgccggttaa    1620
gccgctcact gcgacagatc cgccgtattg aattttgctt aaaagcgagg caagctgttt    1680
```

-continued

```
tccgccgact ggatcaaccg ctccctgcca ttgctgcttg gacagcgcct taagcgttcc    1740
gtcatagaca tcttccctgc tgattacttc gcttgcacca agctgtttca aataatcagc    1800
cgcctcccgg tttccggtac ttgccaccac atcataaccc cgcttgttca gcatcgatac    1860
cgcaattccg ccgacaccgc cggttgctcc tgtgactagc acgctgcctt tttccggaga    1920
cagaccgttc tgttcaagcc gatgcactga taacgccgca gtaaatcccg ccgttccgta    1980
caccatcgct tcttttaacg aaagattctg tggcaaaggc accagccagt caccaggcac    2040
cgaagcgtat tcacttaatc cgccatcacg tgagacaccg agctcatagc ttgtcgcgat    2100
cacctcatcc ccctccgcaa aacgcggatc attggaagag acgaccgtac ccgcagcatc    2160
aatgcctaaa ataagcggat actctctgac gatattgcct cctgcttttc cggccagacc    2220
atctttgtaa ttaatgccgg aataagcaac tttaatcagg acaccatcct tcggcaaatc    2280
ctctgttgat atggttttca catggactga aacatcatcg gcattttttt ctgcctgcaa    2340
ggcttgaaat aacgttgaca ttcggcacac tcctttttcat ttatatcgta accgaagaac    2400
gttcaaaaaa ccaaatcatc aagccgccat tttcacttcg ccggcacatt gagacaataa    2460
tggacaaatc cggtatcctc ttcatagccg tttgctcat acaagcttct tgccttccgg     2520
ttgtggtgct cagtctgaag tgttaaacat tttgccccgt tttgccctgc ataatccttt    2580
gcggcagaaa gcagccggcc gccggctccc tttgtacgcg catgaggaac gacaaataag    2640
tcatttaata tgtatatcct tttcattgac acagaagaaa acgttggata gagctgggta    2700
aagcctatga attctccatt ttcttctgct atcaaaataa cagactcgtg attttccaaa    2760
cgagctttca aaaaagcctc tgccccttgc aaatcggatg cctgtctata aaattcccga    2820
tattggttaa acagcggcgc aatggcggcc gcatctgatg tctttgcttg gcgaatgttc    2880
atcttatttc ttcctccctc tcaataattt tttcattcta tccctttct gtaaagttta     2940 tttttcagaa tacttttatc atcatgcttt gaaaaaatat cacgataata tccattgttc    3000
tcacggaagc acacgcaggt catttgaacg aatttttcg acaggaattt gccgggactc      3060
aggagcattt aacctaaaaa agcatgacat ttcagcataa tgaacattta ctcatgtcta    3120
ttttcgttct tttctgtatg aaaatagtta tttcgagtct ctacggaaat agcgagagat    3180
gatataccta aatagagata aaatcatctc aaaaaaatgg gtctactaaa atattattcc    3240
atctattaca ataaattcac agaatagtct tttaa                                3275
```

<210> SEQ ID NO 2
<211> LENGTH: 864
<212> TYPE: DNA
<213> ORGANISM: artificial sequence
<220> FEATURE:
<223> OTHER INFORMATION: synthesized sequence -Optimized coding sequence
      for Proteus vulgaris (WP099659650.1) lipase

<400> SEQUENCE: 2

```
gtgtcaacaa catatcctat tgtcctggta cacggccttt ctggtttcga tgacatcgta     60
ggataccctt atttttatgg gattgccgac gccctggaga aagatggcca caaagttttt    120
acagcctcac tctctgcatt caattccaac gaagtccgtg gcgagcaatt atgggagttc    180
gtgcaaaaga ttctcaaaga gactaaagca aaaaaggtga atttgatcgg cactcccaa     240 ggtcctcttg cgtgtcgtta tgtggcggcc aagcatgcta aaagtattgc aagtgttaca    300
tctgtgaatg gagtgaatca cggtagcgaa atcgccgatc ttgtcagacg gattatgaga    360
aaagattctg tccctgagta tatcgcggac gcggtaatga aggctattgg cactataatc    420
```

-continued

```
agtactttta gcggaaatag aggaaaccct caagacgcta tagcagctct ggaggcctta        480
acgacggaaa acgtgatgga atttaacaaa aaatatcctc agggactgcc agcaattcgt        540
gggggtgaag gtaaagaagt cgtgaacggc gtacactact atagctttgg ttcttacata        600
cagggtctca tcgctggcga aagggaaac ttgctcgatc ctacccacgc cgctatgcgc         660
gttttatccg cgtttttttc agaacgtgag aacgatggtt tagtaggacg gacttcaatg        720
cggctcggca agttaattaa agacgactac gctgaggatc atttagatat ggtcaatcaa        780
gttgcggggt tagttggacg cggggaggat ataattgcta tatatacgaa tcatgccaat        840 ttttagcgt caaaaaagct ctaa                                               864

<210> SEQ ID NO 3
<211> LENGTH: 254
<212> TYPE: DNA
<213> ORGANISM: Bacillus amyloliquefaciens

<400> SEQUENCE: 3
tctagataca taaaaaccg gccttggccc cgccggtttt ttattatttt tcttcctccg         60
catgttcaat ccgctccata atcgacggat ggctccctct gaaaatttta acgagaaacg        120
gcgggttgac ccggctcagt cccgtaacgg ccaagtcctg aaacgtctca atcgccgctt        180
cccggtttcc ggtcagctca atgccgtaac ggtcggcggc gttttcctga taccgggaga        240
cggcattcgt aatc                                                         254

<210> SEQ ID NO 4
<211> LENGTH: 2912
<212> TYPE: DNA
<213> ORGANISM: Bacillus subtilis

<400> SEQUENCE: 4
aacgcctcac tcctcacatc aacccgttac ttctattgta atcataaatt caaattctta         60
gaaccaagct gtgttccgca ctttttccacc cttttaagca tggaaacccc gatcgctggg       120
aaaactaaca atgtttggag tgatgcaaat gaaaaaaata gtggcagcca tcgtggtaat        180
cggtcttgtg tttatcgcat ttttttatct ttacagccga tcaggcgatg tgtatcaatc        240
ggtagacgcg gatttgatca cactgtcttc aagcggccag gaagatatcg agattgaaaa        300
aagacagcac gtcaaagata tgctggatat tatgaatcag ggaaaacagg tgaagacaga        360
aaaaacatca gccctgatt acgaagggac aatcaagttt cataaagacc ggtatgactc        420
attcagacta tggattgacg gcagccagca agccgttttt ttgaaggatg gcacatacta        480
caaattaagc aaaaatgata caaaggcgct gctaaatatt attaaaaaag aagcaaagga        540
ttgaaaatga aaaagcgaag ctaaccgctt cgctttttca ttttattggg gcaaaatatc        600
tctcagtgcc cgtctgagca ttttccccgt cgcatttttc ggaatatcgt caagaaacgt        660
aatggcggga ggccgcttgt attttgccag atgcttttcg cagtgctgca tgatgtcctc        720
ctctgttacc ccagagcgtt tcggcaccac atatcccttt accgcttccc cgctttgggg       780
gtccggcacg ccgatgacaa ccgcctcctt gacgtccgga tggctgtaca gcacctcctc        840
cacctcccgc ggatacacat tgtatcctcc tacaatgatc atgtcttttt tccggtcaac        900
aatgtaaaaa tagccgtcct catcccgtct tgccaagtcc cccgtataaa gccacccgtc        960
ttttaatgca tgctctgttt ccatcggcat tttataatag cccttcatca cattggggcc       1020
tttcacgatc aattcgccga cctggtgagc gggcagctcg cgtccgagcg gatctacgac      1080
```

-continued

```
cttgttttcg acatgtaaga tacttgtccc gatggagccc ggctttctgc ccctgtcaaa       1140
cgggttaaag cacgtgacgg gtgatgcttc cgagagcccg tagccttcca aaatggtaac       1200
accgaatttt tcttcaaacg ccgtcagcaa cgcgactggc atggacgcgc ctcccgaaat       1260
gcacagccgg atcgaagaaa aatcatcttt ctttccgttt tcatgctgaa acaagtagtt       1320
atacattgta ggcacaccgg caaaaatggt cgcctgctgc tgcttaacaa gcttaaaaac       1380
agatgccgga ctgaattgag gctcaatcaa tacagttgcg ccgctcatca gcggtgcatt       1440
catacagacg gttaaacaaa acacgtgaaa catgggaaga gcgcagacca cattgtccct       1500
ctcatccatt cccaaatagc ctgcgacatc gttggcattg ctgtacaaat tctgatgtgt       1560
cagcatcgcg cctttcggtt ttccagtcgt tcctgacgta tataaaataa ccgcggtatc       1620
atcaggtaca ggttcttggt tttgtttagc ggcagatgtc ggccgcaata tttttgcaaa       1680
cgttgtcatt ttcatcctga cctctgggtc cgcagcttcc ggctcggcct cccccgtctg       1740
gcataaaatg acgagctcaa cctttggcag cgattcatgc atgctctcat aaagcggcaa       1800
aagctggcta acgcccacga ttgcctttac atcgccattt gtcagcatat aaccaatttc       1860
tgtcggcgtg tacaacggat tgatgggaac aactacgatc ccagctttta aagcgccaaa       1920
aaacgcgatg ataaaatcag gcgaattgcc aagcagcaaa gctaaatggt cccctttctc       1980
cataccggct tcctgaaggc cgtccgcaaa tcgctgaata tattcattca gctcttgata       2040
cgtcatcatg tgatctttaa acctgcatgc gatgctgtcg ggcttctcag atgctgtttc       2100
ttccaatttt gaaacaagat tcattctccc accccttaag tgaatgaata gtcattcatt       2160
attgaagcca agctttcttc tccattatag agaaacagaa aaaaacactc aagagcaaaa       2220
agccctgagt gtcagtactg tcatagtttc ttcaatgctt cggcaatcgg cgtatctcct       2280
tctgtcagat caaaggcccg attttccgta ttcttctcat ctaaagaggc aatgaccgtt       2340
tttgcaacgt catcacggga aataaatccc cgctccagat ccttcgctgc tgaaacagtt       2400
cccgttccag gctcattgcg aaggcctccc ggacggataa tcgtataggt taaaccgctc       2460
gcttccagaa ttttatcagc ataatgcttg gccacataat aaggcttgag tgcctcattc       2520
caattttcac ggttatgggc ttgcagggcg ctgaccataa taaaccgttt gattccggca       2580
atggccgcag cttcaatggc ttttgccgct ccatcaagat ccaccagcag cgttttatca       2640
tagcctgtgc tgccgccgga accggctgtg aaaatgatcg cgtcacaacc ttttgccgca       2700
gcggcgattt cttccgggct gccctccaga ttcgcaagca cagcttctgc accggcagct       2760
tcaagagacg ctttctgttc ttcttttctg accatcgctc tgatggaatg atcaggatta       2820
tcttggaata aagagacgag tctttgcccg atttgtccgt tcgctccgat taaaaacact       2880
ttcatgtgaa tccctcctgc ctccattatt tc                                     2912
```

```
<210> SEQ ID NO 5
<211> LENGTH: 25
<212> TYPE: DNA
<213> ORGANISM: artificial sequence
<220> FEATURE:
<223> OTHER INFORMATION: synthesized sequence - F primer

<400> SEQUENCE: 5
ccctgctgac agaaatatcc ggcgg                                                25

<210> SEQ ID NO 6
<211> LENGTH: 21
<212> TYPE: DNA
<213> ORGANISM: artificial sequence
```

<220> FEATURE:
<223> OTHER INFORMATION: synthesized sequence - R primer

<400> SEQUENCE: 6
gaaataatgg aggcaggagg g                                                    21

<210> SEQ ID NO 7
<211> LENGTH: 7346
<212> TYPE: DNA
<213> ORGANISM: artificial sequence
<220> FEATURE:
<223> OTHER INFORMATION: synthesized sequence - HR1-aprE, aprE promoter,
      Proteus vulgaris lipase, BPNprime terminator, HR2-aprE

<400> SEQUENCE: 7
ccctgctgac agaaatatcc ggcggtgacc cggagcttca aagcacccgt ctcgtcaacg      60
cctgcctcag caacattgaa tttgcagaag aaaaatggcg gataaaagac tataatatca     120
acagccactt atccggcttt atcaaataag aaaaagacag gcgtttgcct gtcttttctt     180
ttatttctta gcagccggca tctctttttg aagctcgtcc aaaatggcat tcgccccgtc     240
tacactgcgg cgcagagacc acaccgcacg atccacgtgg tatacatgcc cgttttttcac    300 tgccttcagt ttttttccaaa ggacattctt ttcgatcggg cgtttaccgt cggcgtcgag    360
gtcatctgtt tttcctgtca tcaggatgat cacatccgga tctgtttttca gcagctgctc    420 cagtgtcatt ttcatattca cagagtcgcc gccattgctt gaatcgctat tgcctgacgt     480
actgattgca tatcggtagc cgacctgtgt taaaagtctc gatgtaaaga agttttcatc     540
cctggccata atggtatcat ttgtatttcc gatcaaaagc acggactggc tgttcgcgct     600
gattttctgc tttgtctcgc taagctttt ttcatgcgcc gtcagctttt tctccatttc      660
cttctccttg ccgactgctt ttgcaatcgt aagcgaagcg tcaattgtat cctgataatc     720
agcatttaaa ttattaagtg caatcgtcgg cgctattttt ttcagctgat cgtacacctt     780
cttatgccgg gtcgtgtcag caataattaa atcgggtttt aatgaagcga ttttttccat     840
gcttggctgt gagcgagtgc cgacagatgt gtagccgtca attttcttca gcacatcctt     900
gttgatcagc tgcttcgctt tgttgtcatc ggcaaccccg acaggcgtaa tgccgagatc     960
aagcagtgta tcaataaaac ctagctcaag aacaacaacc cgcttcggat gctcaggcac    1020
atttgtcttc cctaaatcat gtgttaccgc cactttatgt tctttactgt tttgattgcc    1080
gcttgaagac gagcaagcag ccgttaagac agaaagaagt aaaactgtaa gaataatcag    1140 tgttttttttc atatgttcca gtctctcctg ttggtagttt ctatggttaa gatgtccaag    1200
agtagtataa cacggaatga gaatcattat caccaattat ttttaaaatg agaagagaaa    1260
gttcggctta caggaaaatc ttgtttcgcg cacacagcagt tcagcagctg atcatcctgt    1320
ccacaaaaaa gcttgcagaa aaataacatt ctctgcaagc tgatcctgtt aaagcttcac    1380
aatcactctt ccttgaatgc gattttgcaa aatatctttt aacgcacccg gcgtttcttc    1440
caatgatact tccctgtcca cgatggtcag cagctgatca ggcttgagat cagaagacat    1500
gcgctcccaa acagcggctc tgacgtccat cggacaatat actgaatcga ttccgagcag    1560
gcttactccg cgaagaataa aaggatacac ggttgccgga acttctcctc cgccggttaa    1620
gccgctcact gcgacagatc cgccgtattg aattttgctt aaaagcgagg caagctgttt    1680
tccgccgact ggatcaaccg ctccctgcca ttgctgcttg acagcgcct taagcgttcc     1740 gtcatagaca tcttccctgc tgattacttc gcttgcacca agctgtttca aataatcagc    1800
cgcctcccgg tttccggtac ttgccaccac atcataaccc cgcttgttca gcatcgatac    1860

```
cgcaattccg ccgacaccgc cggttgctcc tgtgactagc acgctgcctt tttccggaga   1920
cagaccgttc tgttcaagcc gatgcactga taacgccgca gtaaatcccg ccgttccgta   1980
caccatcgct tcttttaacg aaagattctg tggcaaaggc accagccagt caccaggcac   2040
cgaagcgtat tcacttaatc cgccatcacg tgagacaccg agctcatagc ttgtcgcgat   2100
cacctcatcc ccctccgcaa aacgcggatc attggaagag acgaccgtac ccgcagcatc   2160
aatgcctaaa ataagcggat actctctgac gatattgcct cctgctttc cggccagacc    2220 atctttgtaa ttaatgccgg aataagcaac tttaatcagg acaccatcct tcggcaaatc   2280
ctctgttgat atggttttca catggactga aacatcatcg gcattttttt ctgcctgcaa   2340
ggcttgaaat aacgttgaca ttcggcacac tccttttcat ttatatcgta accgaagaac   2400
gttcaaaaaa ccaaatcatc aagccgccat tttcacttcg ccggcacatt gagacaataa   2460
tggacaaatc cggtatcctc ttcatagccg ttttgctcat acaagcttct tgccttccgg   2520
ttgtggtgct cagtctgaag tgttaaacat tttgcccgt tttgccctgc ataatccttt    2580
gcggcagaaa gcagccggcc gccggctccc tttgtacgcg catgaggaac gacaaataag   2640
tcatttaata tgtatatcct tttcattgac acagaagaaa acgttggata gagctgggta   2700
aagcctatga attctccatt ttcttctgct atcaaaataa cagactcgtg attttccaaa   2760
cgagctttca aaaagcctc tgcccccttgc aaatcggatg cctgtctata aaattcccga   2820
tattggttaa acagcggcgc aatggcggcc gcatctgatg tctttgcttg gcgaatgttc   2880
atcttatttc ttcctccctc tcaataattt tttcattcta tcccttttct gtaaagttta   2940
tttttcagaa tactttatc atcatgcttt gaaaaaatat cacgataata tccattgttc    3000
tcacggaagc acacgcaggt catttgaacg aattttttcg acaggaattt gccgggactc   3060
aggagcattt aacctaaaaa agcatgacat ttcagcataa tgaacattta ctcatgtcta   3120
ttttcgttct tttctgtatg aaaatagtta tttcgagtct ctacggaaat agcgagagat   3180
gatatatcca aatagagata aaatcatctc aaaaaaatgg gtctactaaa atattattcc   3240
atctattaca ataaattcac agaatagtct tttaagtaag tctactctga attttttaa    3300 aaggagaggg taaagagtgt caacaacata tcctattgtc ctggtacacg gccttttctgg  3360 tttcgatgac atcgtaggat acccttattt ttatgggatt gccgacgccc tggagaaaga   3420
tggccacaaa gttttttacag cctcactctc tgcattcaat tccaacgaag tccgtggcga  3480
gcaattatgg gagttcgtgc aaaagattct caaagagact aaagcaaaaa aggtgaattt   3540
gatcgggcac tcccaaggtc ctcttgcgtg tcgttatgtg gcggccaagc atgctaaaag   3600
tattgcaagt gttacatctg tgaatggagt gaatcacggt agcgaaatcg ccgatcttgt   3660
cagacggatt atgagaaaag attctgtccc tgagtatatc gcggacgcgg taatgaaggc   3720
tattggcact ataatcagta cttttagcgg aaatagagga aaccctcaag acgctatagc   3780
agctctggag gccttaacga cggaaaacgt gatggaattt aacaaaaaat atcctcaggg   3840
actgccagca attcgtgggg gtgaaggtaa agaagtcgtg aacggcgtac actactatag   3900
ctttggttct tacatacagg gtctcatcgc tggcgagaag ggaaacttgc tcgatcctac   3960
ccacgccgct atgcgcgttt tatccgcgtt ttttttcagaa cgtgagaacg atggtttagt  4020
aggacggact tcaatgcggc tcggcaagtt aattaaagac gactacgctg aggatcattt   4080
agatatggtc aatcaagttg cggggttagt tggacgcggg gaggatataa ttgctatata   4140
tacgaatcat gccaattttt tagcgtcaaa aaagctctaa tctagataca taaaaaaccg   4200
```

-continued

```
gccttggccc cgccggtttt ttattatttt tcttcctccg catgttcaat ccgctccata      4260
atcgacggat ggctccctct gaaaatttta acgagaaacg gcgggttgac ccggctcagt      4320
cccgtaacgg ccaagtcctg aaacgtctca atcgccgctt cccggtttcc ggtcagctca      4380
atgccgtaac ggtcggcggc gttttcctga taccgggaga cggcattcgt aatcaacgcc      4440
tcactcctca catcaacccg ttacttctat tgtaatcata aattcaaatt cttagaacca      4500
agctgtgttc cgcacttttc caccctttta agcatggaaa ccccgatcgc tgggaaaact      4560
aacaatgttt ggagtgatgc aaatgaaaaa aatagtggca gccatcgtgg taatcggtct      4620
tgtgtttatc gcattttttt atctttacag ccgatcaggc gatgtgtatc aatcggtaga      4680
cgcggatttg atcacactgt cttcaagcgg ccaggaagat atcgagattg aaaaaagaca      4740
gcacgtcaaa gatatgctgg atattatgaa tcagggaaaa caggtgaaga cagaaaaaac      4800
atcagcccct gattacgaag ggacaatcaa gtttcataaa gaccggtatg actcattcag      4860
actatggatt gacggcagcc agcaagccgt ttttttgaag gatggcacat actacaaatt      4920
aagcaaaaat gatacaaagg cgctgctaaa tattattaaa aaagaagcaa aggattgaaa      4980
atgaaaaagc gaagctaacc gcttcgcttt ttcattttat tggggcaaaa tatctctcag      5040
tgcccgtctg agcattttcc ccgtcgcatt tttcggaata tcgtcaagaa acgtaatggc      5100
ggcaggccgc ttgtattttg ccagatgctt ttcgcagtgc tgcatgatgt cctcctctgt      5160
taccccagag cgtttcggca ccacatatcc ctttaccgct tccccgcttt ggggtccgg      5220 cacgccgatg acaaccgcct ccttgacgtc cggatggctg tacagcacct cctccacctc      5280
ccgcggatac acattgtatc ctcctacaat gatcatgtct ttttccggt caacaatgta      5340 aaaatagccg tcctcatccc gtcttgccaa gtcccccgta taaagccacc cgtctttaa      5400 tgcatgctct gtttccatcg gcattttata atagcccttc atcacattgg ggcctttcac      5460
gatcaattcg ccgacctggt gagcgggcag ctcgcgtccg agcggatcta cgaccttgtt      5520
ttcgacatgt aagatacttg tcccgatgga gcccggcttt ctgcccctgt caaacgggtt      5580
aaagcacgtg acgggtgatg cttccgagag cccgtagcct tccaaaatgg taacaccgaa      5640 ttttcttca aacgccgtca gcaacgcgac tggcatggac gcgcctcccg aaatgcacag      5700
ccggatcgaa gaaaaatcat ctttctttcc gtttttcatgc tgaaacaagt agttatacat      5760
tgtaggcaca ccggcaaaaa tggtcgcctg ctgctgctta acaagcttaa aaacagatgc      5820
cggactgaat tgaggctcaa tcaatacagt tgcgccgctc atcagcggtg cattcataca      5880
gacggttaaa caaaacacgt gaaacatggg aagagcgcag accacattgt ccctctcatc      5940
cattcccaaa tagcctgcga catcgttggc attgctgtac aaattctgat gtgtcagcat      6000
cgcgcctttc ggttttccag tcgttcctga cgtatataaa ataaccgcgg tatcatcagg      6060
tacaggttct tggttttgtt tagcggcaga tgtcggccgc aatattttg caaacgttgt      6120 cattttcatc ctgacctctg ggtccgcagc ttccggctcg gcctcccccg tctggcataa      6180
aatgacgagc tcaaccttg gcagcgattc atgcatgctc tcataaagcg gcaaaagctg      6240
gctaacgccc acgattgcct ttacatcgcc atttgtcagc atataaccaa tttctgtcgg      6300
cgtgtacaac ggattgatgg gaacaactac gatcccagct tttaaagcgc caaaaaacgc      6360
gatgataaaa tcaggcgaat tgccaagcag caaagctaaa tggtcccctt tctccatacc      6420
ggcttcctga aggccgtccg caaatcgctg aatatattca ttcagctctt gatacgtcat      6480
catgtgatct ttaaacctgc atgcgatgct gtcgggcttc tcagatgctg tttcttccaa      6540
ttttgaaaca agattcattc tcccaccct taagtgaatg aatagtcatt cattattgaa      6600
```

```
gccaagcttt cttctccatt atagagaaac agaaaaaaac actcaagagc aaaaagccct   6660
gagtgtcagt actgtcatag tttcttcaat gcttcggcaa tcggcgtatc tccttctgtc   6720
agatcaaagg cccgattttc cgtattcttc tcatctaaag aggcaatgac cgttttttgca   6780 acgtcatcac gggaaataaa tccccgctcc agatccttcg ctgctgaaac agttcccgtt   6840
ccaggctcat tgcgaaggcc tcccggacgg ataatcgtat aggttaaacc gctcgcttcc   6900
agaattttat cagcataatg cttggccaca taataaggct tgagtgcctc attccaattt   6960
tcacggttat gggcttgcag ggcgctgacc ataataaacc gtttgattcc ggcaatggcc   7020
gcagcttcaa tggcttttgc cgctccatca agatccacca gcagcgtttt atcatagcct   7080
gtgctgccgc cggaaccggc tgtgaaaatg atcgcgtcac aaccttttgc cgcagcggcg   7140
atttcttccg ggctgccctc cagattcgca agcacagctt ctgcaccggc agcttcaaga   7200
gacgctttct gttcttcttt tctgaccatc gctctgatgg aatgatcagg attatcttgg   7260
aataaagaga cgagtctttg cccgatttgt ccgttcgctc cgattaaaaa cactttcatg   7320
tgaatccctc ctgcctccat tatttc                                        7346

<210> SEQ ID NO 8
<211> LENGTH: 2965
<212> TYPE: DNA
<213> ORGANISM: Bacillus subtilis

<400> SEQUENCE: 8
tcgtcaacgc ctgcctcagc aacattgaat ttgcagaaga aaaatggcgg ataaaagact     60
ataatatcaa cagccactta tccggcttta tcaaataaga aaaagacagg cgtttgcctg    120
tcttttcttt tatttcttag cagccggcat ctctttttga agctcgtcca aaatggcatt    180
cgccccgtct acactgcggc gcagagacca caccgcacga tccacgtggt atacatgccc    240
gtttttcact gccttcagtt ttttccaaag gacattcttt tcgatcgggc gtttaccgtc    300
ggcgtcgagg tcatctgttt ttcctgtcat caggatgatc acatccggat ctgtttttcag    360 cagctgctcc agtgtcattt tcatattcac agagtcgccg ccattgcttg aatcgctatt    420
gcctgacgta ctgattgcat atcggtagcc gacctgtgtt aaaagtctcg atgtaaagaa    480
gttttcatcc ctggccataa tggtatcatt tgtatttccg atcaaaagca cggactggct    540
gttcgcgctg attttctgct ttgtctcgct aagcttttct tcatgcgccg tcagcttttt    600
ctccatttcc ttctccttgc cgactgcttt tgcaatcgta agcgaagcgt caattgtatc    660
ctgataatca gcatttaaat tattaagtgc aatcgtcggc gctattttt tcagctgatc    720 gtacaccttc ttatgccggg tcgtgtcagc aataattaaa tcgggtttta atgaagcgat    780
tttttccatg cttggctgtg agcgagtgcc gacagatgtg tagccgtcaa ttttcttcag    840
cacatccttg ttgatcagct gcttcgcttt gttgtcatcg gcaaccccga caggcgtaat    900
gccgagatca agcagtgtat caataaaacc tagctcaaga acaacaaccc gcttcggatg    960
ctcaggcaca tttgtcttcc ctaaatcatg tgttaccgcc actttatgtt ctttactgtt   1020
ttgattgccg cttgaagacg agcaagcagc cgttaagaca gaaagaagta aaactgtaag   1080
aataatcagt gttttttttca tatgttccag tctctcctgt tggtagtttc tatggttaag   1140
atgtccaaga gtagtataac acggaatgag aatcattatc accaattatt tttaaaatga   1200
gaagagaaag ttcggcttac aggaaaaatct tgtttcgcga cacagcagtt cagcagctga   1260
tcatcctgtc cacaaaaaag cttgcagaaa aataacattc tctgcaagct gatcctgtta   1320
```

-continued

```
aagcttcaca atcactcttc cttgaatgcg attttgcaaa atatctttta acgcacccgg      1380
cgtttcttcc aatgatactt ccctgtccac gatggtcagc agctgatcag gcttgagatc      1440
agaagacatg cgctcccaaa cagcggctct gacgtccatc ggacaatata ctgaatcgat      1500
tccgagcagg cttactccgc gaagaataaa aggatacacg gttgccggaa cttctcctcc      1560
gccggttaag ccgctcactg cgacagatcc gccgtattga attttgctta aaagcgaggc      1620
aagctgtttt ccgccgactg gatcaaccgc tccctgccat tgctgcttgg acagcgcctt      1680
aagcgttccg tcatagacat cttccctgct gattacttcg cttgcaccaa gctgtttcaa      1740
ataatcagcc gcctcccggt ttccggtact tgccaccaca tcataacccc gcttgttcag      1800
catcgatacc gcaattccgc cgacaccgcc ggttgctcct gtgactagca cgctgccttt      1860
ttccggagac agaccgttct gttcaagccg atgcactgat aacgccgcag taaatcccgc      1920
cgttccgtac accatcgctt cttttaacga aagattctgt ggcaaaggca ccagccagtc      1980
accaggcacc gaagcgtatt cacttaatcc gccatcacgt gagacaccga gctcatagct      2040
tgtcgcgatc acctcatccc cctccgcaaa acgcggatca ttggaagaga cgaccgtacc      2100
cgcagcatca atgcctaaaa taagcggata ctctctgacg atattgcctc ctgctttttcc      2160 ggccagacca tctttgtaat taatgccgga ataagcaact ttaatcagga caccatcctt      2220
cggcaaatcc tctgttgata tggttttcac atggactgaa acatcatcgg cattttttc       2280 tgcctgcaag gcttgaaata acgttgacat tcggcacact cctttcatt tatatcgtaa       2340 ccgaagaacg ttcaaaaaac caaatcatca agccgccatt ttcacttcgc cggcacattg      2400
agacaataat ggacaaatcc ggtatcctct tcatagccgt tttgctcata caagcttctt      2460
gccttccggt tgtggtgctc agtctgaagt gttaaacatt ttgccccgtt ttgccctgca      2520
taatcctttg cggcagaaag cagccggccg ccggctccct ttgtacgcgc atgaggaacg      2580
acaaataagt catttaatat gtatatcctt ttcattgaca cagaagaaaa cgttggatag      2640
agctgggtaa agcctatgaa ttctccattt tcttctgcta tcaaaataac agactcgtga      2700
ttttccaaac gagctttcaa aaaagcctct gccccttgca aatcggatgc ctgtctataa      2760
aattcccgat attggttaaa cagcggcgca atggcggccg catctgatgt ctttgcttgg      2820
cgaatgttca tcttatttct tcctccctct caataatttt ttcattctat cccttttctg      2880
taaagtttat ttttcagaat actttatca tcatgctttg aaaaaatatc acgataatat       2940
ccattgttct cacggaagca cacgc                                           2965
```

```
<210> SEQ ID NO 9
<211> LENGTH: 94
<212> TYPE: DNA
<213> ORGANISM: artificial sequence
<220> FEATURE:
<223> OTHER INFORMATION: synthesized sequence- P2 promoter

<400> SEQUENCE: 9
gctgataaac agctgacatc aactaaaagt ttcattaaat actttgaaaa aagttgttga      60
cttaaaagaa gctaaatgtt atagtaattg taca                                   94

<210> SEQ ID NO 10
<211> LENGTH: 339
<212> TYPE: DNA
<213> ORGANISM: Bacillus gibonsii

<400> SEQUENCE: 10
gtgagaagca aaaaattgtg gatcagcttg ttgtttgcgt taacgttaat ctttacgatg      60
```

-continued

```
gcgttcagca acatgtctgc gcaggctgct gaagaagcaa aagaaaaata tttaattggc      120
tttaatgagc aggaagctgt cagtgagttt gtagaacaag tagaggcaaa tgacgaggtc      180
gccattctct ctgaggaaga ggaagtcgaa attgaattgc ttcatgaatt tgaaacgatt      240
cctgttttat ccgttgagtt aagcccagaa gatgtggacg cgcttgaact cgatccagcg      300
atttcttata ttgaagagga tgcagaagta acgacaatg                             339
```

```
<210> SEQ ID NO 11
<211> LENGTH: 2971
<212> TYPE: DNA
<213> ORGANISM: Bacillus subtilis

<400> SEQUENCE: 11
aacgcctcac tcctcacatc aacccgttac ttctattgta atcataaatt caaattctta       60
gaaccaagct gtgttccgca cttttccacc cttttaagca tggaaacccc gatcgctggg      120
aaaactaaca atgtttggag tgatgcaaat gaaaaaaata gtggcagcca tcgtggtaat      180
cggtcttgtg tttatcgcat ttttttatct ttacagccga tcaggcgatg tgtatcaatc      240
ggtagacgcg gatttgatca cactgtcttc aagcggccag gaagatatcg agattgaaaa      300
aagacagcac gtcaaagata tgctggatat tatgaatcag ggaaaacagg tgaagacaga      360
aaaaacatca gcccctgatt acgaagggac aatcaagttt cataaagacc ggtatgactc      420
attcagacta tggattgacg gcagccagca agccgttttt ttgaaggatg gcacatacta      480
caaattaagc aaaaatgata caaaggcgct gctaaatatt attaaaaaag aagcaaagga      540
ttgaaaatga aaaagcgaag ctaaccgctt cgctttttca ttttattggg gcaaaatatc      600
tctcagtgcc cgtctgagca ttttccccgt cgcattttc ggaatatcgt caagaaacgt       660
aatggcggca ggccgcttgt attttgccag atgctttcg cagtgctgca tgatgtcctc        720
ctctgttacc ccagagcgtt tcggcaccac atatcccttt accgcttccc cgctttgggg      780
gtccggcacg ccgatgacaa ccgcctcctt gacgtccgga tggctgtaca gcacctcctc      840
cacctcccgc ggatacacat tgtatcctcc tacaatgatc atgtcttttt tccggtcaac      900
aatgtaaaaa tagccgtcct catcccgtct tgccaagtcc cccgtataaa gccacccgtc      960
ttttaatgca tgctctgttt ccatcggcat tttataatag cccttcatca cattggggcc     1020
tttcacgatc aattcgccga cctggtgagc gggcagctcg cgtccgagcg gatctacgac     1080
cttgttttcg acatgtaaga tacttgtccc gatggagccc ggctttctgc ccctgtcaaa     1140
cgggttaaag cacgtgacgg gtgatgcttc cgagagcccg tagccttcca aaatggtaac     1200
accgaatttt tcttcaaacg ccgtcagcaa cgcgactggc atggacgcgc ctcccgaaat     1260
gcacagccgg atcgaagaaa aatcatcttt ctttccgttt tcatgctgaa acaagtagtt     1320
atacattgta ggcacaccgg caaaaatggt cgcctgctgc tgcttaacaa gcttaaaaac     1380
agatgccgga ctgaattgag gctcaatcaa tacagttgcg ccgctcatca gcggtgcatt     1440
catacagacg gttaaacaaa acacgtgaaa catgggaaga gcgcagacca cattgtccct     1500
ctcatccatt cccaaatagc ctgcgacatc gttggcattg ctgtacaaat tctgatgtgt     1560
cagcatcgcg cctttcggtt ttccagtcgt tcctgacgta tataaaataa ccgcggtatc     1620
atcaggtaca ggttcttggt tttgtttagc ggcagatgtc ggccgcaata tttttgcaaa     1680
cgttgtcatt ttcatcctga cctctgggtc cgcagcttcc ggctcggcct ccccgtctg       1740 gcataaaatg acgagctcaa cctttggcag cgattcatgc atgctctcat aaagcggcaa     1800
```

-continued

```
aagctggcta acgcccacga ttgcctttac atcgccattt gtcagcatat aaccaatttc   1860
tgtcggcgtg tacaacggat tgatgggaac aactacgatc ccagctttta aagcgccaaa   1920
aaacgcgatg ataaaatcag gcgaattgcc aagcagcaaa gctaaatggt cccctttctc   1980
cataccggct tcctgaaggc cgtccgcaaa tcgctgaata tattcattca gctcttgata   2040
cgtcatcatg tgatctttaa acctgcatgc gatgctgtcg ggcttctcag atgctgtttc   2100
ttccaatttt gaaacaagat tcattctccc accccttaag tgaatgaata gtcattcatt   2160
attgaagcca agctttcttc tccattatag agaaacagaa aaaaacactc aagagcaaaa   2220
agccctgagt gtcagtactg tcatagtttc ttcaatgctt cggcaatcgg cgtatctcct   2280
tctgtcagat caaaggcccg attttccgta ttcttctcat ctaaagaggc aatgaccgtt   2340
tttgcaacgt catcacggga aataaatccc cgctccagat ccttcgctgc tgaaacagtt   2400
cccgttccag gctcattgcg aaggcctccc ggacggataa tcgtataggt taaaccgctc   2460
gcttccagaa ttttatcagc ataatgcttg gccacataat aaggcttgag tgcctcattc   2520
caattttcac ggttatgggc ttgcagggcg ctgaccataa taaaccgttt gattccggca   2580
atggccgcag cttcaatggc ttttgccgct ccatcaagat ccaccagcag cgtttttatca   2640 tagcctgtgc tgccgccgga accggctgtg aaaatgatcg cgtcacaacc ttttgccgca   2700
gcggcgattt cttccgggct gccctccaga ttcgcaagca cagcttctgc accggcagct   2760
tcaagagacg ctttctgttc ttcttttctg accatcgctc tgatggaatg atcaggatta   2820
tcttggaata aagagacgag tctttgcccg atttgtccgt tcgctccgat taaaaacact   2880
ttcatgtgaa tccctcctgc ctccattatt tcaaaaacac aaccgctctt tcaaacgatg   2940
tgttttgcct tagtaaatca gatcaaggaa a   2971
```

<210> SEQ ID NO 12
<211> LENGTH: 20
<212> TYPE: DNA
<213> ORGANISM: artificial sequence
<220> FEATURE:
<223> OTHER INFORMATION: synthesized sequence- primer

<400> SEQUENCE: 12

```
tcgtcaacgc ctgcctcagc   20
```

<210> SEQ ID NO 13
<211> LENGTH: 25
<212> TYPE: DNA
<213> ORGANISM: artificial sequence
<220> FEATURE:
<223> OTHER INFORMATION: synthesized sequence- primer

<400> SEQUENCE: 13

```
tttccttgat ctgatttact aaggc   25
```

<210> SEQ ID NO 14
<211> LENGTH: 7488
<212> TYPE: DNA
<213> ORGANISM: artificial sequence
<220> FEATURE:
<223> OTHER INFORMATION: synthesized sequence

<400> SEQUENCE: 14

```
tcgtcaacgc ctgcctcagc aacattgaat ttgcagaaga aaaatggcgg ataaaagact   60
ataatatcaa cagccactta tccggcttta tcaaataaga aaaagacagg cgtttgcctg   120
tcttttcttt tatttcttag cagccggcat ctcttttga agctcgtcca aaatggcatt   180
```

-continued

```
cgccccgtct acactgcggc gcagagacca caccgcacga tccacgtggt atacatgccc    240 gttttttcact gccttcagtt tttttccaaag gacattcttt tcgatcgggc gtttaccgtc    300
ggcgtcgagg tcatctgttt ttcctgtcat caggatgatc acatccggat ctgttttcag    360
cagctgctcc agtgtcattt tcatattcac agagtcgccg ccattgcttg aatcgctatt    420
gcctgacgta ctgattgcat atcggtagcc gacctgtgtt aaaagtctcg atgtaaagaa    480
gttttcatcc ctggccataa tggtatcatt tgtatttccg atcaaaagca cggactggct    540
gttcgcgctg attttctgct ttgtctcgct aagcttttct tcatgcgccg tcagcttttt    600
ctccatttcc ttctccttgc cgactgcttt tgcaatcgta agcgaagcgt caattgtatc    660
ctgataatca gcatttaaat tattaagtgc aatcgtcggc gctattttt tcagctgatc    720 gtacaccttc ttatgccggg tcgtgtcagc aataattaaa tcgggtttta atgaagcgat    780
tttttccatg cttggctgtg agcgagtgcc gacagatgtg tagccgtcaa ttttcttcag    840
cacatccttg ttgatcagct gcttcgcttt gttgtcatcg gcaacccga caggcgtaat    900 gccgagatca agcagtgtat caataaaacc tagctcaaga acaacaaccc gcttcggatg    960
ctcaggcaca tttgtcttcc ctaaatcatg tgttaccgcc actttatgtt ctttactgtt    1020
ttgattgccg cttgaagacg agcaagcagc cgttaagaca gaaagaagta aaactgtaag    1080
aataatcagt gttttttttca tatgttccag tctctcctgt tggtagtttc tatggttaag    1140
atgtccaaga gtagtataac acggaatgag aatcattatc accaattatt tttaaaatga    1200
gaagagaaag ttcggcttac aggaaaatct tgtttcgcga cacagcagtt cagcagctga    1260
tcatcctgtc cacaaaaaag cttgcagaaa aataacattc tctgcaagct gatcctgtta    1320
aagcttcaca atcactcttc cttgaatgcg attttgcaaa atatctttta acgcacccgg    1380
cgtttcttcc aatgatactt ccctgtccac gatggtcagc agctgatcag gcttgagatc    1440
agaagacatg cgctcccaaa cagcggctct gacgtccatc ggacaatata ctgaatcgat    1500
tccgagcagg cttactccgc gaagaataaa aggatacacg gttgccggaa cttctcctcc    1560
gccggttaag ccgctcactg cgacagatcc gccgtattga attttgctta aaagcgaggc    1620
aagctgtttt ccgccgactg gatcaaccgc tccctgccat tgctgcttgg acagcgcctt    1680
aagcgttccg tcatagacat cttccctgct gattacttcg cttgcaccaa gctgtttcaa    1740
ataatcagcc gcctcccggt ttccggtact tgccaccaca tcataacccc gcttgttcag    1800
catcgatacc gcaattccgc cgacaccgcc ggttgctcct gtgactagca cgctgccttt    1860
ttccggagac agaccgttct gttcaagccg atgcactgat aacgccgcag taaatcccgc    1920
cgttccgtac accatcgctt cttttaacga aagattctgt ggcaaaggca ccagccagtc    1980
accaggcacc gaagcgtatt cacttaatcc gccatcacgt gagacaccga gctcatagct    2040
tgtcgcgatc acctcatccc cctccgcaaa acgcggatca ttggaagaga cgaccgtacc    2100
cgcagcatca atgcctaaaa taagcggata ctctctgacg atattgcctc ctgctttttcc    2160 ggccagacca tctttgtaat taatgccgga ataagcaact ttaatcagga caccatcctt    2220
cggcaaatcc tctgttgata tggttttcac atggactgaa acatcatcgg cattttttttc    2280 tgcctgcaag gcttgaaata acgttgacat tcggcacact ccttttcatt tatatcgtaa    2340
ccgaagaacg ttcaaaaaac caaatcatca agccgccatt ttcacttcgc cggcacattg    2400
agacaataat ggacaaatcc ggtatcctct tcatagccgt tttgctcata caagcttctt    2460
gccttccggt tgtggtgctc agtctgaagt gttaaacatt ttgccccgtt ttgccctgca    2520
```

-continued

```
taatcctttg cggcagaaag cagccggccg ccggctccct ttgtacgcgc atgaggaacg    2580
acaaataagt catttaatat gtatatcctt ttcattgaca cagaagaaaa cgttggatag    2640
agctgggtaa agcctatgaa ttctccattt tcttctgcta tcaaaataac agactcgtga    2700
ttttccaaac gagctttcaa aaaagcctct gccccttgca aatcggatgc ctgtctataa    2760
aattcccgat attggttaaa cagcggcgca atggcggccg catctgatgt ctttgcttgg    2820
cgaatgttca tcttatttct tcctccctct caataatttt ttcattctat cccttttctg    2880
taaagtttat ttttcagaat actttttatca tcatgctttg aaaaaatatc acgataatat    2940
ccattgttct cacggaagca cacgcgctga taaacagctg acatcaacta aaagtttcat    3000
taaatacttt gaaaaaagtt gttgacttaa aagaagctaa atgttatagt aattgtacag    3060
aatagtcttt taagtaagtc tactctgaat tttttaaaa ggagagggta aagagtgaga    3120
agcaaaaaat tgtggatcag cttgttgttt gcgttaacgt taatctttac gatggcgttc    3180
agcaacatgt ctgcgcaggc tgctgaagaa gcaaaagaaa aatatttaat tggctttaat    3240
gagcaggaag ctgtcagtga gtttgtagaa caagtagagg caaatgacga ggtcgccatt    3300
ctctctgagg aagaggaagt cgaaattgaa ttgcttcatg aatttgaaac gattcctgtt    3360
ttatccgttg agttaagccc agaagatgtg gacgcgcttg aactcgatcc agcgatttct    3420
tatattgaag aggatgcaga agtaacgaca atgcaacaaa cagtgccatg gggaattact    3480
cgtgtgcaag ccccagctgt tcataaccgt ggaattacag gttctggtgt aagagttgct    3540
atcctcgatt caggtatttc cacacatgaa gacttaaatg ttcgtggtgg cgttagcttt    3600
gtaccagggg aaccaacgta tgctgattta aatgggcatg gcacgcatgt ggctgggacg    3660
gtagctgctt taaacaattc gattggcgtt gttggcgtag caccgtcagc ggatctatac    3720
gctgttaaag tattaggggc gaatggtaga ggttcggtca gcgggattgc ccaaggattg    3780
gaatgggcag cacaaaataa catgcacatt gctaatatga gtttaggaac agatgcacca    3840 agttctcacac ttgagcgtgc tgttaattat gcgacttcta gagatgttct tgttattgcg    3900
gcaactggga ataacggttc tggctcagta ggctatccgg cccgttatgc gaacgcaatg    3960
gcagtcggag ctactgacca aaacaacaga cgcgccaact tttcacagta tggcacgggg    4020
attgacattg tcgcaccagg tgtaaacgtg cagagcacat acccaggtaa ccgttatgtg    4080
agcatgaacg gtacatcgat ggctactcct catgttgcag gtgcagcagc ccttgttaaa    4140
caacgctatc catcttggaa tgcgactcaa atccgcgacc atctaaagaa tacggcaacg    4200
aatttaggaa actcttcaca atttggaagc ggacttgtca atgcagaagc ggcaacacgc    4260
taatctagat acataaaaaa ccggccttgg ccccgccggt tttttattat ttttcttcct    4320
ccgcatgttc aatccgctcc ataatcgacg gatggctccc tctgaaaatt ttaacgagaa    4380
acggcgggtt gacccggctc agtcccgtaa cggccaagtc ctgaaacgtc tcaatcgccg    4440
cttcccggtt tccggtcagc tcaatgccgt aacggtcggc ggcgttttcc tgataccggg    4500
agacggcatt cgtaatcaac gcctcactcc tcacatcaac ccgttacttc tattgtaatc    4560
ataaattcaa attcttagaa ccaagctgtg ttccgcactt ttccacccctt ttaagcatgg    4620 aaaccccgat cgctgggaaa actaacaatg tttggagtga tgcaaatgaa aaaaatagtg    4680
gcagccatcg tggtaatcgg tcttgtgttt atcgcatttt tttatctttta cagccgatca    4740 ggcgatgtgt atcaatcggt agacgcggat ttgatcacac tgtcttcaag cggccaggaa    4800
gatatcgaga ttgaaaaaag acagcacgtc aaagatatgc tggatattat gaatcaggga    4860
aaacaggtga agacagaaaa aacatcagcc cctgattacg aagggacaat caagtttcat    4920
```

-continued

```
aaagaccggt atgactcatt cagactatgg attgacggca gccagcaagc cgtttttttg   4980
aaggatggca catactacaa attaagcaaa aatgatacaa aggcgctgct aaatattatt   5040
aaaaaagaag caaaggattg aaaatgaaaa agcgaagcta accgcttcgc tttttcattt   5100
tattggggca aaatatctct cagtgcccgt ctgagcattt tccccgtcgc attttttcgga  5160 atatcgtcaa gaaacgtaat ggcggcaggc cgcttgtatt ttgccagatg cttttcgcag   5220
tgctgcatga tgtcctcctc tgttaccccca gagcgtttcg gcaccacata tccctttacc  5280
gcttccccgc tttggggggtc cggcacgccg atgacaaccg cctccttgac gtccggatgg   5340
ctgtacagca cctcctccac ctcccgcgga tacacattgt atcctcctac aatgatcatg   5400
tcttttttcc ggtcaacaat gtaaaaatag ccgtcctcat cccgtcttgc caagtccccc   5460
gtataaagcc acccgtcttt taatgcatgc tctgtttcca tcggcatttt ataatagccc   5520
ttcatcacat tggggccttt cacgatcaat tcgccgacct ggtgagcggg cagctcgcgt   5580
ccgagcggat ctacgacctt gttttcgaca tgtaagatac ttgtcccgat ggagcccggc   5640
tttctgcccc tgtcaaacgg gttaaagcac gtgacgggtg atgcttccga gagcccgtag   5700
ccttccaaaa tggtaacacc gaattttttct tcaaacgccg tcagcaacgc gactggcatg   5760
gacgcgcctc ccgaaatgca cagccggatc gaagaaaaat catctttctt tccgtttttca  5820 tgctgaaaca agtagttata cattgtaggc acaccggcaa aaatggtcgc ctgctgctgc   5880
ttaacaagct taaaaacaga tgccggactg aattgaggct caatcaatac agttgcgccg   5940
ctcatcagcg gtgcattcat acagacggtt aaacaaaaca cgtgaaacat gggaagagcg   6000
cagaccacat tgtccctctc atccattccc aaatagcctg cgacatcgtt ggcattgctg   6060
tacaaattct gatgtgtcag catcgcgcct ttcggttttc cagtcgttcc tgacgtatat   6120
aaaataaccg cggtatcatc aggtacaggt tcttggtttt gtttagcggc agatgtcggc   6180
cgcaatattt ttgcaaacgt tgtcattttc atcctgacct ctgggtccgc agcttccggc   6240
tcggcctccc ccgtctggca taaaatgacg agctcaacct ttggcagcga ttcatgcatg   6300
ctctcataaa gcggcaaaag ctggctaacg cccacgattg cctttacatc gccatttgtc   6360
agcatataac caatttctgt cggcgtgtac aacggattga tgggaacaac tacgatccca   6420
gcttttaaag cgccaaaaaa cgcgatgata aaatcaggcg aattgccaag cagcaaagct   6480
aaatggtccc ctttctccat accggcttcc tgaaggccgt ccgcaaatcg ctgaatatat   6540
tcattcagct cttgatacgt catcatgtga tctttaaacc tgcatgcgat gctgtcgggc   6600
ttctcagatg ctgtttcttc caattttgaa acaagattca ttctcccacc ccttaagtga   6660
atgaatagtc attcattatt gaagccaagc tttcttctcc attatagaga aacagaaaaa   6720
aacactcaag agcaaaaagc cctgagtgtc agtactgtca tagtttcttc aatgcttcgg   6780
caatcggcgt atctccttct gtcagatcaa aggcccgatt ttccgtattc ttctcatcta   6840
aagaggcaat gaccgttttt gcaacgtcat cacgggaaat aaatccccgc tccagatcct   6900
tcgctgctga aacagttccc gttccaggct cattgcgaag gcctcccgga cggataatcg   6960
tataggttaa accgctcgct tccagaattt tatcagcata atgcttggcc acataataag   7020
gcttgagtgc ctcattccaa ttttcacggt tatgggcttg cagggcgctg accataataa   7080
accgtttgat tccggcaatg gccgcagctt caatggcttt tgccgctcca tcaagatcca   7140
ccagcagcgt tttatcatag cctgtgctgc cgccggaacc ggctgtgaaa atgatcgcgt   7200
cacaaccttt tgccgcagcg gcgatttctt ccgggctgcc ctccagattc gcaagcacag   7260
```

-continued

```
cttctgcacc ggcagcttca agagacgctt tctgttcttc ttttctgacc atcgctctga      7320
tggaatgatc aggattatct tggaataaag agacgagtct ttgcccgatt tgtccgttcg      7380
ctccgattaa aaacactttc atgtgaatcc ctcctgcctc cattatttca aaaacacaac      7440
cgctctttca aacgatgtgt tttgccttag taaatcagat caaggaaa                   7488

<210> SEQ ID NO 15
<211> LENGTH: 576
<212> TYPE: DNA
<213> ORGANISM: Bacillus subtilis

<400> SEQUENCE: 15
atgagtcaga aaacagacgc acctttagaa tcgtatgaag tgaacggcgc aacaattgcc        60
gtgctgccag aagaaataga cggcaaaatc tgttccaaaa ttattgaaaa agattgcgtg       120
ttttatgtaa acatgaagcc gctgcaaatt gtcgacagaa gctgccgatt ttttggatca       180
agctatgcgg gaagaaaagc aggaacttat gaagtgacaa aaatttcaca caagccgccg       240
atcatggtgg acccttcgaa ccaaatcttt ttattcccta cactttcttc gacaagaccc       300
caatgcggct ggatttccca tgtgcatgta aaagaattca agcgactgaa attcgacgat       360
acggaagtga cgttttccaa tgggaaaacg atggagctgc cgatctctta taattcgttc       420
gagaaccagg ttaccgaac agcgtggctc agaaccaaat tccaagacag aatcgaccac        480
cgcgtgccga aagacagga atttatgctg tacccgaaag aagagcggac gaagatgatt        540
tatgatttta ttttgcgtga gctcggggaa cggtat                               576

<210> SEQ ID NO 16
<211> LENGTH: 26
<212> TYPE: DNA
<213> ORGANISM: artificial sequence
<220> FEATURE:
<223> OTHER INFORMATION: synthesized sequence- primer

<400> SEQUENCE: 16
cacgataata tccattgttc tcacgg                                          26

<210> SEQ ID NO 17
<211> LENGTH: 20
<212> TYPE: DNA
<213> ORGANISM: artificial sequence
<220> FEATURE:
<223> OTHER INFORMATION: synthesized sequence- primer

<400> SEQUENCE: 17
gatatgtggt gccgaaacgc                                                20

<210> SEQ ID NO 18
<211> LENGTH: 20
<212> TYPE: DNA
<213> ORGANISM: artificial sequence
<220> FEATURE:
<223> OTHER INFORMATION: synthesized sequence- primer

<400> SEQUENCE: 18
gcaaaacgcg gatcattgga                                                20

<210> SEQ ID NO 19
<211> LENGTH: 22
<212> TYPE: DNA
<213> ORGANISM: artificial sequence
<220> FEATURE:
<223> OTHER INFORMATION: synthesized sequence- primer
```

<400> SEQUENCE: 19
gtttgcaaaa atattgcggc cg                                                          22

<210> SEQ ID NO 20
<211> LENGTH: 21
<212> TYPE: DNA
<213> ORGANISM: artificial sequence
<220> FEATURE:
<223> OTHER INFORMATION: synthesized sequence- primer

<400> SEQUENCE: 20
ccatgatacg cggaagaacc g                                                           21

<210> SEQ ID NO 21
<211> LENGTH: 21
<212> TYPE: DNA
<213> ORGANISM: artificial sequence
<220> FEATURE:
<223> OTHER INFORMATION: synthesized sequence

<400> SEQUENCE: 21
gctatcaaaa taacagactc g                                                           21

<210> SEQ ID NO 22
<211> LENGTH: 2209
<212> TYPE: DNA
<213> ORGANISM: artificial sequence
<220> FEATURE:
<223> OTHER INFORMATION: synthesized sequence

<400> SEQUENCE: 22
cacgataata tccattgttc tcacggaagc acacgcaggt catttgaacg aattttttcg        60
acaggaattt gccgggactc aggagcattt aacctaaaaa agcatgacat ttcagcataa        120
tgaacattta ctcatgtcta ttttcgttct tttctgtatg aaaatagtta tttcgagtct       180
ctacggaaat agcgagagat gatatccta aatagagata aaatcatctc aaaaaaatgg        240
gtctactaaa atattattcc atctattaca ataaattcac agaatagtct tttaagtaag        300
tctactctga attttttaa aaggagaggg taaagagtgt caacaacata tcctattgtc        360
ctggtacacg gcctttctgg tttcgatgac atcgtaggat acccttattt ttatgggatt       420
gccgacgccc tggagaaaga tggccacaaa gtttttacag cctcactctc tgcattcaat       480
tccaacgaag tccgtggcga gcaattatgg gagttcgtgc aaaagattct caaagagact       540
aaagcaaaaa aggtgaattt gatcgggcac tcccaaggtc ctcttgcgtg tcgttatgtg       600
gcggccaagc atgctaaaag tattgcaagt gttacatctg tgaatggagt gaatcacggt       660
agcgaaatcg ccgatcttgt cagacggatt atgagaaaag attctgtccc tgagtatatc       720
gcggacgcgg taatgaaggc tattggcact ataatcagta cttttagcgg aaatagagga       780
aaccctcaag acgctatagc agctctggag gccttaacga cggaaaacgt gatggaattt       840
aacaaaaaat atcctcaggg actgccagca attcgtgggg gtgaaggtaa agaagtcgtg       900
aacggcgtac actactatag ctttggttct tacatacagg gtctcatcgc tggcgagaag       960
ggaaacttgc tcgatcctac ccacgccgct atgcgcgttt tatccgcgtt tttttcagaa       1020
cgtgagaacg atggtttagt aggacggact tcaatgcggc tcggcaagtt aattaaagac       1080
gactacgctg aggatcattt agatatggtc aatcaagttg cggggttagt tggacgcggg       1140
gaggatataa ttgctatata tacgaatcat gccaattttt tagcgtcaaa aaagctctaa       1200

-continued

```
tctagataca taaaaaaccg gccttggccc cgccggtttt ttattatttt tcttcctccg    1260
catgttcaat ccgctccata atcgacggat ggctccctct gaaaattttta acgagaaacg    1320 gcgggttgac ccggctcagt cccgtaacgg ccaagtcctg aaacgtctca atcgccgctt    1380
cccggtttcc ggtcagctca atgccgtaac ggtcggcggc gttttcctga taccgggaga    1440
cggcattcgt aatcaacgcc tcactcctca catcaacccg ttacttctat tgtaatcata    1500
aattcaaatt cttagaacca agctgtgttc cgcacttttc cacccttta agcatggaaa    1560 ccccgatcgc tgggaaaact aacaatgttt ggagtgatgc aaatgaaaaa aatagtggca    1620
gccatcgtgg taatcggtct tgtgtttatc gcattttttt atctttacag ccgatcaggc    1680
gatgtgtatc aatcggtaga cgcggatttg atcacactgt cttcaagcgg ccaggaagat    1740
atcgagattg aaaaaagaca gcacgtcaaa gatatgctgg atattatgaa tcagggaaaa    1800
caggtgaaga cagaaaaaac atcagcccct gattacgaag ggacaatcaa gtttcataaa    1860
gaccggtatg actcattcag actatggatt gacggcagcc agcaagccgt tttttgaag    1920 gatggcacat actacaaatt aagcaaaaat gatacaaagg cgctgctaaa tattattaaa    1980
aaagaagcaa aggattgaaa atgaaaaagc gaagctaacc gcttcgcttt ttcatttttat    2040 tggggcaaaa tatctctcag tgcccgtctg agcattttcc ccgtcgcatt tttcggaata    2100
tcgtcaagaa acgtaatggc ggcaggccgc ttgtattttg ccagatgctt ttcgcagtgc    2160
tgcatgatgt cctcctctgt taccccagag cgtttcggca ccacatatc                2209
```

```
<210> SEQ ID NO 23
<211> LENGTH: 3999
<212> TYPE: DNA
<213> ORGANISM: artificial sequence
<220> FEATURE:
<223> OTHER INFORMATION: synthesized sequence

<400> SEQUENCE: 23
gcaaaacgcg gatcattgga agagacgacc gtacccgcag catcaatgcc taaaataagc      60
ggatactctc tgacgatatt gcctcctgct tttccggcca gaccatcttt gtaattaatg    120
ccggaataag caactttaat caggacacca tccttcggca aatcctctgt tgatatggtt    180
ttcacatgga ctgaaacatc atcggcattt ttttctgcct gcaaggcttg aaataacgtt    240
gacattcggc acactccttt tcatttatat cgtaaccgaa gaacgttcaa aaaaccaaat    300
catcaagccg ccattttcac ttcgccggca cattgagaca ataatggaca aatccggtat    360
cctcttcata gccgttttgc tcatacaagc ttcttgcctt ccggttgtgg tgctcagtct    420
gaagtgttaa acattttgcc ccgttttgcc ctgcataatc ctttgcggca gaaagcagcc    480
ggccgccggc tccctttgta cgcgcatgag gaacgacaaa taagtcattt aatatgtata    540
tccttttcat tgacacagaa gaaaacgttg gatagagctg ggtaaagcct atgaattctc    600
cattttcttc tgctatcaaa ataacagact cgtgattttc caaacgagct ttcaaaaaag    660
cctctgcccc ttgcaaatcg gatgcctgtc tataaaattc ccgatattgg ttaaacagcg    720
gcgcaatggc ggccgcatct gatgtctttg cttggcgaat gttcatctta tttcttcctc    780
cctctcaata attttttcat tctatcccct ttctgtaaag tttattttttc agaatacttt    840 tatcatcatg ctttgaaaaa atatcacgat aatatccatt gttctcacgg aagcacacgc    900
aggtcatttg aacgaatttt ttcgacagga atttgccggg actcaggagc atttaaccta    960
aaaaagcatg acatttcagc ataatgaaca tttactcatg tctatttttcg ttcttttctg    1020 tatgaaaata gttatttcga gtctctacgg aaatagcgag agatgatata cctaaataga    1080
```

```
gataaaatca tctcaaaaaa atgggtctac taaaatatta ttccatctat tacaataaat   1140
tcacagaata gtcttttaag taagtctact ctgaattttt ttaaaaggag agggtaaaga   1200
gtgtcaacaa catatcctat tgtcctggta cacggccttt ctggtttcga tgacatcgta   1260 ggatacccctt atttttatgg gattgccgac gccctggaga aagatggcca caaagttttt   1320
acagcctcac tctctgcatt caattccaac gaagtccgtg gcgagcaatt atgggagttc   1380
gtgcaaaaga ttctcaaaga gactaaagca aaaaaggtga atttgatcgg gcactcccaa   1440
ggtcctcttg cgtgtcgtta tgtggcggcc aagcatgcta aaagtattgc aagtgttaca   1500
tctgtgaatg gagtgaatca cggtagcgaa atcgccgatc ttgtcagacg gattatgaga   1560
aaagattctg tccctgagta tatcgcggac gcggtaatga aggctattgg cactataatc   1620 agtacttta gcggaaatag aggaaaccct caagacgcta tagcagctct ggaggcctta   1680
acgacggaaa acgtgatgga atttaacaaa aaatatcctc agggactgcc agcaattcgt   1740
gggggtgaag gtaaagaagt cgtgaacggc gtacactact atagctttgg ttcttacata   1800
cagggtctca tcgctggcga gaagggaaac ttgctcgatc ctacccacgc cgctatgcgc   1860
gttttatccg cgttttttc agaacgtgag aacgatggtt tagtaggacg gacttcaatg   1920
cggctcggca agttaattaa agacgactac gctgaggatc atttagatat ggtcaatcaa   1980 gttgcgggt tagttggacg cggggaggat ataattgcta tatatacgaa tcatgccaat   2040
tttttagcgt caaaaaagct ctaatctaga tacataaaaa accggccttg gccccgccgg   2100
ttttttatta tttttcttcc tccgcatgtt caatccgctc cataatcgac ggatggctcc   2160
ctctgaaaat tttaacgaga aacggcgggt tgacccggct cagtcccgta acggccaagt   2220
cctgaaacgt ctcaatcgcc gcttcccggt ttccggtcag ctcaatgccg taacggtcgg   2280 cggcgtttc ctgataccgg gagacggcat tcgtaatcaa cgcctcactc ctcacatcaa   2340
cccgttactt ctattgtaat cataaattca aattcttaga accaagctgt gttccgcact   2400
tttccaccct tttaagcatg gaaaccccga tcgctgggaa aactaacaat gtttggagtg   2460
atgcaaatga aaaaaatagt ggcagccatc gtggtaatcg gtcttgtgtt tatcgcattt   2520
ttttatcttt acagccgatc aggcgatgtg tatcaatcgg tagacgcgga tttgatcaca   2580
ctgtcttcaa gcggccagga agatatcgag attgaaaaaa gacagcacgt caaagatatg   2640
ctggatatta tgaatcaggg aaaacaggtg aagacagaaa aaacatcagc ccctgattac   2700
gaagggacaa tcaagtttca taaagaccgg tatgactcat tcagactatg gattgacggc   2760
agccagcaag ccgttttttt gaaggatggc acatactaca aattaagcaa aaatgataca   2820
aaggcgctgc taaatattat taaaaaagaa gcaaggatt gaaaatgaaa aagcgaagct   2880
aaccgcttcg cttttttcatt ttattggggc aaaatatctc tcagtgcccg tctgagcatt   2940
ttccccgtcg cattttttcgg aatatcgtca agaaacgtaa tggcggcagg ccgcttgtat   3000
tttgccagat gcttttcgca gtgctgcatg atgtcctcct ctgttacccc agagcgtttc   3060
ggcaccacat atccctttac cgcttcccg ctttgggggt ccggcacgcc gatgacaacc   3120
gcctccttga cgtccggatg gctgtacagc acctcctcca cctcccgcgg atacacattg   3180
tatcctccta caatgatcat gtcttttttc cggtcaacaa tgtaaaaata gccgtcctca   3240
tcccgtcttg ccaagtcccc cgtataaagc cacccgtctt ttaatgcatg ctctgtttcc   3300
atcggcattt tataatagcc cttcatcaca ttgggggcctt tcacgatcaa ttcgccgacc   3360
tggtgagcgg gcagctcgcg tccgagcgga tctacgacct tgttttcgac atgtaagata   3420
```

```
cttgtcccga tggagcccgg cttttctgccc ctgtcaaacg ggttaaagca cgtgacgggt    3480
gatgcttccg agagcccgta gccttccaaa atggtaacac cgaattttttc ttcaaacgcc    3540 gtcagcaacg cgactggcat ggacgcgcct cccgaaatgc acagccggat cgaagaaaaa    3600
tcatctttct ttccgttttc atgctgaaac aagtagttat acattgtagg cacaccggca    3660
aaaatggtcg cctgctgctg cttaacaagc ttaaaaacag atgccggact gaattgaggc    3720
tcaatcaata cagttgcgcc gctcatcagc ggtgcattca tacagacggt taaacaaaac    3780
acgtgaaaca tgggaagagc gcagaccaca ttgtccctct catccattcc caaatagcct    3840
gcgacatcgt tggcattgct gtacaaattc tgatgtgtca gcatcgcgcc tttcggtttt    3900
ccagtcgttc ctgacgtata taaaataacc gcggtatcat caggtacagg ttcttggttt    3960
tgtttagcgg cagatgtcgg ccgcaatatt tttgcaaac                            3999
```

```
<210> SEQ ID NO 24
<211> LENGTH: 5289
<212> TYPE: DNA
<213> ORGANISM: artificial sequence
<220> FEATURE:
<223> OTHER INFORMATION: synthesized sequence

<400> SEQUENCE: 24
gcaaaacgcg gatcattgga agagacgacc gtacccgcag catcaatgcc taaaataagc      60
ggatactctc tgacgatatt gcctcctgct tttccggcca gaccatcttt gtaattaatg     120
ccggaataag caactttaat caggacacca tccttcggca aatcctctgt tgatatggtt     180
ttcacatgga ctgaaacatc atcggcattt ttttctgcct gcaaggcttg aaataacgtt     240
gacattcggc acactccttt tcatttatat cgtaaccgaa gaacgttcaa aaaaccaaat     300
catcaagccg ccattttcac ttcgccggca cattgagaca ataatggaca aatccggtat     360
cctcttcata gccgttttgc tcatacaagc ttcttgcctt ccggttgtgg tgctcagtct     420
gaagtgttaa acattttgcc ccgtttttgcc ctgcataatc ctttgcggca gaaagcagcc    480
ggccgccggc tccctttgta cgcgcatgag gaacgacaaa taagtcattt aatatgtata     540 tcctttttcat tgacacagaa gaaaacgttg gatagagctg ggtaaagcct atgaattctc    600
cattttcttc tgctatcaaa ataacagact cgtgattttc caaacgagct ttcaaaaaag     660
cctctgcccc ttgcaaatcg gatgcctgtc tataaaattc ccgatattgg ttaaacagcg     720
gcgcaatggc ggccgcatct gatgtctttg cttggcgaat gttcatctta tttcttcctc     780
cctctcaata atttttttcat tctatcccctt ttctgtaaag tttatttttc agaatacttt    840
tatcatcatg ctttgaaaaa atatcacgat aatatccatt gttctcacgg aagcacacgc     900
aggtcatttg aacgaatttt ttcgacagga atttgccggg actcaggagc atttaaccta     960
aaaaagcatg acatttcagc ataatgaaca tttactcatg tctattttcg ttctttttctg    1020 tatgaaaata gttatttcga gtctctacgg aaatagcgag agatgatata cctaaataga    1080
gataaaatca tctcaaaaaa atgggtctac taaaatatta ttccatctat tacaataaat     1140
tcacagaata gtcttttaag taagtctact ctgaattttt ttaaaaggag agggtaaaga     1200
gtgtcaacaa catatcctat tgtcctggta cacggccttt ctggtttcga tgacatcgta     1260 ggatacccctt attttttatgg gattgccgac gccctggaga aagatggcca caaagttttt    1320
acagcctcac tctctgcatt caattccaac gaagtccgtg gcgagcaatt atgggagttc     1380
gtgcaaaaga ttctcaaaga gactaaagca aaaaaggtga atttgatcgg gcactcccaa     1440
ggtcctcttg cgtgtcgtta tgtggcggcc aagcatgcta aaagtattgc aagtgttaca    1500
```

```
tctgtgaatg gagtgaatca cggtagcgaa atcgccgatc ttgtcagacg gattatgaga   1560
aaagattctg tccctgagta tatcgcggac gcggtaatga aggctattgg cactataatc   1620 agtacttta gcggaaatag aggaaaccct caagacgcta tagcagctct ggaggcctta    1680
acgacggaaa acgtgatgga atttaacaaa aaatatcctc agggactgcc agcaattcgt    1740
gggggtgaag gtaaagaagt cgtgaacggc gtacactact atagctttgg ttcttacata    1800
cagggtctca tcgctggcga gaagggaaac ttgctcgatc ctacccacgc cgctatgcgc    1860
gttttatccg cgttttttc agaacgtgag aacgatggtt tagtaggacg gacttcaatg    1920
cggctcggca agttaattaa agacgactac gctgaggatc atttagatat ggtcaatcaa   1980
gttgcggggt tagttggacg cggggaggat ataattgcta tatatacgaa tcatgccaat   2040
tttttagcgt caaaaaagct ctaatctaga tacataaaaa accggccttg gccccgccgg    2100
ttttttatta tttttcttcc tccgcatgtt caatccgctc cataatcgac ggatggctcc    2160
ctctgaaaat tttaacgaga aacgcgggt tgacccggct cagtcccgta acggccaagt     2220
cctgaaacgt ctcaatcgcc gcttcccggt ttccggtcag ctcaatgccg taacggtcgg    2280 cggcgtttc ctgataccgg gagacggcat tcgtaatcaa cgcctcactc ctcacatcaa     2340
cccgttactt ctattgtaat cataaattca aattcttaga accaagctgt gttccgcact    2400
tttccaccct tttaagcatg gaaaccccga tcgctgggaa aactaacaat gtttggagtg    2460
atgcaaatga aaaaaatagt ggcagccatc gtggtaatcg gtcttgtgtt tatcgcattt    2520
ttttatcttt acagccgatc aggcgatgtg tatcaatcgg tagacgcgga tttgatcaca    2580
ctgtcttcaa gcggccagga agatatcgag attgaaaaaa gacagcacgt caaagatatg    2640
ctggatatta tgaatcaggg aaaacaggtg aagacagaaa aaacatcagc ccctgattac    2700
gaagggacaa tcaagtttca taaagaccgg tatgactcat tcagactatg gattgacggc    2760
agccagcaag ccgttttttt gaaggatggc acatactaca aattaagcaa aaatgataca    2820
aaggcgctgc taaatattat taaaaaagaa gcaaaggatt gaaaatgaaa aagcgaagct    2880
aaccgcttcg ctttttcatt ttattggggc aaaatatctc tcagtgcccg tctgagcatt    2940
ttccccgtcg cattttcgg aatatcgtca agaaacgtaa tggcggcagg ccgcttgtat     3000
tttgccagat gcttttcgca gtgctgcatg atgtcctcct ctgttacccc agagcgtttc    3060
ggcaccacat atccctttac cgcttccccg ctttgggggt ccggcacgcc gatgacaacc    3120
gcctccttga cgtccggatg gctgtacagc acctcctcca cctcccgcgg atacacattg    3180
tatcctccta caatgatcat gtctttttc cggtcaacaa tgtaaaaata gccgcctca     3240 tcccgtcttg ccaagtcccc cgtataaagc cacccgtctt ttaatgcatg ctctgtttcc    3300
atcggcattt tataatagcc cttcatcaca ttggggcctt tcacgatcaa ttcgccgacc    3360
tggtgagcgg gcagctcgcg tccgagcgga tctacgacct tgttttcgac atgtaagata    3420
cttgtcccga tggagcccgg ctttctgccc ctgtcaaacg ggttaaagca cgtgacgggt    3480
gatgcttccg agagcccgta gccttccaaa atggtaacac cgaattttc ttcaaacgcc     3540 gtcagcaacg cgactggcat ggacgcgcct cccgaaatgc acagccggat cgaagaaaaa    3600
tcatctttct ttccgttttc atgctgaaac aagtagttat acattgtagg cacaccggca    3660
aaaatggtcg cctgctgctg cttaacaagc ttaaaaacag atgccggact gaattgaggc    3720
tcaatcaata cagttgcgcc gctcatcagc ggtgcattca tacagacggt taaacaaaac    3780
acgtgaaaca tgggaagagc gcagaccaca ttgtccctct catccattcc caaatagcct    3840
```

-continued

```
gcgacatcgt tggcattgct gtacaaattc tgatgtgtca gcatcgcgcc tttcggtttt      3900
ccagtcgttc ctgacgtata taaaataacc gcggtatcat caggtacagg ttcttggttt      3960
tgtttagcgg cagatgtcgg ccgcaatatt tttgcaaacg ttgtcatttt catcctgacc      4020
tctgggtccg cagcttccgg ctcggcctcc cccgtctggc ataaaatgac gagctcaacc      4080
tttggcagcg attcatgcat gctctcataa agcggcaaaa gctggctaac gcccacgatt      4140
gcctttacat cgccatttgt cagcatataa ccaatttctg tcggcgtgta caacggattg      4200
atgggaacaa ctacgatccc agcttttaaa gcgccaaaaa acgcgatgat aaaatcaggc      4260
gaattgccaa gcagcaaagc taaatggtcc cctttctcca taccggcttc ctgaaggccg      4320
tccgcaaatc gctgaatata ttcattcagc tcttgatacg tcatcatgtg atctttaaac      4380
ctgcatgcga tgctgtcggg cttctcagat gctgtttctt ccaattttga aacaagattc      4440
attctcccac cccttaagtg aatgaatagt cattcattat tgaagccaag ctttcttctc      4500
cattatagag aaacagaaaa aaacactcaa gagcaaaaag ccctgagtgt cagtactgtc      4560
atagtttctt caatgcttcg gcaatcggcg tatctccttc tgtcagatca aaggcccgat      4620
tttccgtatt cttctcatct aaagaggcaa tgaccgtttt tgcaacgtca tcacgggaaa      4680
taaatccccg ctccagatcc ttcgctgctg aaacagttcc cgttccaggc tcattgcgaa      4740
ggcctcccgg acggataatc gtataggtta aaccgctcgc ttccagaatt ttatcagcat      4800
aatgcttggc cacataataa ggcttgagtg cctcattcca attttcacgg ttatgggctt      4860
gcagggcgct gaccataata aaccgtttga ttccggcaat ggccgcagct tcaatggctt      4920
ttgccgctcc atcaagatcc accagcagcg ttttatcata gcctgtgctg ccgccggaac      4980
cggctgtgaa aatgatcgcg tcacaacctt ttgccgcagc ggcgatttct tccgggctgc      5040
cctccagatt cgcaagcaca gcttctgcac cggcagcttc aagagacgct ttctgttctt      5100
cttttctgac catcgctctg atggaatgat caggattatc ttggaataaa gagacgagtc      5160
tttgcccgat ttgtccgttc gctccgatta aaaacacttt catgtgaatc cctcctgcct      5220
ccattatttc aaaaacacaa ccgctctttc aaacgatgtg ttttgcctta gtaaatcaga      5280
tcaaggaaa                                                               5289
```

<210> SEQ ID NO 25
<211> LENGTH: 6064
<212> TYPE: DNA
<213> ORGANISM: artificial sequence
<220> FEATURE:
<223> OTHER INFORMATION: synthesized sequence

<400> SEQUENCE: 25

```
tcgtcaacgc ctgcctcagc aacattgaat ttgcagaaga aaaatggcgg ataaaagact        60
ataatatcaa cagccactta tccggcttta tcaaataaga aaaagacagg cgtttgcctg       120
tcttttcttt tatttcttag cagccggcat ctctttttga agctcgtcca aaatggcatt       180
cgccccgtct acactgcggc gcagagacca caccgcacga tccacgtggt atacatgccc       240 gttttttcact gccttcagtt ttttccaaag acattctttt cgatcgggc gtttaccgtc       300 ggcgtcgagg tcatctgttt ttcctgtcat caggatgatc acatccggat ctgtttttcag      360 cagctgctcc agtgtcattt tcatattcac agagtcgccg ccattgcttg aatcgctatt       420
gcctgacgta ctgattgcat atcggtagcc gacctgtgtt aaaagtctcg atgtaaagaa       480
gttttcatcc ctggccataa tggtatcatt tgtatttccg atcaaaagca cggactggct       540
gttcgcgctg attttctgct ttgtctcgct aagctttttct tcatgcgccg tcagcttttt      600
```

```
ctccatttcc ttctccttgc cgactgcttt tgcaatcgta agcgaagcgt caattgtatc    660
ctgataatca gcatttaaat tattaagtgc aatcgtcggc gctattttt tcagctgatc     720 gtacaccttc ttatgccggg tcgtgtcagc aataattaaa tcgggtttta atgaagcgat    780
tttttccatg cttggctgtg agcgagtgcc gacagatgtg tagccgtcaa ttttcttcag    840
cacatccttg ttgatcagct gcttcgcttt gttgtcatcg gcaacccga caggcgtaat     900 gccgagatca agcagtgtat caataaaacc tagctcaaga acaacaaccc gcttcggatg    960
ctcaggcaca tttgtcttcc ctaaatcatg tgttaccgcc actttatgtt ctttactgtt   1020
ttgattgccg cttgaagacg agcaagcagc cgttaagaca gaaagaagta aaactgtaag  1080
aataatcagt gtttttttca tatgttccag tctctcctgt tggtagtttc tatggttaag  1140
atgtccaaga gtagtataac acggaatgag aatcattatc accaattatt tttaaaatga  1200
gaagagaaag ttcggcttac aggaaaatct tgtttcgcga cacagcagtt cagcagctga  1260
tcatcctgtc cacaaaaaag cttgcagaaa aataacattc tctgcaagct gatcctgtta  1320
aagcttcaca atcactcttc cttgaatgcg attttgcaaa atatctttta acgcacccgg  1380 cgttcttcc aatgatactt ccctgtccac gatggtcagc agctgatcag gcttgagatc   1440
agaagacatg cgctcccaaa cagcggctct gacgtccatc ggacaatata ctgaatcgat  1500
tccgagcagg cttactccgc gaagaataaa aggatacacg gttgccggaa cttcctcc    1560 gccggttaag ccgctcactg cgacagatcc gccgtattga attttgctta aaagcgaggc  1620
aagctgtttt ccgccgactg gatcaaccgc tccctgccat tgctgcttgg acagcgcctt  1680
aagcgttccg tcatagacat cttccctgct gattacttcg cttgcaccaa gctgtttcaa  1740
ataatcagcc gcctcccggt ttccggtact tgccaccaca tcataacccc gcttgttcag  1800
catcgatacc gcaattccgc cgacaccgcc ggttgctcct gtgactagca cgctgccttt  1860
ttccggagac agaccgttct gttcaagccg atgcactgat aacgccgcag taaatcccgc  1920
cgttccgtac accatcgctt cttttaacga aagattctgt ggcaaaggca ccagccagtc  1980
accaggcacc gaagcgtatt cacttaatcc gccatcacgt gagacaccga gctcatagct  2040
tgtcgcgatc acctcatccc cctccgcaaa acgcggatca ttggaagaga cgaccgtacc  2100
cgcagcatca atgcctaaaa taagcggata ctctctgacg atattgcctc ctgcttttcc  2160
ggccagacca tctttgtaat taatgccgga ataagcaact ttaatcagga caccatcctt  2220
cggcaaatcc tctgttgata tggttttcac atggactgaa acatcatcgg catttttttc  2280
tgcctgcaag gcttgaaata acgttgacat tcggcacact cctttcatt tatatcgtaa    2340 ccgaagaacg ttcaaaaaac caaatcatca agccgccatt ttcacttcgc cggcacattg  2400
agacaataat ggacaaatcc ggtatcctct tcatagccgt tttgctcata caagcttctt  2460
gccttccggt tgtggtgctc agtctgaagt gttaaacatt ttgccccgtt ttgccctgca  2520
taatcctttg cggcagaaag cagcggccg ccggctccct ttgtacgcgc atgaggaacg   2580
acaaataagt catttaatat gtatatcctt ttcattgaca cagaagaaaa cgttggatag  2640
agctgggtaa agcctatgaa ttctccattt tcttctgcta tcaaaataac agactcgtga  2700
ttttccaaac gagctttcaa aaaagcctct gccccttgca aatcggatgc ctgtctataa  2760
aattcccgat attggttaaa cagcggcgca atggcggccg catctgatgt ctttgcttgg  2820
cgaatgttca tcttatttct tcctccctct caataatttt ttcattctat cccttttctg  2880
taaagtttat ttttcagaat actttttatca tcatgctttg aaaaaaatatc acgataatat  2940
```

-continued

```
ccattgttct cacggaagca cacgcaggtc atttgaacga attttttcga caggaatttg      3000
ccgggactca ggagcattta acctaaaaaa gcatgacatt tcagcataat gaacatttac      3060
tcatgtctat tttcgttctt ttctgtatga aaatagttat ttcgagtctc tacgaaata       3120 gcgagagatg atatacctaa atagagataa aatcatctca aaaaaatggg tctactaaaa      3180
tattattcca tctattacaa taaattcaca gaatagtctt ttaagtaagt ctactctgaa      3240 ttttttttaaa aggagagggt aaaagagtgtc aacaacatat cctattgtcc tggtacacgg    3300
cctttctggt ttcgatgaca tcgtaggata cccttatttt tatgggattg ccgacgccct      3360
ggagaaagat ggccacaaag tttttacagc ctcactctct gcattcaatt ccaacgaagt      3420
ccgtggcgag caattatggg agttcgtgca aaagattctc aaagagacta aagcaaaaaa      3480
ggtgaatttg atcgggcact cccaaggtcc tcttgcgtgt cgttatgtgg cggccaagca      3540
tgctaaaagt attgcaagtg ttacatctgt gaatggagtg aatcacggta gcgaaatcgc      3600
cgatcttgtc agacggatta tgagaaaaga ttctgtccct gagtatatcg cggacgcggt      3660
aatgaaggct attggcacta taatcagtac ttttagcgga aatagaggaa accctcaaga      3720
cgctatagca gctctggagg ccttaacgac ggaaaacgtg atggaattta acaaaaaata      3780
tcctcaggga ctgccagcaa ttcgtggggg tgaaggtaaa gaagtcgtga acggcgtaca      3840
ctactatagc tttggttctt acatacaggg tctcatcgct ggcgagaagg gaaacttgct      3900
cgatcctacc cacgccgcta tgcgcgtttt atccgcgttt ttttcagaac gtgagaacga      3960
tggtttagta ggacggactt caatgcggct cggcaagtta attaaagacg actacgctga      4020
ggatcattta gatatggtca atcaagttgc ggggttagtt ggacgcgggg aggatataat      4080
tgctatatat acgaatcatg ccaatttttt agcgtcaaaa aagctctaat ctagatacat      4140
aaaaaaccgg ccttggcccc gccggttttt tattattttt cttcctccgc atgttcaatc      4200
cgctccataa tcgacggatg gctccctctg aaaattttaa cgagaacggg cgggttgacc      4260
cggctcagtc ccgtaacggc caagtcctga aacgtctcaa tcgccgcttc ccggtttccg      4320
gtcagctcaa tgccgtaacg gtcggcggcg ttttcctgat accgggagac ggcattcgta      4380
atcaacgcct cactcctcac atcaacccgt tacttctatt gtaatcataa attcaaattc      4440
ttagaaccaa gctgtgttcc gcactttttcc acccttttaa gcatggaaac cccgatcgct      4500
gggaaaacta acaatgtttg gagtgatgca aatgaaaaaa atagtggcag ccatcgtggt      4560
aatcggtctt gtgtttatcg cattttttta tctttacagc cgatcaggcg atgtgtatca      4620
atcggtagac gcggatttga tcacactgtc ttcaagcggc caggaagata tcgagattga      4680
aaaaagacag cacgtcaaag atatgctgga tattatgaat cagggaaaac aggtgaagac      4740
agaaaaaaca tcagcccctg attacgaagg gacaatcaag tttcataaag accggtatga      4800
ctcattcaga ctatggattg acggcagcca gcaagccgtt tttttgaagg atggcacata      4860
ctacaaatta agcaaaaatg atacaaaggc gctgctaaat attattaaaa aagaagcaaa      4920
ggattgaaaa tgaaaaagcg aagctaaccg cttcgctttt tcattttatt ggggcaaaat      4980
atctctcagt gcccgtctga gcattttccc cgtcgcattt ttcggaatat cgtcaagaaa      5040
cgtaatggcg gcaggccgct tgtattttgc cagatgcttt tcgcagtgct gcatgatgtc      5100
ctcctctgtt accccagagc gtttcggcac cacatatccc tttaccgctt ccccgctttg      5160
ggggtccggc acgccgatga caaccgcctc cttgacgtcc ggatggctgt acagcacctc      5220
ctccacctcc cgcggataca cattgtatcc tcctacaatg atcatgtctt ttttccggtc      5280
aacaatgtaa aaatagccgt cctcatcccg tcttgccaag tccccgtat aaagccaccc      5340
```

-continued

```
gtcttttaat gcatgctctg tttccatcgg cattttataa tagcccttca tcacattggg     5400
gcctttcacg atcaattcgc cgacctggtg agcgggcagc tcgcgtccga gcggatctac     5460
gaccttgttt tcgacatgta agatacttgt cccgatggag cccggctttc tgcccctgtc     5520
aaacgggtta aagcacgtga cgggtgatgc ttccgagagc ccgtagcctt ccaaaatggt     5580
aacaccgaat ttttcttcaa acgccgtcag caacgcgact ggcatggacg cgcctcccga     5640
aatgcacagc cggatcgaag aaaaatcatc tttctttccg ttttcatgct gaaacaagta     5700
gttatacatt gtaggcacac cggcaaaaat ggtcgcctgc tgctgcttaa caagcttaaa     5760
aacagatgcc ggactgaatt gaggctcaat caatacagtt gcgccgctca tcagcggtgc     5820
attcatacag acggttaaac aaaacacgtg aaacatggga agagcgcaga ccacattgtc     5880
cctctcatcc attcccaaat agcctgcgac atcgttggca ttgctgtaca aattctgatg     5940
tgtcagcatc gcgcctttcg gttttccagt cgttcctgac gtatataaaa taaccgcggt     6000
atcatcaggt acaggttctt ggttttgttt agcggcagat gtcggccgca atattttgc      6060 aaac                                                                  6064
```

<210> SEQ ID NO 26
<211> LENGTH: 7346
<212> TYPE: DNA
<213> ORGANISM: artificial sequence
<220> FEATURE:
<223> OTHER INFORMATION: synthesized sequence

<400> SEQUENCE: 26

```
ccctgctgac agaaatatcc ggcggtgacc cggagcttca aagcacccgt ctcgtcaacg       60
cctgcctcag caacattgaa tttgcagaag aaaaatggcg gataaaagac tataatatca      120
acagccactt atccggcttt atcaaataag aaaaagacag gcgtttgcct gtctttttctt      180 ttatttctta gcagccggca tctcttttttg aagctcgtcc aaaatggcat tcgccccgtc     240
tacactgcgg cgcagagacc acaccgcacg atccacgtgg tatacatgcc cgttttttcac     300 tgccttcagt ttttttccaaa ggacattctt ttcgatcggg cgtttaccgt cggcgtcgag     360
gtcatctgtt tttcctgtca tcaggatgat cacatccgga tctgttttca gcagctgctc      420
cagtgtcatt ttcatattca cagagtcgcc gccattgctt gaatcgctat tgcctgacgt      480
actgattgca tatcggtagc cgacctgtgt taaaagtctc gatgtaaaga agttttcatc      540
cctggccata atggtatcat ttgtatttcc gatcaaaagc acggactggc tgttcgcgct      600
gattttctgc tttgtctcgc taagctttttc ttcatgcgcc gtcagctttt tctccatttc     660
cttctccttg ccgactgctt ttgcaatcgt aagcgaagcg tcaattgtat cctgataatc      720
agcatttaaa ttattaagtg caatcgtcgg cgctattttt ttcagctgat cgtacacctt      780
cttatgccgg gtcgtgtcag caataattaa atcgggtttt aatgaagcga ttttttccat      840
gcttggctgt gagcgagtgc cgacagatgt gtagccgtca attttcttca gcacatcctt      900
gttgatcagc tgcttcgctt tgttgtcatc ggcaaccccg acaggcgtaa tgccgagatc      960
aagcagtgta tcaataaaac ctagctcaag aacaacaacc cgcttcggat gctcaggcac     1020
atttgtcttc cctaaatcat gtgttaccgc cactttatgt tctttactgt tttgattgcc     1080
gcttgaagac gagcaagcag ccgttaagac agaaagaagt aaaactgtaa gaataatcag     1140
tgtttttttc atatgttcca gtctctcctg ttggtagttt ctatggttaa gatgtccaag     1200
agtagtataa cacggaatga gaatcattat caccaattat ttttaaaatg agaagagaaa     1260
```

```
gttcggctta caggaaaatc ttgtttcgcg acacagcagt tcagcagctg atcatcctgt    1320
ccacaaaaaa gcttgcagaa aaataacatt ctctgcaagc tgatcctgtt aaagcttcac    1380
aatcactctt ccttgaatgc gattttgcaa aatatctttt aacgcacccg gcgtttcttc    1440
caatgatact tccctgtcca cgatggtcag cagctgatca ggcttgagat cagaagacat    1500
gcgctcccaa acagcggctc tgacgtccat cggacaatat actgaatcga ttccgagcag    1560
gcttactccg cgaagaataa aaggatacac ggttgccgga acttctcctc cgccggttaa    1620
gccgctcact gcgacagatc cgccgtattg aattttgctt aaaagcgagg caagctgttt    1680
tccgccgact ggatcaaccg ctccctgcca ttgctgcttg acagcgcct taagcgttcc     1740 gtcatagaca tcttccctgc tgattacttc gcttgcacca agctgtttca aataatcagc    1800
cgcctcccgg tttccggtac ttgccaccac atcataaccc cgcttgttca gcatcgatac    1860
cgcaattccg ccgacaccgc cggttgctcc tgtgactagc acgctgcctt tttccggaga    1920
cagaccgttc tgttcaagcc gatgcactga taacgccgca gtaaatcccg ccgttccgta    1980
caccatcgct tcttttaacg aaagattctg tggcaaaggc accagccagt caccaggcac    2040
cgaagcgtat tcacttaatc cgccatcacg tgagacaccg agctcatagc ttgtcgcgat    2100
cacctcatcc ccctccgcaa aacgcggatc attggaagag acgaccgtac ccgcagcatc    2160
aatgcctaaa ataagcggat actctctgac gatattgcct cctgcttttc cggccagacc    2220
atctttgtaa ttaatgccgg aataagcaac tttaatcagg acaccatcct tcggcaaatc    2280
ctctgttgat atggttttca catggactga aacatcatcg gcattttttt ctgcctgcaa    2340
ggcttgaaat aacgttgaca ttcggcacac tcctttttcat ttatatcgta accgaagaac   2400
gttcaaaaaa ccaaatcatc aagccgccat tttcacttcg ccggcacatt gagacaataa    2460
tggacaaatc cggtatcctc ttcatagccg ttttgctcat acaagcttct tgccttccgg    2520
ttgtggtgct cagtctgaag tgttaaacat tttgccccgt tttgccctgc ataatccttt    2580
gcggcagaaa gcagccggcc gccggctccc tttgtacgcg catgaggaac gacaaataag    2640
tcatttaata tgtatatcct tttcattgac acagaagaaa acgttggata gagctgggta    2700
aagcctatga attctccatt ttcttctgct atcaaaataa cagactcgtg attttccaaa    2760
cgagctttca aaaaagcctc tgccccttgc aaatcggatg cctgtctata aaattcccga    2820
tattggttaa acagcggcgc aatggcggcc gcatctgatg tctttgcttg gcgaatgttc    2880
atcttatttc ttcctccctc tcaataattt tttcattcta tccttttct gtaaagttta     2940 tttttcagaa tacttttatc atcatgcttt gaaaaaatat cacgataata tccattgttc    3000
tcacggaagc acacgcaggt catttgaacg aattttttcg acaggaattt gccgggactc    3060
aggagcattt aacctaaaaa agcatgacat ttcagcataa tgaacattta ctcatgtcta    3120
ttttcgttct tttctgtatg aaaatagtta tttcgagtct ctacggaaat agcgagagat    3180 gatatacctha aatagagata aaatcatctc aaaaaaatgg gtctactaaa atattattcc    3240
atctattaca ataaattcac agaatagtct tttaagtaag tctactctga attttttaa     3300 aaggagaggg taaagagtgt caacaacata tcctattgtc ctggtacacg gcctttctgg    3360
tttcgatgac atcgtaggat acccttattt ttatgggatt gccgacgccc tggagaaaga    3420
tggccacaaa gttttttacag cctcactctc tgcattcaat tccaacgaag tccgtggcga   3480
gcaattatgg gagttcgtgc aaaagattct caaagagact aaagcaaaaa aggtgaattt    3540
gatcgggcac tcccaaggtc ctcttgcgtg tcgttatgtg gcggccaagc atgctaaaag    3600
tattgcaagt gttacatctg tgaatggagt gaatcacggt agcgaaatcg ccgatcttgt    3660
```

```
cagacggatt atgagaaaag attctgtccc tgagtatatc gcggacgcgg taatgaaggc    3720
tattggcact ataatcagta cttttagcgg aaatagagga aaccctcaag acgctatagc    3780
agctctggag gccttaacga cggaaaacgt gatggaattt aacaaaaaat atcctcaggg    3840
actgccagca attcgtgggg gtgaaggtaa agaagtcgtg aacggcgtac actactatag    3900
ctttggttct tacatacagg gtctcatcgc tggcgagaag ggaaacttgc tcgatcctac    3960
ccacgccgct atgcgcgttt tatccgcgtt tttttcagaa cgtgagaacg atggtttagt    4020
aggacggact tcaatgcggc tcggcaagtt aattaaagac gactacgctg aggatcattt    4080
agatatggtc aatcaagttg cggggttagt tggacgcggg gaggatataa ttgctatata    4140
tacgaatcat gccaattttt tagcgtcaaa aaagctctaa tctagataca taaaaaaccg    4200
gccttggccc cgccggtttt ttattatttt tcttcctccg catgttcaat ccgctccata    4260
atcgacggat ggctccctct gaaaatttta acgagaaacg gcgggttgac ccggctcagt    4320
cccgtaacgg ccaagtcctg aaacgtctca atcgccgctt cccggtttcc ggtcagctca    4380
atgccgtaac ggtcggcggc gttttcctga taccgggaga cggcattcgt aatcaacgcc    4440
tcactcctca catcaacccg ttacttctat tgtaatcata aattcaaatt cttagaacca    4500
agctgtgttc cgcactttc caccctttta agcatggaaa ccccgatcgc tgggaaaact    4560
aacaatgttt ggagtgatgc aaatgaaaaa aatagtggca gccatcgtgg taatcggtct    4620
tgtgtttatc gcattttttt atctttacag ccgatcaggc gatgtgtatc aatcggtaga    4680
cgcggatttg atcacactgt cttcaagcgg ccaggaagat atcgagattg aaaaaagaca    4740
gcacgtcaaa gatatgctgg atattatgaa tcagggaaaa caggtgaaga cagaaaaaac    4800
atcagcccct gattacgaag ggacaatcaa gtttcataaa gaccggtatg actcattcag    4860
actatggatt gacggcagcc agcaagccgt ttttttgaag gatggcacat actacaaatt    4920
aagcaaaaat gatacaaagg cgctgctaaa tattattaaa aaagaagcaa aggattgaaa    4980
atgaaaaagc gaagctaacc gcttcgcttt ttcattttat tggggcaaaa tatctctcag    5040
tgcccgtctg agcattttcc ccgtcgcatt tttcggaata tcgtcaagaa acgtaatggc    5100
ggcaggccgc ttgtattttg ccagatgctt ttcgcagtgc tgcatgatgt cctcctctgt    5160
taccccagag cgtttcggca ccacatatcc ctttaccgct tccccgcttt gggggtccgg    5220
cacgccgatg acaaccgcct ccttgacgtc cggatggctg tacagcacct cctccacctc    5280
ccgcggatac acattgtatc ctcctacaat gatcatgtct tttttccggt caacaatgta    5340
aaaatagccg tcctcatccc gtcttgccaa gtcccccgta taaagccacc cgtctttaa    5400 tgcatgctct gtttccatcg gcattttata atagcccttc atcacattgg gccttttcac    5460
gatcaattcg ccgacctggt gagcgggcag ctcgcgtccg agcggatcta cgaccttgtt    5520
ttcgacatgt aagatacttg tcccgatgga gcccggcttt ctgcccctgt caaacgggtt    5580
aaagcacgtg acgggtgatg cttccgagag cccgtagcct tccaaaatgg taacaccgaa    5640 ttttttcttca aacgccgtca gcaacgcgac tggcatggac gcgcctcccg aaatgcacag    5700
ccggatcgaa gaaaaatcat ctttctttcc gttttcatgc tgaaacaagt agttatacat    5760
tgtaggcaca ccggcaaaaa tggtcgcctg ctgctgctta acaagcttaa aaacagatgc    5820
cggactgaat tgaggctcaa tcaatacagt tgcgccgctc atcagcggtg cattcataca    5880
gacggttaaa caaaacacgt gaaacatggg aagagcgcag accacattgt ccctctcatc    5940
cattcccaaa tagcctgcga catcgttggc attgctgtac aaattctgat gtgtcagcat    6000
```

-continued

```
cgcgcctttc ggtttttccag tcgttcctga cgtatataaa ataaccgcgg tatcatcagg      6060
tacaggttct tggttttgtt tagcggcaga tgtcggccgc aatattttttg caaacgttgt      6120 cattttcatc ctgacctctg ggtccgcagc ttccggctcg gcctcccccg tctggcataa      6180
aatgacgagc tcaacctttg gcagcgattc atgcatgctc tcataaagcg gcaaaagctg      6240
gctaacgccc acgattgcct ttacatcgcc atttgtcagc atataaccaa tttctgtcgg      6300
cgtgtacaac ggattgatgg gaacaactac gatcccagct tttaaagcgc caaaaaacgc      6360
gatgataaaa tcaggcgaat tgccaagcag caaagctaaa tggtcccctt tctccatacc      6420
ggcttcctga aggccgtccg caaatcgctg aatatattca ttcagctctt gatacgtcat      6480
catgtgatct ttaaacctgc atgcgatgct gtcgggcttc tcagatgctg tttcttccaa      6540
ttttgaaaca agattcattc tcccacccct taagtgaatg aatagtcatt cattattgaa      6600
gccaagcttt cttctccatt atagagaaac agaaaaaaac actcaagagc aaaaagccct      6660
gagtgtcagt actgtcatag tttcttcaat gcttcggcaa tcggcgtatc tccttctgtc      6720
agatcaaagg cccgatttttc cgtattcttc tcatctaaag aggcaatgac cgttttttgca      6780 acgtcatcac gggaaataaa tccccgctcc agatccttcg ctgctgaaac agttcccgtt      6840
ccaggctcat tgcgaaggcc tcccggacgg ataatcgtat aggttaaacc gctcgcttcc      6900
agaattttat cagcataatg cttggccaca taataaggct tgagtgcctc attccaattt      6960
tcacggttat gggcttgcag ggcgctgacc ataataaacc gtttgattcc ggcaatggcc      7020
gcagcttcaa tggctttttgc cgctccatca agatccacca gcagcgtttt atcatagcct      7080
gtgctgccgc cggaaccggc tgtgaaaatg atcgcgtcac aacctttttgc cgcagcggcg      7140 atttcttccg ggctgccctc cagattcgca agcacagctt ctgcaccggc agcttcaaga      7200
gacgctttct gttcttcttt tctgaccatc gctctgatgg aatgatcagg attatcttgg      7260
aataaagaga cgagtctttg cccgatttgt ccgttcgctc cgattaaaaa cactttcatg      7320
tgaatccctc ctgcctccat tatttc                                           7346
```

<210> SEQ ID NO 27
<211> LENGTH: 10478
<212> TYPE: DNA
<213> ORGANISM: artificial sequence
<220> FEATURE:
<223> OTHER INFORMATION: synthesized sequence

<400> SEQUENCE: 27

```
tcgtcaacgc ctgcctcagc aacattgaat ttgcagaaga aaaatggcgg ataaaagact       60
ataatatcaa cagccactta tccggcttta tcaaataaga aaaagacagg cgtttgcctg      120
tcttttcttt tatttcttag cagccggcat ctcttttttga agctcgtcca aaatggcatt     180
cgccccgtct acactgcggc gcagagacca caccgcacga tccacgtggt atacatgccc      240
gtttttcact gccttcagtt ttttccaaag acattctttt tcgatcgggc gtttaccgtc      300
ggcgtcgagg tcatctgttt ttcctgtcat caggatgatc acatccggat ctgttttcag      360
cagctgctcc agtgtcattt tcatattcac agagtcgccg ccattgcttg aatcgctatt      420
gcctgacgta ctgattgcat atcggtagcc gacctgtgtt aaaagtctcg atgtaaagaa      480
gttttcatcc ctggccataa tggtatcatt tgtatttccg atcaaaagca cggactggct      540
gttcgcgctg attttctgct ttgtctcgct aagctttttct tcatgcgccg tcagctttttt     600 ctccatttcc ttctccttgc cgactgcttt tgcaatcgta agcgaagcgt caattgtatc      660
ctgataatca gcatttaaat tattaagtgc aatcgtcggc gctattttttt tcagctgatc      720
```

```
gtacaccttc ttatgccggg tcgtgtcagc aataattaaa tcgggtttta atgaagcgat     780 ttttttccatg cttggctgtg agcgagtgcc gacagatgtg tagccgtcaa ttttcttcag     840
cacatccttg ttgatcagct gcttcgcttt gttgtcatcg gcaaccccga caggcgtaat     900
gccgagatca agcagtgtat caataaaacc tagctcaaga acaacaaccc gcttcggatg     960
ctcaggcaca tttgtcttcc ctaaatcatg tgttaccgcc actttatgtt ctttactgtt    1020
ttgattgccg cttgaagacg agcaagcagc cgttaagaca gaaagaagta aaactgtaag    1080
aataatcagt gtttttttca tatgttccag tctctcctgt tggtagtttc tatggttaag    1140
atgtccaaga gtagtataac acggaatgag aatcattatc accaattatt tttaaaatga    1200
gaagagaaag ttcggcttac aggaaaatct tgtttcgcga cacagcagtt cagcagctga    1260
tcatcctgtc cacaaaaaag cttgcagaaa aataacattc tctgcaagct gatcctgtta    1320
aagcttcaca atcactcttc cttgaatgcg attttgcaaa atatctttta acgcacccgg    1380
cgtttcttcc aatgatactt ccctgtccac gatggtcagc agctgatcag gcttgagatc    1440
agaagacatg cgctcccaaa cagcggctct gacgtccatc ggacaatata ctgaatcgat    1500
tccgagcagg cttactccgc gaagaataaa aggatacacg gttgccggaa cttctcctcc    1560
gccggttaag ccgctcactg cgacagatcc gccgtattga attttgctta aaagcgaggc    1620
aagctgtttt ccgccgactg gatcaaccgc tccctgccat tgctgcttgg acagcgcctt    1680
aagcgttccg tcatagacat cttccctgct gattacttcg cttgcaccaa gctgtttcaa    1740
ataatcagcc gcctcccggt ttccggtact tgccaccaca tcataacccc gcttgttcag    1800
catcgatacc gcaattccgc cgacaccgcc ggttgctcct gtgactagca cgctgccttt    1860
ttccggagac agaccgttct gttcaagccg atgcactgat aacgccgcag taaatcccgc    1920
cgttccgtac accatcgctt cttttaacga aagattctgt ggcaaaggca ccagccagtc    1980
accaggcacc gaagcgtatt cacttaatcc gccatcacgt gagacaccga gctcatagct    2040
tgtcgcgatc acctcatccc cctccgcaaa acgcggatca ttggaagaga cgaccgtacc    2100
cgcagcatca atgcctaaaa taagcggata ctctctgacg atattgcctc ctgcttttcc    2160
ggccagacca tctttgtaat taatgccgga ataagcaact ttaatcagga caccatcctt    2220
cggcaaatcc tctgttgata tggttttcac atggactgaa acatcatcgg cattttttc     2280 tgcctgcaag gcttgaaata acgttgacat tcggcacact cctttccatt tatatcgtaa    2340
ccgaagaacg ttcaaaaaac caaatcatca agccgccatt ttcacttcgc cggcacattg    2400
agacaataat ggacaaatcc ggtatcctct tcatagccgt tttgctcata caagcttctt    2460
gccttccggt tgtggtgctc agtctgaagt gttaaacatt ttgccccgtt ttgccctgca    2520
taatcctttg cggcagaaag cagccggccg ccggctccct ttgtacgcgc atgaggaacg    2580
acaaataagt catttaatat gtatatcctt ttcattgaca cagaagaaaa cgttggatag    2640
agctgggtaa agcctatgaa ttctccattt tcttctgcta tcaaaataac agactcgtga    2700
ttttccaaac gagctttcaa aaaagcctct gccccttgca aatcggatgc ctgtctataa    2760
aattcccgat attggttaaa cagcggcgca atggcggccg catctgatgt ctttgcttgg    2820
cgaatgttca tcttatttct tcctccctct caataatttt ttcattctat cccttttctg    2880
taaagtttat ttttcagaat actttttatca tcatgctttg aaaaaatatc acgataatat    2940
ccattgttct cacggaagca cacgcaggtc atttgaacga atttttttcga caggaatttg    3000 ccgggactca ggagcattta acctaaaaaa gcatgacatt tcagcataat gaacatttac    3060
```

-continued

```
tcatgtctat tttcgttctt ttctgtatga aaatagttat ttcgagtctc tacggaaata   3120
gcgagagatg atatacctaa atagagataa aatcatctca aaaaaatggg tctactaaaa   3180
tattattcca tctattacaa taaattcaca gaatagtctt ttaagtaagt ctactctgaa   3240 ttttttttaaa aggagagggt aaagagtgtc aacaacatat cctattgtcc tggtacacgg   3300
cctttctggt ttcgatgaca tcgtaggata cccttatttt tatgggattg ccgacgccct   3360
ggagaaagat ggccacaaag tttttacagc ctcactctct gcattcaatt ccaacgaagt   3420
ccgtggcgag caattatggg agttcgtgca aaagattctc aaagagacta aagcaaaaaa   3480
ggtgaatttg atcgggcact cccaaggtcc tcttgcgtgt cgttatgtgg cggccaagca   3540
tgctaaaagt attgcaagtg ttacatctgt gaatggagtg aatcacggta gcgaaatcgc   3600
cgatcttgtc agacggatta tgagaaaaga ttctgtccct gagtatatcg cggacgcggt   3660
aatgaaggct attggcacta taatcagtac ttttagcgga aatagaggaa accctcaaga   3720
cgctatagca gctctggagg ccttaacgac ggaaaacgtg atggaattta acaaaaaata   3780
tcctcaggga ctgccagcaa ttcgtggggg tgaaggtaaa gaagtcgtga acggcgtaca   3840
ctactatagc tttggttctt acatacaggg tctcatcgct ggcgagaagg gaaacttgct   3900
cgatcctacc cacgccgcta tgcgcgtttt atccgcgttt ttttcagaac gtgagaacga   3960
tggtttagta ggacggactt caatgcggct cggcaagtta attaaagacg actacgctga   4020
ggatcattta gatatggtca atcaagttgc ggggttagtt ggacgcgggg aggatataat   4080
tgctatatat acgaatcatg ccaatttttt agcgtcaaaa aagctctaat ctagatacat   4140
aaaaaaccgg ccttggcccc gccggttttt tattattttt cttcctccgc atgttcaatc   4200
cgctccataa tcgacggatg gctccctctg aaaattttaa cgagaaacgg cgggttgacc   4260
cggctcagtc ccgtaacggc caagtcctga aacgtctcaa tcgccgcttc ccggtttccg   4320
gtcagctcaa tgccgtaacg gtcggcggcg ttttcctgat accgggagac ggcattcgta   4380
atcaacgcct cactcctcac atcaacccgt tacttctatt gtaatcataa attcaaattc   4440
ttagaaccaa gctgtgttcc gcacttttcc acccttttaa gcatggaaac cccgatcgct   4500
gggaaaacta acaatgtttg gagtgatgca aatgaaaaaa atagtggcag ccatcgtggt   4560
aatcggtctt gtgtttatcg cattttttta tctttacagc cgatcaggcg atgtgtatca   4620
atcggtagac gcggatttga tcacactgtc ttcaagcggc caggaagata tcgagattga   4680
aaaaagacag cacgtcaaag atatgctgga tattatgaat cagggaaaac aggtgaagac   4740
agaaaaaaca tcagcccctg attacgaagg gacaatcaag tttcataaag accggtatga   4800
ctcattcaga ctatggattg acggcagcca gcaagccgtt tttttgaagg atggcacata   4860
ctacaaatta agcaaaaatg atacaaaggc gctgctaaat attattaaaa aagaagcaaa   4920
ggattgaaaa tgaaaaagcg aagctaaccg cttcgctttt tcattttatt ggggcaaaat   4980
atctctcagt gcccgtctga gcattttccc cgtcgcattt ttcggaatat cgtcaagaaa   5040
cgtaatggcg gcaggccgct tgtattttgc cagatgcttt tcgcagtgct gcatgatgtc   5100
ctcctctgtt accccagagc gtttcggcac cacatatccc tttaccgctt ccccgctttg   5160
ggggtccggc acgccgatga caaccgcctc cttgacgtcc ggatggctgt acagcacctc   5220
ctccacctcc cgcggataca cattgtatcc tcctacaatg atcatgtctt ttttccggtc   5280
aacaatgtaa aaatagccgt cctcatcccg tcttgccaag tccccgtat aaagccaccc   5340 gtcttttaat gcatgctctg tttccatcgg cattttataa tagcccttca tcacattggg   5400
gcctttcacg atcaattcgc cgacctggtg agcgggcagc tcgcgtccga gcggatctac   5460
```

-continued

```
gaccttgttt tcgacatgta agatacttgt cccgatggag cccggctttc tgccctgtc     5520 aaacgggtta aagcacgtga cgggtgatgc ttccgagagc ccgtagcctt ccaaaatggt     5580
aacaccgaat ttttcttcaa acgccgtcag caacgcgact ggcatggacg cgcctcccga     5640
aatgcacagc cggatcgaag aaaaatcatc tttctttccg ttttcatgct gaaacaagta     5700
gttatacatt gtaggcacac cggcaaaaat ggtcgcctgc tgctgcttaa caagcttaaa     5760
aacagatgcc ggactgaatt gaggctcaat caatacagtt cgccgctca tcagcggtgc     5820 attcatacag acggttaaac aaaacacgtg aaacatggga agagcgcaga ccacattgtc     5880
cctctcatcc attcccaaat agcctgcgac atcgttggca ttgctgtaca aattctgatg     5940
tgtcagcatc gcgcctttcg gtttttccagt cgttcctgac gtatataaaa taaccgcggt     6000
atcatcaggt acaggttctt ggttttgttt agcggcagat gtcggccgca atattttttgc     6060 aaacgttgtc attttcatcc tgacctctgg gtccgcagct tccggctcgg cctcccccgt     6120
ctggcataaa atgacgagct caacctttgg cagcgattca tgcatgctct cataaagcgg     6180
caaaagctgg ctaacgccca cgattgcctt tacatcgcca tttgtcagca tataaccaat     6240
ttctgtcggc gtgtacaacg gattgatggg aacaactacg atcccagctt ttaaagcgcc     6300
aaaaaacgcg atgataaaat caggcgaatt gccaagcagc aaagctaaat ggtcccctttt     6360 ctccataccg gcttcctgaa ggccgtccgc aaatcgctga atatattcat tcagctcttg     6420
atacgtcatc atgtgatctt taaacctgca tgcgatgctg tcgggcttct cagatgctgt     6480
ttcttccaat tttgaaacaa gattcattct cccacccctt aagtgaatga atagtcattc     6540
attattgaag ccaagctttc ttctccatta tagagaaaca gaaaaaaaca ctcaagagca     6600
aaaagccctg agtgtcagta ctgtcatagt ttcttcaatg cttcggcaat cggcgtatct     6660
ccttctgtca gatcaaaggc ccgatttttcc gtattcttct catctaaaga ggcaatgacc     6720
gtttttgcaa cgtcatcacg ggaaataaat ccccgctcca gatccttcgc tgctgaaaca     6780
gttcccgttc caggctcatt gcgaaggcct cccggacgga taatcgtata ggttaaaccg     6840
ctcgcttcca gaattttatc agcataatgc ttggccacat aataaggctt gagtgcctca     6900
ttccaatttt cacggttatg ggcttgcagg gcgctgacca taataaaccg tttgattccg     6960
gcaatggccg cagcttcaat ggcttttgcc gctccatcaa gatccaccag cagcgtttta     7020
tcatagcctg tgctgccgcc ggaaccggct gtgaaaatga tcgcgtcaca accttttgcc     7080
gcagcggcga tttcttccgg gctgccctcc agattcgcaa gcacagcttc tgcaccggca     7140
gcttcaagag acgctttctg ttcttctttt ctgaccatcg ctctgatgga atgatcagga     7200
ttatcttgga ataaagagac gagtctttgc ccgatttgtc cgttcgctcc gattaaaaac     7260
actttcatgt gaatccctcc tgcctccatt atttcaaaaa cacaaccgct ctttcaaacg     7320
atgtgttttg ccttagtaaa tcagatcaag gaaatcctct ttcgtaatgt tcccaaagta     7380
atgcttgaga ttcacacctt cgagcacatc agcgatgacg ctgcgttcgt attgttttcc     7440
gaccagcagg ttttcaattt cagatacatc accgacaccg aagaaatctc cgaagatttt     7500
gcagtcctcg attttgcctt tcttgacttc caggtgcaaa tcgatcgatc caaccggata     7560
acgcttcgaa tgattaaggt aaatttttgg tgagcggccg tagttccaat cccaattctg     7620
atagcgctct ttcgaaattt gatgaatggt ctcccaatct ttttccgtca gcttatactc     7680
cggcacgttt ccaacgtcgt ttgtgttaaa aatatggcga agcaaatggc tgcggaattc     7740
ttcggtggtc attttatcat cgagaaactc actgatgttt gccactcggc ttctgatcga     7800
```

```
tttgatgcct tttgattcaa ttttatcctt tttcacctتت aatgctgata caacatgatc    7860
aatggctgaa tcaaacatga gggtgccgtg gctgaaaata cggcctttcg ttgcaaactg    7920
agcgtttccg gatattttcc ggccatctac tacaatgtcg ttccggccgc ttaattcggc    7980
ttcaacccca agctgatgta acgcctgaat cactggctca gtgaattttt taaagttatg    8040
aaagctgtcc ccgtcatcct tggtaataaa gctgaagttc aagttcccca gatcatggta    8100
cacagcgccc ccgcctgata aacggcggac gacgataatc ccgttttcct caacatattt    8160
tgtattgatt tcttctattg tattttggtt tttcccaatg ataatagacg gttgattcac    8220
ataaaagagc aaatattgct gttcagggtc taaatgcttt acacagtact cctcgatagc    8280
aagattgatc cgcggatcat tgatattttg attgtctata aataacatgg tgctcctcct    8340
ttatccttcc cacacaaaac ctgatttcgc aatattcact tctccgttaa aaacggtttt    8400
cgcttctttg cgaaggttgt catgcacgcc aaaatgcggc aaatgtgtca gcagcagttc    8460
tcccgctccg gcttcttttg caatgcgccc agcttccagg ctgttcatat ggcctgcact    8520
tgttccgtct tgatcggcat aaaaattgca ttctgagatc aataaatcag catctttcga    8580
aaacggtata aatgaatcct gatagctgga atcagcagta taaacgacag tgtggctgcc    8640
gtcagtaatc cgcatggcat agcacgtcac cgggtgaatc gtttttaaaa aggtgatcgt    8700
aaacggaccg gcagtcagcg gctgatccgg ctgataggcg atccctttg tatgtgtttt    8760 atatgtaagc ttttgaaact gttctatatc agcatcatgt ccgtaaatcg gaagcgtatg    8820
ctctcctttg ccgagaaacg aaccgacttg cttggcaaat tgcagcggtc cgatatcagc    8880
gatatggtca tggtgataat gagacagaac gaccgcatcc agcttttccg ccggcacata    8940
tccgaacagc ttagacaata cggcactgcc gcaatcaaca agcagagagt aatcacctga    9000
ctgaaacaaa tagcctgacg tcgcttcatt tgcggccgga aaaccgccat agcatccgat    9060
aactgtaact ttcataatgt cctcctatct tttcaaaaaa attggtcctc cttcaatata    9120 cccattttc ttgaaaaaag catgttttaa acattgtatc aaaacagtta ttgatttttg    9180
taatctgtta tattacaatg aaatcactac aaaggggaaa gagggattgg ttatgctggg    9240
gaaaatcaca gaattttta gaaacctgcc ttcgaaaaag tgtgcggaat gcggaaaaaa    9300
gatagaagag cagcatgagt gttatggtaa tatctgcaat gactgtataa aagtaaacga    9360
tttgtaatga gcgaaaatcc cgcgccttac gcgtgggatt ttcttatttt ttcacatatc    9420
tcttaatttt gaaataatag tcaggttagg tcaaagctca cctgttttta gataattctg    9480
gtgattatca taatgtcatt gaatattctt tattttcgaa atataattta ctatagacga    9540
attgatttct tatctattat aatttgatct aatagtgaga ttaaatatat gtctattcat    9600
gatatatgtt gatactttgt tttttgggag gtaatctatg aaaagaatta agtttggatt    9660
agccacacaa atattcgttg gacttattct aggtgtcatt gttggcgtca tttggtatgg    9720
caacccagca ttgcctactt acctgcagcc aatcggggat ctcttttac gcttaatcaa    9780 aatgatagtg attcctattg ttgtctccag cttaatcatc ggtgtagccg gtgcaggaaa    9840
tggaaagcaa gtcggtaaat taggcttcag aacgattctg tacttcgaga tcatcacgac    9900
ttttgccatt attctcggac tagcccttgc aaacatcttc catccgggta caggagttaa    9960
tatacacgaa gctcaaaaat cggacatcag tcaatatgtt gaaactgaaa aagaacaaag   10020
taataaatca gtggcggaaa cgttcctcca tattgtgccg acaaacttct tccagtcatt   10080
ggtcgaaggg gatcttctag ccatcatctg ctttacagta ctatttgcat ggggtatttc   10140
cgcgatcggt gaaagaggca agcctgtatt agccttttt gaaggtgtat cccatgccat   10200
```

-continued

```
gttccacgtt gtaaaccttg tgatgaaagt ggcgccattc ggcgttttcg ctcttatcgg    10260
agtgactgtg tctaaattcg gactcggttc tcttatctct ctcggaaagc tcgtcggatt    10320
ggtttatgtc gcgcttgctt tcttcttaat tgttattttc gggattgtcg caaaaattgc    10380
cggcatcagc atcttcaagt tccttgctta catgaaggac gaaatcttac tggcgttcag    10440
tacgtccagc tctgaaacgg ttcttccgcg tatcatgg                            10478
```

```
<210> SEQ ID NO 28
<211> LENGTH: 7549
<212> TYPE: DNA
<213> ORGANISM: artificial sequence
<220> FEATURE:
<223> OTHER INFORMATION: synthesized sequence

<400> SEQUENCE: 28
cacgataata tccattgttc tcacggaagc acacgcaggt catttgaacg aattttttcg      60
acaggaattt gccgggactc aggagcattt aacctaaaaa agcatgacat ttcagcataa     120
tgaacattta ctcatgtcta ttttcgttct tttctgtatg aaaatagtta tttcgagtct     180
ctacggaaat agcgagagat gatataccta aatagagata aaatcatctc aaaaaaatgg     240
gtctactaaa atattattcc atctattaca ataaattcac agaatagtct tttaagtaag     300
tctactctga atttttttaa aaggagaggg taaagagtgt caacaacata tcctattgtc     360
ctggtacacg gcctttctgg tttcgatgac atcgtaggat acccttattt ttatgggatt     420
gccgacgccc tggagaaaga tggccacaaa gtttttacag cctcactctc tgcattcaat     480
tccaacgaag tccgtggcga gcaattatgg gagttcgtgc aaaagattct caaagagact     540
aaagcaaaaa aggtgaattt gatcgggcac tcccaaggtc ctcttgcgtg tcgttatgtg     600
gcggccaagc atgctaaaag tattgcaagt gttacatctg tgaatggagt gaatcacggt     660
agcgaaatcg ccgatcttgt cagacggatt atgagaaaag attctgtccc tgagtatatc     720
gcggacgcgg taatgaaggc tattggcact ataatcagta ctttttagcgg aaatagagga     780 aaccctcaag acgctatagc agctctggag gccttaacga cggaaaacgt gatggaattt     840
aacaaaaaat atcctcaggg actgccagca attcgtgggg gtgaaggtaa agaagtcgtg     900
aacggcgtac actactatag ctttggttct tacatacagg gtctcatcgc tggcgagaag     960
ggaaacttgc tcgatcctac ccacgccgct atgcgcgttt tatccgcgtt tttttcagaa    1020
cgtgagaacg atggtttagt aggacggact tcaatgcggc tcggcaagtt aattaaagac    1080
gactacgctg aggatcattt agatatggtc aatcaagttg cggggttagt tggacgcggg    1140
gaggatataa ttgctatata tacgaatcat gccaattttt tagcgtcaaa aaagctctaa    1200
tctagataca taaaaaaccg gccttggccc cgccggtttt ttattatttt tcttcctccg    1260
catgttcaat ccgctccata atcgacggat ggctccctct gaaaatttta acgagaaacg    1320
gcgggttgac ccggctcagt cccgtaacgg ccaagtcctg aaacgtctca atcgccgctt    1380
cccggtttcc ggtcagctca atgccgtaac ggtcggcggc gttttcctga taccgggaga    1440
cggcattcgt aatcaacgcc tcactcctca catcaacccg ttacttctat tgtaatcata    1500
aattcaaatt cttagaacca agctgtgttc cgcacttttc cacccttta agcatggaaa     1560 ccccgatcgc tgggaaaact aacaatgttt ggagtgatgc aaatgaaaaa aatagtggca    1620
gccatcgtgg taatcggtct tgtgtttatc gcattttttt atctttacag ccgatcaggc    1680
gatgtgtatc aatcggtaga cgcggatttg atcacactgt cttcaagcgg ccaggaagat    1740
```

```
atcgagattg aaaaaagaca gcacgtcaaa gatatgctgg atattatgaa tcagggaaaa      1800
caggtgaaga cagaaaaaac atcagccct gattacgaag ggacaatcaa gtttcataaa       1860
gaccggtatg actcattcag actatggatt gacggcagcc agcaagccgt ttttttgaag      1920
gatggcacat actacaaatt aagcaaaaat gatacaaagg cgctgctaaa tattattaaa      1980
aaagaagcaa aggattgaaa atgaaaaagc gaagctaacc gcttcgcttt ttcattttat      2040
tggggcaaaa tatctctcag tgcccgtctg agcattttcc ccgtcgcatt tttcggaata      2100
tcgtcaagaa acgtaatggc ggcaggccgc ttgtatttttg ccagatgctt ttcgcagtgc      2160
tgcatgatgt cctcctctgt taccccagag cgtttcggca ccacatatcc ctttaccgct      2220
tccccgcttt gggggtccgg cacgccgatg acaaccgcct ccttgacgtc cggatggctg      2280
tacagcacct cctccacctc ccgcggatac acattgtatc ctcctacaat gatcatgtct      2340
tttttccggt caacaatgta aaaatagccg tcctcatccc gtcttgccaa gtccccgta      2400 taaagccacc cgtcttttaa tgcatgctct gtttccatcg gcattttata atagcccttc      2460
atcacattgg ggcctttcac gatcaattcg ccgacctggt gagcgggcag ctcgcgtccg      2520
agcggatcta cgaccttgtt ttcgacatgt aagatacttg tcccgatgga gcccggcttt      2580
ctgcccctgt caaacgggtt aaagcacgtg acgggtgatg cttccgagag cccgtagcct      2640
tccaaaatgg taacaccgaa tttttcttca aacgccgtca gcaacgcgac tggcatggac      2700
gcgcctcccg aaatgcacag ccggatcgaa gaaaaatcat ctttctttcc gttttcatgc      2760
tgaaacaagt agttatacat tgtaggcaca ccggcaaaaa tggtcgcctg ctgctgctta      2820
acaagcttaa aaacagatgc cggactgaat tgaggctcaa tcaatacagt tgcgccgctc      2880
atcagcggtg cattcataca gacggttaaa caaaacacgt gaaacatggg aagagcgcag      2940
accacattgt ccctctcatc cattcccaaa tagcctgcga catcgttggc attgctgtac      3000
aaattctgat gtgtcagcat cgcgcctttc ggttttccag tcgttcctga cgtatataaa      3060
ataaccgcgg tatcatcagg tacaggttct tggttttgtt tagcggcaga tgtcggccgc      3120 aatattttttg caaacgttgt cattttcatc ctgacctctg ggtccgcagc ttccggctcg      3180
gcctcccccg tctggcataa aatgacgagc tcaacctttg gcagcgattc atgcatgctc      3240
tcataaagcg gcaaaagctg gctaacgccc acgattgcct ttacatcgcc atttgtcagc      3300
atataaccaa tttctgtcgg cgtgtacaac ggattgatgg gaacaactac gatcccagct      3360
tttaaagcgc caaaaaacgc gatgataaaa tcaggcgaat tgccaagcag caaagctaaa      3420
tggtcccctt tctccatacc ggcttcctga aggccgtccg caaatcgctg aatatattca      3480
ttcagctctt gatacgtcat catgtgatct ttaaacctgc atgcgatgct gtcgggcttc      3540
tcagatgctg tttcttccaa ttttgaaaca agattcattc tcccaccct taagtgaatg       3600 aatagtcatt cattattgaa gccaagcttt cttctccatt atagagaaac agaaaaaaac       3660
actcaagagc aaaaagccct gagtgtcagt actgtcatag tttcttcaat gcttcggcaa      3720
tcggcgtatc tccttctgtc agatcaaagg cccgattttc cgtattcttc tcatctaaag      3780
aggcaatgac cgtttttgca acgtcatcac gggaaataaa tccccgctcc agatccttcg      3840
ctgctgaaac agttcccgtt ccaggctcat tgcgaaggcc tcccgacgg ataatcgtat       3900 aggttaaacc gctcgcttcc agaattttat cagcataatg cttggccaca taataaggct      3960
tgagtgcctc attccaattt tcacggttat gggcttgcag ggcgctgacc ataataaacc      4020
gtttgattcc ggcaatggcc gcagcttcaa tggctttttgc cgctccatca agatccacca      4080
gcagcgtttt atcatagcct gtgctgccgc cggaaccggc tgtgaaaatg atcgcgtcac      4140
```

-continued

```
aaccttttgc cgcagcggcg atttcttccg ggctgccctc cagattcgca agcacagctt    4200
ctgcaccggc agcttcaaga gacgctttct gttcttcttt tctgaccatc gctctgatgg    4260
aatgatcagg attatcttgg aataaagaga cgagtctttg cccgatttgt ccgttcgctc    4320
cgattaaaaa cactttcatg tgaatccctc ctgcctccat tatttcaaaa acacaaccgc    4380
tctttcaaac gatgtgtttt gccttagtaa atcagatcaa ggaaatcctc tttcgtaatg    4440
ttcccaaagt aatgcttgag attcacacct tcgagcacat cagcgatgac gctgcgttcg    4500
tattgttttc cgaccagcag gttttcaatt tcagatacat caccgacacc gaagaaatct    4560
ccgaagattt tgcagtcctc gattttgcct ttcttgactt ccaggtgcaa atcgatcgat    4620
ccaaccggat aacgcttcga atgattaagg ttaaattttg gtgagcggcc gtagttccaa    4680
tcccaattct gatagcgctc tttcgaaatt tgatgaatgg tctcccaatc tttttccgtc    4740
agcttatact ccggcacgtt tccaacgtcg tttgtgttaa aaatatggcg aagcaaatgg    4800
ctgcggaatt cttcggtggt cattttatca tcgagaaact cactgatgtt tgccactcgg    4860
cttctgatcg atttgatgcc ttttgattca attttatcct ttttcacctt taatgctgat    4920
acaacatgat caatggctga atcaaacatg agggtgccgt ggctgaaaat acggcctttc    4980
gttgcaaact gagcgtttcc ggatattttc cggccatcta ctacaatgtc gttccggccg    5040
cttaattcgg cttcaacccc aagctgatgt aacgcctgaa tcactggctc agtgaatttt    5100
ttaaagttat gaaagctgtc cccgtcatcc ttggtaataa agctgaagtt caagttcccc    5160
agatcatggt acacagcgcc cccgcctgat aaacggcgga cgacgataat cccgtttttcc    5220 tcaacatatt ttgtattgat ttcttctatt gtattttggt ttttcccaat gataatagac    5280
ggttgattca cataaaagag caaatattgc tgttcagggt ctaaatgctt tacacagtac    5340
tcctcgatag caagattgat ccgcggatca ttgatatttt gattgtctat aaataacatg    5400
gtgctcctcc tttatccttc ccacacaaaa cctgatttcg caatattcac ttctccgtta    5460
aaaacggttt tcgcttcttt gcgaaggttg tcatgcacgc caaaatgcgg caaatgtgtc    5520
agcagcagtt ctcccgctcc ggcttctttt gcaatgcgcc cagcttccag gctgttcata    5580
tggcctgcac ttgttccgtc ttgatcggca taaaaattgc attctgagat caataaatca    5640
gcatctttcg aaaacggtat aaatgaatcc tgatagctgg aatcagcagt ataaacgaca    5700
gtgtggctgc cgtcagtaat ccgcatggca tagcacgtca ccgggtgaat cgttttaaa    5760 aaggtgatcg taaacggacc ggcagtcagc ggctgatccg gctgataggc gatccctttt    5820
gtatgtgttt tatatgtaag cttttgaaac tgttctatat cagcatcatg tccgtaaatc    5880
ggaagcgtat gctctccttt gccgagaaac gaaccgactt gcttggcaaa ttgcagcggt    5940
ccgatatcag cgatatggtc atggtgataa tgagacagaa cgaccgcatc cagctttttcc    6000 gccggcacat atccgaacag cttagacaat acggcactgc cgcaatcaac aagcagagag    6060
taatcacctg actgaaacaa atagcctgac gtcgcttcat ttgcggccgg aaaaccgcca    6120
tagcatccga taactgtaac tttcataatg tcctcctatc ttttcaaaaa aattggtcct    6180
ccttcaatat acccattttt cttgaaaaaa gcatgtttta aacattgtat caaaacagtt    6240
attgattttt gtaatctgtt atattacaat gaaatcacta caaaggggaa agagggattg    6300
gttatgctgg ggaaatcac agaatttttt agaaacctgc cttcgaaaaa gtgtgcggaa    6360
tgcggaaaaa agatagaaga gcagcatgag tgttatggta atatctgcaa tgactgtata    6420
aaagtaaacg atttgtaatg agcgaaaatc ccgcgcctta cgcgtgggat tttcttatttt    6480
```

```
tttcacatat ctcttaattt tgaaataata gtcaggttag gtcaaagctc acctgttttt      6540
agataattct ggtgattatc ataatgtcat tgaatattct ttattttcga aatataattt      6600
actatagacg aattgatttc ttatctatta taatttgatc taatagtgag attaaatata      6660
tgtctattca tgatatatgt tgatactttg ttttttggga ggtaatctat gaaaagaatt      6720
aagtttggat tagccacaca aatattcgtt ggacttattc taggtgtcat tgttggcgtc      6780
atttggtatg gcaacccagc attgcctact tacctgcagc caatcgggga tctcttttta      6840
cgcttaatca aaatgatagt gattcctatt gttgtctcca gcttaatcat cggtgtagcc      6900
ggtgcaggaa atggaaagca agtcggtaaa ttaggcttca gaacgattct gtacttcgag      6960
atcatcacga cttttgccat tattctcgga ctagcccttg caaacatctt ccatccgggt      7020
acaggagtta atatacacga agctcaaaaa tcggacatca gtcaatatgt tgaaactgaa      7080
aaagaacaaa gtaataaatc agtggcggaa acgttcctcc atattgtgcc gacaaacttc      7140
ttccagtcat tggtcgaagg ggatcttcta gccatcatct gctttacagt actatttgca      7200
ttgggtattt ccgcgatcgg tgaaagaggc aagcctgtat tagccttttt tgaaggtgta      7260
tcccatgcca tgttccacgt tgtaaacctt gtgatgaaag tggcgccatt cggcgttttc      7320
gctcttatcg gagtgactgt gtctaaattc ggactcggtt ctcttatctc tctcggaaag      7380
ctcgtcggat tggtttatgt cgcgcttgct ttcttcttaa ttgttatttt cgggattgtc      7440
gcaaaaattg ccggcatcag catcttcaag ttccttgctt acatgaagga cgaaatctta      7500
ctggcgttca gtacgtccag ctctgaaacg gttcttccgc gtatcatgg                 7549
```

```
<210> SEQ ID NO 29
<211> LENGTH: 2596
<212> TYPE: DNA
<213> ORGANISM: artificial sequence
<220> FEATURE:
<223> OTHER INFORMATION: synthesized sequence

<400> SEQUENCE: 29
```

```
gctatcaaaa taacagactc gtgattttcc aaacgagctt tcaaaaaagc ctctgcccct        60
tgcaaatcgg atgcctgtct ataaaattcc cgatattggt taaacagcgg cgcaatggcg       120
gccgcatctg atgtctttgc ttggcgaatg ttcatcttat ttcttcctcc ctctcaataa       180 tttttttcatt ctatcccttt tctgtaaagt ttattttttca gaatactttt atcatcatgc     240
tttgaaaaaa tatcacgata atatccattg ttctcacgga agcacacgcg ctgataaaca       300
gctgacatca actaaaagtt tcattaaata cttttgaaaaa agttgttgac ttaaaagaag      360
ctaaatgtta tagtaattgt acagaatagt cttttaagta agtctactct gaattttttt      420
aaaaggagag ggtaaagagt gagaagcaaa aaattgtgga tcagcttgtt gtttgcgtta      480
acgttaatct ttacgatggc gttcagcaac atgtctgcgc aggctgctga agaagcaaaa      540
gaaaaatatt taattggctt taatgagcag gaagctgtca gtgagtttgt agaacaagta      600
gaggcaaatg acgaggtcgc cattctctct gaggaagagg aagtcgaaat tgaattgctt      660
catgaatttg aaacgattcc tgttttatcc gttgagttaa gcccagaaga tgtggacgcg      720
cttgaactcg atccagcgat ttcttatatt gaagaggatg cagaagtaac gacaatgcaa      780
caaacagtgc catgggggaat tactcgtgtg caagcccag ctgttcataa ccgtggaatt       840
acaggttctg gtgtaagagt tgctatcctc gattcaggta tttccacaca tgaagactta      900
aatgttcgtg gtggcgttag ctttgtacca ggggaaccaa cgtatgctga tttaaatggg      960
catggcacgc atgtggctgg gacggtagct gctttaaaca attcgattgg cgttgttggc     1020
```

-continued

```
gtagcaccgt cagcggatct atacgctgtt aaagtattag gggcgaatgg tagaggttcg    1080
gtcagcggga ttgcccaagg attggaatgg gcagcacaaa ataacatgca cattgctaat    1140
atgagtttag gaacagatgc accaagttct cacttgagc gtgctgttaa ttatgcgact     1200
tctagagatg ttcttgttat tgcggcaact gggaataacg gttctggctc agtaggctat    1260
ccggcccgtt atgcgaacgc aatggcagtc ggagctactg accaaaacaa cagacgcgcc    1320
aacttttcac agtatggcac ggggattgac attgtcgcac caggtgtaaa cgtgcagagc    1380
acatacccag gtaaccgtta tgtgagcatg aacggtacat cgatggctac tcctcatgtt    1440
gcaggtgcag cagcccttgt taaacaacgc tatccatctt ggaatgcgac tcaaatccgc    1500
gaccatctaa agaatacggc aacgaattta ggaaactctt cacaatttgg aagcggactt    1560
gtcaatgcag aagcggcaac acgctaatct agatacataa aaaaccggcc ttggccccgc    1620
cggtttttta ttattttct tcctccgcat gttcaatccg ctccataatc gacggatggc     1680
tccctctgaa aatttaacg agaaacggcg ggttgacccg gctcagtccc gtaacggcca     1740
agtcctgaaa cgtctcaatc gccgcttccc ggtttccggt cagctcaatg ccgtaacggt    1800
cggcggcgtt ttcctgatac cgggagacgg cattcgtaat caacgcctca ctcctcacat    1860
caacccgtta cttctattgt aatcataaat tcaaattctt agaaccaagc tgtgttccgc    1920
acttttccac ccttttaagc atggaaaccc cgatcgctgg gaaaactaac aatgtttgga    1980
gtgatgcaaa tgaaaaaaat agtggcagcc atcgtggtaa tcggtcttgt gtttatcgca    2040 ttttttatc tttacagccg atcaggcgat gtgtatcaat cggtagacgc ggatttgatc     2100
acactgtctt caagcggcca ggaagatatc gagattgaaa aaagacagca cgtcaaagat    2160
atgctggata ttatgaatca gggaaaacag gtgaagacag aaaaaacatc agccctgat    2220 tacgaaggga caatcaagtt tcataaagac cggtatgact cattcagact atggattgac    2280
ggcagccagc aagccgtttt tttgaaggat ggcacatact acaaattaag caaaaatgat    2340
acaaaggcgc tgctaaatat tattaaaaaa gaagcaaagg attgaaaatg aaaaagcgaa    2400
gctaaccgct tcgctttttc attttattgg ggcaaaatat ctctcagtgc ccgtctgagc    2460
attttccccg tcgcattttt cggaatatcg tcaagaaacg taatggcggc aggccgcttg    2520
tattttgcca gatgcttttc gcagtgctgc atgatgtcct cctctgttac cccagagcgt    2580
ttcggcacca catatc                                                    2596
```

```
<210> SEQ ID NO 30
<211> LENGTH: 4133
<212> TYPE: DNA
<213> ORGANISM: artificial sequence
<220> FEATURE:
<223> OTHER INFORMATION: synthesized sequence

<400> SEQUENCE: 30
gcaaaacgcg gatcattgga agagacgacc gtacccgcag catcaatgcc taaaataagc    60
ggatactctc tgacgatatt gcctcctgct tttccggcca gaccatcttt gtaattaatg    120
ccggaataag caactttaat caggacacca tccttcggca aatcctctgt tgatatggtt    180
ttcacatgga ctgaaacatc atcggcattt ttttctgcct gcaaggcttg aaataacgtt    240
gacattcggc acactccttt tcatttatat cgtaaccgaa gaacgttcaa aaaaccaaat    300
catcaagccg ccattttcac ttcgccggca cattgagaca ataatggaca aatccggtat    360
cctcttcata gccgttttgc tcatacaagc ttcttgcctt ccggttgtgg tgctcagtct    420
```

-continued

```
gaagtgttaa acattttgcc ccgttttgcc ctgcataatc ctttgcggca gaaagcagcc      480
ggccgccggc tccctttgta cgcgcatgag gaacgacaaa taagtcattt aatatgtata      540
tccttttcat tgacacagaa gaaaacgttg gatagagctg ggtaaagcct atgaattctc      600
cattttcttc tgctatcaaa ataacagact cgtgattttc caaacgagct ttcaaaaaag      660
cctctgcccc ttgcaaatcg gatgcctgtc tataaaattc ccgatattgg ttaaacagcg      720
gcgcaatggc ggccgcatct gatgtctttg cttggcgaat gttcatctta tttcttcctc      780
cctctcaata attttttcat tctatccctt ttctgtaaag tttatttttc agaatacttt      840
tatcatcatg ctttgaaaaa atatcacgat aaatatccatt gttctcacgg aagcacacgc      900
gctgataaac agctgacatc aactaaaagt ttcattaaat actttgaaaa aagttgttga      960
cttaaaagaa gctaaatgtt atagtaattg tacagaatag tcttttaagt aagtctactc     1020
tgaatttttt taaaaggaga gggtaaagag tgagaagcaa aaaattgtgg atcagcttgt     1080
tgtttgcgtt aacgttaatc tttacgatgg cgttcagcaa catgtctgcg caggctgctg     1140
aagaagcaaa agaaaaatat ttaattggct ttaatgagca ggaagctgtc agtgagtttg     1200
tagaacaagt agaggcaaat gacgaggtcg ccattctctc tgaggaagag gaagtcgaaa     1260
ttgaattgct tcatgaattt gaaacgattc ctgttttatc cgttgagtta agcccagaag     1320
atgtggacgc gcttgaactc gatccagcga tttcttatat tgaagaggat gcagaagtaa     1380
cgacaatgca acaaacagtg ccatggggaa ttactcgtgt gcaagcccca gctgttcata     1440
accgtggaat tacaggttct ggtgtaagag ttgctatcct cgattcaggt atttccacac     1500
atgaagactt aaatgttcgt ggtggcgtta gctttgtacc aggggaacca acgtatgctg     1560
atttaaatgg gcatggcacg catgtggctg ggacggtagc tgctttaaac aattcgattg     1620
gcgttgttgg cgtagcaccg tcagcggatc tatacgctgt taaagtatta ggggcgaatg     1680
gtagaggttc ggtcagcggg attgcccaag gattggaatg ggcagcacaa aataacatgc     1740
acattgctaa tatgagttta ggaacagatg caccaagttc tacacttgag cgtgctgtta     1800
attatgcgac ttctagagat gttcttgtta ttgcggcaac tgggaataac ggttctggct     1860
cagtaggcta tccggcccgt tatgcgaacg caatggcagt cggagctact gaccaaaaca     1920
acagacgcgc caacttttca cagtatggca cggggattga cattgtcgca ccaggtgtaa     1980
acgtgcagag cacatacccca ggtaaccgtt atgtgagcat gaacggtaca tcgatggcta     2040
ctcctcatgt tgcaggtgca gcagcccttg ttaaacaacg ctatccatct tggaatgcga     2100
ctcaaatccg cgaccatcta aagaatacgg caacgaattt aggaaactct tcacaatttg     2160
gaagcggact tgtcaatgca gaagcggcaa cacgctaatc tagatacata aaaaaccggc     2220
cttggccccg ccggtttttt attattttc ttcctccgca tgttcaatcc gctccataat     2280
cgacggatgg ctccctctga aaattttaac gagaaacggc gggttgaccc ggctcagtcc     2340
cgtaacggcc aagtcctgaa acgtctcaat cgccgcttcc cggtttccgg tcagctcaat     2400
gccgtaacgg tcggcggcgt tttcctgata ccggagacg gcattcgtaa tcaacgcctc     2460
actcctcaca tcaacccgtt acttctattg taatcataaa ttcaaattct tagaaccaag     2520
ctgtgttccg cactttttcca ccctttttaag catggaaacc ccgatcgctg ggaaaactaa     2580
caatgtttgg agtgatgcaa atgaaaaaaa tagtggcagc catcgtggta atcggtcttg     2640
tgtttatcgc attttttat ctttacagcc gatcaggcga tgtgtatcaa tcggtagacg     2700
cggatttgat cacactgtct tcaagcggcc aggaagatat cgagattgaa aaaagacagc     2760
acgtcaaaga tatgctggat attatgaatc agggaaaaca ggtgaagaca gaaaaaacat     2820
```

```
cagccctga ttacgaaggg acaatcaagt ttcataaaga ccggtatgac tcattcagac      2880
tatggattga cggcagccag caagccgttt ttttgaagga tggcacatac tacaaattaa      2940
gcaaaaatga tacaaaggcg ctgctaaata ttattaaaaa agaagcaaag gattgaaaat      3000
gaaaaagcga agctaaccgc ttcgcttttt cattttattg gggcaaaata tctctcagtg      3060
cccgtctgag cattttcccc gtcgcatttt tcggaatatc gtcaagaaac gtaatggcgg      3120
caggccgctt gtattttgcc agatgctttt cgcagtgctg catgatgtcc tcctctgtta      3180
ccccagagcg tttcggcacc acatatccct ttaccgcttc cccgctttgg gggtccggca      3240
cgccgatgac aaccgcctcc ttgacgtccg gatggctgta cagcacctcc tccacctccc      3300
gcggatacac attgtatcct cctacaatga tcatgtcttt tttccggtca acaatgtaaa      3360
aatagccgtc ctcatcccgt cttgccaagt ccccgtata aagccacccg tctttaatg      3420 catgctctgt ttccatcggc attttataat agcccttcat cacattgggg cctttcacga      3480
tcaattcgcc gacctggtga gcgggcagct cgcgtccgag cggatctacg accttgtttt      3540
cgacatgtaa gatacttgtc ccgatggagc ccggctttct gcccctgtca aacgggttaa      3600
agcacgtgac gggtgatgct tccgagagcc cgtagccttc caaaatggta acaccgaatt      3660
tttcttcaaa cgccgtcagc aacgcgactg gcatggacgc gcctcccgaa atgcacagcc      3720
ggatcgaaga aaaatcatct ttctttccgt tttcatgctg aaacaagtag ttatacattg      3780
taggcacacc ggcaaaaatg gtcgcctgct gctgcttaac aagcttaaaa acagatgccg      3840
gactgaattg aggctcaatc aatacagttg cgccgctcat cagcggtgca ttcatacaga      3900
cggttaaaca aaacacgtga aacatgggaa gagcgcagac cacattgtcc ctctcatcca      3960
ttcccaaata gcctgcgaca tcgttggcat tgctgtacaa attctgatgt gtcagcatcg      4020
cgcctttcgg ttttccagtc gttcctgacg tatataaaat aaccgcggta tcatcaggta      4080
caggttcttg gttttgttta gcggcagatg tcggccgcaa tattttttgca aac            4133
```

<210> SEQ ID NO 31
<211> LENGTH: 5423
<212> TYPE: DNA
<213> ORGANISM: artificial sequence
<220> FEATURE:
<223> OTHER INFORMATION: synthesized sequence

<400> SEQUENCE: 31

```
gcaaaacgcg gatcattgga agagacgacc gtacccgcag catcaatgcc taaaataagc        60
ggatactctc tgacgatatt gcctcctgct tttccggcca gaccatcttt gtaattaatg       120
ccggaataag caactttaat caggacacca tccttcggca aatcctctgt tgatatggtt       180
ttcacatgga ctgaaacatc atcggcattt ttttctgcct gcaaggcttg aaataacgtt       240
gacattcggc acactccttt tcatttatat cgtaaccgaa gaacgttcaa aaaaccaaat       300
catcaagccg ccattttcac ttcgccggca cattgagaca ataatggaca aatccggtat       360
cctcttcata gccgttttgc tcatacaagc ttcttgcctt ccggttgtgg tgctcagtct       420
gaagtgttaa acattttgcc ccgtttttgcc ctgcataatc ctttgcggca gaaagcagcc       480
ggccgccggc tccctttgta cgcgcatgag gaacgacaaa taagtcattt aatatgtata       540
tccttttcat tgacacagaa gaaaacgttg gatagagctg ggtaaagcct atgaattctc       600
cattttcttc tgctatcaaa ataacagact cgtgattttc caaacgagct ttcaaaaaag       660
cctctgcccc ttgcaaatcg gatgcctgtc tataaaattc ccgatattgg ttaaacagcg       720
```

-continued

```
gcgcaatggc ggccgcatct gatgtctttg cttggcgaat gttcatctta tttcttcctc      780
cctctcaata attttttcat tctatccctt ttctgtaaag tttatttttc agaatacttt      840
tatcatcatg ctttgaaaaa atatcacgat aatatccatt gttctcacgg aagcacacgc      900
gctgataaac agctgacatc aactaaaagt ttcattaaat actttgaaaa aagttgttga      960
cttaaaagaa gctaaatgtt atagtaattg tacagaatag tcttttaagt aagtctactc     1020
tgaatttttt taaaaggaga gggtaaagag tgagaagcaa aaaattgtgg atcagcttgt     1080
tgtttgcgtt aacgttaatc tttacgatgg cgttcagcaa catgtctgcg caggctgctg     1140
aagaagcaaa agaaaaatat ttaattggct ttaatgagca ggaagctgtc agtgagtttg     1200
tagaacaagt agaggcaaat gacgaggtcg ccattctctc tgaggaagag gaagtcgaaa     1260
ttgaattgct tcatgaattt gaaacgattc ctgtttatc cgttgagtta agcccagaag      1320
atgtggacgc gcttgaactc gatccagcga tttcttatat tgaagaggat gcagaagtaa     1380
cgacaatgca acaaacagtg ccatggggaa ttactcgtgt gcaagcccca gctgttcata     1440
accgtggaat tacaggttct ggtgtaagag ttgctatcct cgattcaggt atttccacac     1500
atgaagactt aaatgttcgt ggtggcgtta gctttgtacc aggggaacca acgtatgctg     1560
atttaaatgg gcatggcacg catgtggctg ggacggtagc tgctttaaac aattcgattg     1620
gcgttgttgg cgtagcaccg tcagcggatc tatacgctgt aaagtatta ggggcgaatg      1680 gtagaggttc ggtcagcggg attgcccaag gattggaatg ggcagcacaa aataacatgc     1740
acattgctaa tatgagttta ggaacagatg caccaagttc tacacttgag cgtgctgtta     1800
attatgcgac ttctagagat gttcttgtta ttgcggcaac tgggaataac ggttctggct     1860
cagtaggcta tccggcccgt tatgcgaacg caatggcagt cggagctact gaccaaaaca     1920
acagacgcgc caacttttca cagtatggca cggggattga cattgtcgca ccaggtgtaa     1980
acgtgcagag cacataccca ggtaaccgtt atgtgagcat gaacggtaca tcgatggcta     2040
ctcctcatgt tgcaggtgca gcagcccttg ttaaacaacg ctatccatct tggaatgcga     2100
ctcaaatccg cgaccatcta aagaatacgg caacgaattt aggaaactct tcacaatttg     2160
gaagcggact tgtcaatgca gaagcggcaa cacgctaatc tagatacata aaaaaccggc     2220
cttggccccg ccggtttttt attattttc ttcctccgca tgttcaatcc gctccataat      2280
cgacggatgg ctccctctga aaattttaac gagaaacggc gggttgaccc ggctcagtcc     2340
cgtaacggcc aagtcctgaa acgtctcaat cgccgcttcc cggtttccgg tcagctcaat     2400
gccgtaacgg tcggcggcgt tttcctgata ccgggagacg gcattcgtaa tcaacgcctc     2460
actcctcaca tcaacccgtt acttctattg taatcataaa ttcaaattct tagaaccaag     2520
ctgtgttccg cacttttcca ccctttaag catggaaacc ccgatcgctg ggaaaactaa      2580
caatgtttgg agtgatgcaa atgaaaaaaa tagtggcagc catcgtggta atcggtcttg     2640
tgtttatcgc atttttttat ctttacagcc gatcaggcga tgtgtatcaa tcggtagacg     2700
cggatttgat cacactgtct tcaagcggcc aggaagatat cgagattgaa aaaagacagc     2760
acgtcaaaga tatgctggat attatgaatc agggaaaaca ggtgaagaca gaaaaaacat     2820 cagccctga ttacgaaggg acaatcaagt ttcataaaga ccggtatgac tcattcagac      2880
tatggattga cggcagccag caagccgttt ttttgaagga tggcacatac tacaaattaa     2940
gcaaaaatga tacaaaggcg ctgctaaata ttattaaaaa agaagcaaag gattgaaaat     3000
gaaaaagcga agctaaccgc ttcgcttttt cattttattg gggcaaaata tctctcagtg     3060
cccgtctgag cattttcccc gtcgcatttt tcggaatatc gtcaagaaac gtaatggcgg     3120
```

-continued

```
caggccgctt gtattttgcc agatgctttt cgcagtgctg catgatgtcc tcctctgtta      3180
ccccagagcg tttcggcacc acatatccct ttaccgcttc cccgctttgg gggtccggca      3240
cgccgatgac aaccgcctcc ttgacgtccg gatggctgta cagcacctcc tccacctccc      3300
gcggatacac attgtatcct cctacaatga tcatgtcttt tttccggtca acaatgtaaa      3360
aatagccgtc ctcatcccgt cttgccaagt cccccgtata aagccacccg tcttttaatg      3420
catgctctgt ttccatcggc attttataat agcccttcat cacattgggg cctttcacga      3480
tcaattcgcc gacctggtga gcgggcagct cgcgtccgag cggatctacg accttgtttt      3540
cgacatgtaa gatacttgtc ccgatggagc ccggctttct gcccctgtca aacgggttaa      3600
agcacgtgac gggtgatgct tccgagagcc cgtagccttc caaaatggta acaccgaatt      3660
tttcttcaaa cgccgtcagc aacgcgactg gcatggacgc gcctcccgaa atgcacagcc      3720
ggatcgaaga aaaatcatct ttctttccgt tttcatgctg aaacaagtag ttatacattg      3780
taggcacacc ggcaaaaatg gtcgcctgct gctgcttaac aagcttaaaa acagatgccg      3840
gactgaattg aggctcaatc aatacagttg cgccgctcat cagcggtgca ttcatacaga      3900
cggttaaaca aaacacgtga aacatgggaa gagcgcagac cacattgtcc ctctcatcca      3960
ttcccaaata gcctgcgaca tcgttggcat tgctgtacaa attctgatgt gtcagcatcg      4020
cgcctttcgg ttttccagtc gttcctgacg tatataaaat aaccgcggta tcatcaggta      4080
caggttcttg gttttgttta gcggcagatg tcggccgcaa tattttttgca aacgttgtca      4140 ttttcatcct gacctctggg tccgcagctt ccggctcggc ctccccgtc tggcataaaa      4200 tgacgagctc aacctttggc agcgattcat gcatgctctc ataaagcggc aaaagctggc      4260
taacgcccac gattgccttt acatcgccat ttgtcagcat ataaccaatt tctgtcggcg      4320
tgtacaacgg attgatggga acaactacga tcccagcttt taaagcgcca aaaacgcga      4380 tgataaaatc aggcgaattg ccaagcagca aagctaaatg gtcccctttc tccataccgg      4440
cttcctgaag gccgtccgca aatcgctgaa tatattcatt cagctcttga tacgtcatca      4500
tgtgatcttt aaacctgcat gcgatgctgt cgggcttctc agatgctgtt tcttccaatt      4560
ttgaaacaag attcattctc ccacccctta agtgaatgaa tagtcattca ttattgaagc      4620
caagctttct tctccattat agagaaacag aaaaaaacac tcaagagcaa aaagccctga      4680
gtgtcagtac tgtcatagtt tcttcaatgc ttcggcaatc ggcgtatctc cttctgtcag      4740
atcaaaggcc cgattttccg tattcttctc atctaaagag gcaatgaccg tttttgcaac      4800
gtcatcacgg gaaataaatc cccgctccag atccttcgct gctgaaacag ttcccgttcc      4860
aggctcattg cgaaggcctc ccggacggat aatcgtatag gttaaaccgc tcgcttccag      4920
aattttatca gcataatgct tggccacata ataaggcttg agtgcctcat tccaattttc      4980
acggttatgg gcttgcaggg cgctgaccat aataaaccgt ttgattccgg caatggccgc      5040
agcttcaatg gcttttgccg ctccatcaag atccaccagc agcgtttat catagcctgt      5100 gctgccgccg gaaccggctg tgaaaatgat cgcgtcacaa ccttttgccg cagcggcgat      5160
ttcttccggg ctgccctcca gattcgcaag cacagcttct gcaccggcag cttcaagaga      5220
cgctttctgt tcttcttttc tgaccatcgc tctgatggaa tgatcaggat tatcttggaa      5280
taaagagacg agtctttgcc cgatttgtcc gttcgctccg attaaaaaca ctttcatgtg      5340
aatccctcct gcctccatta tttcaaaaac acaaccgctc tttcaaacga tgtgttttgc      5400
cttagtaaat cagatcaagg aaa                                              5423
```

<210> SEQ ID NO 32
<211> LENGTH: 6198
<212> TYPE: DNA
<213> ORGANISM: artificial sequence
<220> FEATURE:
<223> OTHER INFORMATION: synthesized sequence

<400> SEQUENCE: 32

```
tcgtcaacgc ctgcctcagc aacattgaat ttgcagaaga aaaatggcgg ataaaagact       60
ataatatcaa cagccactta tccggcttta tcaaataaga aaaagacagg cgtttgcctg      120
tcttttcttt tatttcttag cagccggcat ctctttttga agctcgtcca aaatggcatt      180
cgccccgtct acactgcggc gcagagacca caccgcacga tccacgtggt atacatgccc      240 gttttttcact gccttcagtt ttttccaaag acattctttt tcgatcgggc gtttaccgtc      300
ggcgtcgagg tcatctgttt ttcctgtcat caggatgatc acatccggat ctgttttcag      360
cagctgctcc agtgtcattt tcatattcac agagtcgccg ccattgcttg aatcgctatt      420
gcctgacgta ctgattgcat atcggtagcc gacctgtgtt aaaagtctcg atgtaaagaa      480
gttttcatcc ctggccataa tggtatcatt tgtatttccg atcaaaagca cggactggct      540
gttcgcgctg attttctgct ttgtctcgct aagcttttct tcatgcgccg tcagcttttt      600
ctccatttcc ttctccttgc cgactgcttt tgcaatcgta agcgaagcgt caattgtatc      660
ctgataatca gcatttaaat tattaagtgc aatcgtcggc gctatttttt tcagctgatc      720
gtacaccttc ttatgccggg tcgtgtcagc aataattaaa tcgggtttta atgaagcgat      780
tttttccatg cttggctgtg agcgagtgcc gacagatgtg tagccgtcaa ttttcttcag      840
cacatccttg ttgatcagct gcttcgcttt gttgtcatcg gcaaccccga caggcgtaat      900
gccgagatca agcagtgtat caataaaacc tagctcaaga acaacaaccc gcttcggatg      960
ctcaggcaca tttgtcttcc ctaaatcatg tgttaccgcc actttatgtt ctttactgtt     1020
ttgattgccg cttgaagacg agcaagcagc cgttaagaca gaaagaagta aaactgtaag     1080
aataatcagt gttttttttca tatgttccag tctctcctgt tggtagtttc tatggttaag     1140
atgtccaaga gtagtataac acggaatgag aatcattatc accaattatt tttaaaatga     1200
gaagagaaag ttcggcttac aggaaaatct tgtttcgcga cacagcagtt cagcagctga     1260
tcatcctgtc cacaaaaaag cttgcagaaa aataacattc tctgcaagct gatcctgtta     1320
aagcttcaca atcactcttc cttgaatgcg attttgcaaa atatctttta acgcacccgg     1380 cgttcttcc aatgatactt ccctgtccac gatggtcagc agctgatcag gcttgagatc     1440
agaagacatg cgctcccaaa cagcggctct gacgtccatc ggacaatata ctgaatcgat     1500
tccgagcagg cttactccgc gaagaataaa aggatacacg gttgccggaa cttctcctcc     1560
gccggttaag ccgctcactg cgacagatcc gccgtattga attttgctta aaagcgaggc     1620
aagctgtttt ccgccgactg gatcaaccgc tccctgccat tgctgcttgg acagcgcctt     1680
aagcgttccg tcatagacat cttccctgct gattacttcg cttgcaccaa gctgtttcaa     1740
ataatcagcc gcctcccggt ttccggtact tgccaccaca tcataacccc gcttgttcag     1800
catcgatacc gcaattccgc cgacaccgcc ggttgctcct gtgactagca cgctgccttt     1860
ttccggagac agaccgttct gttcaagccg atgcactgat aacgccgcag taaatcccgc     1920
cgttccgtac accatcgctt cttttaacga aagattctgt ggcaaaggca ccagccagtc     1980
accaggcacc gaagcgtatt cacttaatcc gccatcacgt gagacaccga gctcatagct     2040
tgtcgcgatc acctcatccc cctccgcaaa acgcggatca ttggaagaga cgaccgtacc     2100
```

-continued

```
cgcagcatca atgcctaaaa taagcggata ctctctgacg atattgcctc ctgctttttcc    2160 ggccagacca tctttgtaat taatgccgga ataagcaact ttaatcagga caccatcctt    2220
cggcaaatcc tctgttgata tggttttcac atggactgaa acatcatcgg cattttttc      2280 tgcctgcaag gcttgaaata acgttgacat tcggcacact cctttcatt tatatcgtaa      2340 ccgaagaacg ttcaaaaaac caaatcatca agccgccatt ttcacttcgc cggcacattg     2400
agacaataat ggacaaatcc ggtatcctct tcatagccgt tttgctcata caagcttctt     2460
gccttccggt tgtggtgctc agtctgaagt gttaaacatt ttgccccgtt ttgccctgca     2520
taatcctttg cggcagaaag cagccggccg ccggctccct ttgtacgcgc atgaggaacg     2580
acaaataagt catttaatat gtatatcctt ttcattgaca cagaagaaaa cgttggatag     2640
agctgggtaa agcctatgaa ttctccattt tcttctgcta tcaaaataac agactcgtga     2700
ttttccaaac gagctttcaa aaaagcctct gccccttgca aatcggatgc ctgtctataa     2760
aattcccgat attggttaaa cagcggcgca atggcggccg catctgatgt ctttgcttgg     2820
cgaatgttca tcttatttct tcctccctct caataatttt ttcattctat ccctttttctg   2880 taaagtttat ttttcagaat acttttatca tcatgctttg aaaaaatatc acgataaatat    2940 ccattgttct cacggaagca cacgcgctga taaacagctg acatcaacta aaagtttcat     3000
taaatacttt gaaaaaagtt gttgacttaa aagaagctaa atgttatagt aattgtacag     3060
aatagtcttt taagtaagtc tactctgaat tttttaaaa ggagagggta aagagtgaga      3120
agcaaaaaat tgtggatcag cttgttgttt gcgttaacgt taatctttac gatggcgttc     3180
agcaacatgt ctgcgcaggc tgctgaagaa gcaaaagaaa aatatttaat tggctttaat     3240
gagcaggaag ctgtcagtga gtttgtagaa caagtagagg caaatgacga ggtcgccatt     3300
ctctctgagg aagaggaagt cgaaattgaa ttgcttcatg aatttgaaac gattcctgtt     3360
ttatccgttg agttaagccc agaagatgtg gacgcgcttg aactcgatcc agcgatttct     3420
tatattgaag aggatgcaga agtaacgaca atgcaacaaa cagtgccatg gggaattact     3480
cgtgtgcaag ccccagctgt tcataaccgt ggaattacag gttctggtgt aagagttgct     3540
atcctcgatt caggtatttc cacacatgaa gacttaaatg ttcgtggtgg cgttagcttt     3600
gtaccagggg aaccaacgta tgctgattta aatgggcatg gcacgcatgt ggctgggacg     3660
gtagctgctt aaacaattc gattggcgtt gttggcgtag caccgtcagc ggatctatac      3720
gctgttaaag tattaggggc gaatggtaga ggttcggtca gcgggattgc ccaaggattg     3780
gaatgggcag cacaaaataa catgcacatt gctaatatga gtttaggaac agatgcacca     3840
agttctacac ttgagcgtgc tgttaattat gcgacttcta gagatgttct tgttattgcg     3900
gcaactggga ataacggttc tggctcagta ggctatccgg cccgttatgc gaacgcaatg     3960
gcagtcggag ctactgacca aaacaacaga cgcgccaact tttcacagta tggcacgggg     4020
attgacattg tcgcaccagg tgtaaacgtg cagagcacat acccaggtaa ccgttatgtg     4080
agcatgaacg gtacatcgat ggctactcct catgttgcag gtgcagcagc ccttgttaaa    4140
caacgctatc catcttggaa tgcgactcaa atccgcgacc atctaaagaa tacggcaacg     4200
aatttaggaa actcttcaca atttggaagc ggacttgtca atgcagaagc ggcaacacgc     4260
taatctagat acataaaaaa ccggccttgg ccccgccggt ttttttattat ttttcttcct    4320 ccgcatgttc aatccgctcc ataatcgacg gatggctccc tctgaaaatt ttaacgagaa     4380
acggcgggtt gacccggctc agtcccgtaa cggccaagtc ctgaaacgtc tcaatcgccg     4440
```

```
cttcccggtt tccggtcagc tcaatgccgt aacggtcggc ggcgttttcc tgataccggg    4500
agacggcatt cgtaatcaac gcctcactcc tcacatcaac ccgttacttc tattgtaatc    4560
ataaattcaa attcttagaa ccaagctgtg ttccgcactt ttccaccctt ttaagcatgg    4620
aaaccccgat cgctgggaaa actaacaatg tttggagtga tgcaaatgaa aaaaatagtg    4680
gcagccatcg tggtaatcgg tcttgtgttt atcgcatttt tttatcttta cagccgatca    4740
ggcgatgtgt atcaatcggt agacgcggat ttgatcacac tgtcttcaag cggccaggaa    4800
gatatcgaga ttgaaaaaag acagcacgtc aaagatatgc tggatattat gaatcaggga    4860
aaacaggtga agacagaaaa aacatcagcc cctgattacg aagggacaat caagtttcat    4920
aaagaccggt atgactcatt cagactatgg attgacggca gccagcaagc cgtttttttg    4980
aaggatggca catactacaa attaagcaaa aatgatacaa aggcgctgct aaatattatt    5040
aaaaaagaag caaaggattg aaaatgaaaa agcgaagcta accgcttcgc ttttttcattt    5100 tattggggca aaatatctct cagtgcccgt ctgagcattt tccccgtcgc atttttcgga    5160
atatcgtcaa gaaacgtaat ggcggcaggc cgcttgtatt ttgccagatg cttttcgcag    5220
tgctgcatga tgtcctcctc tgttacccca gagcgtttcg gcaccacata tccctttacc    5280
gcttccccgc tttggggggtc cggcacgccg atgacaaccg cctccttgac gtccggatgg    5340
ctgtacagca cctcctccac ctcccgcgga tacacattgt atcctcctac aatgatcatg    5400
tcttttttcc ggtcaacaat gtaaaaatag ccgtcctcat cccgtcttgc caagtccccc    5460
gtataaagcc accgtctttt taatgcatgc tctgtttcca tcggcatttt ataatagccc    5520
ttcatcacat tggggccttt cacgatcaat tcgccgacct ggtgagcggg cagctcgcgt    5580
ccgagcggat ctacgacctt gttttcgaca tgtaagatac ttgtcccgat ggagcccggc    5640
tttctgcccc tgtcaaacgg gttaaagcac gtgacgggtg atgcttccga gagcccgtag    5700
ccttccaaaa tggtaacacc gaattttttct tcaaacgccg tcagcaacgc gactggcatg    5760
gacgcgcctc ccgaaatgca cagccggatc gaagaaaaat catctttctt tccgtttttca    5820 tgctgaaaca agtagttata cattgtaggc acaccggcaa aaatggtcgc ctgctgctgc    5880
ttaacaagct taaaaacaga tgccggactg aattgaggct caatcaatac agttgcgccg    5940
ctcatcagcg gtgcattcat acagacggtt aaacaaaaca cgtgaaacat gggaagagcg    6000
cagaccacat tgtccctctc atccattccc aaatagcctg cgacatcgtt ggcattgctg    6060
tacaaattct gatgtgtcag catcgcgcct ttcggttttc cagtcgttcc tgacgtatat    6120
aaaataaccg cggtatcatc aggtacaggt tcttggtttt gtttagcggc agatgtcggc    6180
cgcaatattt ttgcaaac                                                  6198
```

<210> SEQ ID NO 33
<211> LENGTH: 7488
<212> TYPE: DNA
<213> ORGANISM: artificial sequence
<220> FEATURE:
<223> OTHER INFORMATION: synthesized sequence

<400> SEQUENCE: 33

```
tcgtcaacgc ctgcctcagc aacattgaat ttgcagaaga aaaatggcgg ataaaagact      60
ataatatcaa cagccactta tccggctttta tcaaataaga aaaagacagg cgtttgcctg     120
tcttttcttt tatttcttag cagccggcat ctctttttga agctcgtcca aaatggcatt     180
cgccccgtct acactgcggc gcagagacca caccgcacga tccacgtggt atacatgccc     240 gttttttcact gccttcagtt ttttccaaag gacattcttt tcgatcgggc gtttaccgtc     300
```

-continued

```
ggcgtcgagg tcatctgttt ttcctgtcat caggatgatc acatccggat ctgttttcag    360
cagctgctcc agtgtcattt tcatattcac agagtcgccg ccattgcttg aatcgctatt    420
gcctgacgta ctgattgcat atcggtagcc gacctgtgtt aaaagtctcg atgtaaagaa    480
gttttcatcc ctggccataa tggtatcatt tgtatttccg atcaaaagca cggactggct    540
gttcgcgctg attttctgct ttgtctcgct aagcttttct tcatgcgccg tcagcttttt    600
ctccatttcc ttctccttgc cgactgcttt tgcaatcgta agcgaagcgt caattgtatc    660
ctgataatca gcatttaaat tattaagtgc aatcgtcggc gctattttt tcagctgatc    720 gtacaccttc ttatgccggg tcgtgtcagc aataattaaa tcgggtttta atgaagcgat    780 ttttccatg cttggctgtg agcgagtgcc gacagatgtg tagccgtcaa ttttcttcag    840
cacatccttg ttgatcagct gcttcgcttt gttgtcatcg gcaacccga caggcgtaat    900 gccgagatca agcagtgtat caataaaacc tagctcaaga acaacaaccc gcttcggatg    960
ctcaggcaca tttgtcttcc ctaaatcatg tgttaccgcc actttatgtt ctttactgtt   1020
ttgattgccg cttgaagacg agcaagcagc cgttaagaca gaaagaagta aaactgtaag   1080
aataatcagt gttttttttca tatgttccag tctctcctgt tggtagtttc tatggttaag   1140
atgtccaaga gtagtataac acggaatgag aatcattatc accaattatt tttaaaatga   1200
gaagagaaag ttcggcttac aggaaaatct tgtttcgcga cacagcagtt cagcagctga   1260
tcatcctgtc cacaaaaaag cttgcagaaa aataacattc tctgcaagct gatcctgtta   1320
aagcttcaca atcactcttc cttgaatgcg attttgcaaa atatctttta acgcacccgg   1380
cgtttcttcc aatgatactt ccctgtccac gatggtcagc agctgatcag gcttgagatc   1440
agaagacatg cgctcccaaa cagcggctct gacgtccatc ggacaatata ctgaatcgat   1500
tccgagcagg cttactccgc gaagaataaa aggatacacg gttgccggaa cttctcctcc   1560
gccggttaag ccgctcactg cgacagatcc gccgtattga attttgctta aaagcgaggc   1620
aagctgtttt ccgccgactg gatcaaccgc tccctgccat tgctgcttgg acagcgcctt   1680
aagcgttccg tcatagacat cttccctgct gattacttcg cttgcaccaa gctgtttcaa   1740
ataatcagcc gcctcccggt ttccggtact tgccaccaca tcataacccc gcttgttcag   1800
catcgatacc gcaattccgc cgacaccgcc ggttgctcct gtgactagca cgctgccttt   1860
ttccggagac agaccgttct gttcaagccg atgcactgat aacgccgcag taaatcccgc   1920
cgttccgtac accatcgctt cttttaacga aagattctgt ggcaaaggca ccagccagtc   1980
accaggcacc gaagcgtatt cacttaatcc gccatcacgt gagacaccga gctcatagct   2040
tgtcgcgatc acctcatccc cctccgcaaa acgcggatca ttggaagaga cgaccgtacc   2100
cgcagcatca atgcctaaaa taagcggata ctctctgacg atattgcctc ctgctttttcc   2160 ggccagacca tctttgtaat taatgccgga ataagcaact ttaatcagga caccatcctt   2220
cggcaaatcc tctgttgata tggttttcac atggactgaa acatcatcgg catttttttc   2280
tgcctgcaag gcttgaaata acgttgacat tcggcacact cctttcatt tatatcgtaa   2340 ccgaagaacg ttcaaaaaac caaatcatca agccgccatt ttcacttcgc cggcacattg   2400
agacaataat ggacaaatcc ggtatcctct tcatagccgt tttgctcata caagcttctt   2460
gccttccggt tgtggtgctc agtctgaagt gttaaacatt ttgccccgtt ttgccctgca   2520
taatcctttg cggcagaaag cagccggccg ccggctccct ttgtacgcgc atgaggaacg   2580
acaaataagt catttaatat gtatatcctt ttcattgaca cagaagaaaa cgttggatag   2640
```

-continued

```
agctgggtaa agcctatgaa ttctccattt tcttctgcta tcaaaataac agactcgtga    2700
ttttccaaac gagctttcaa aaaagcctct gccccttgca aatcggatgc ctgtctataa    2760
aattcccgat attggttaaa cagcggcgca atggcggccg catctgatgt ctttgcttgg    2820
cgaatgttca tcttatttct tcctccctct caataatttt ttcattctat ccctttctg     2880 taaagtttat ttttcagaat acttttatca tcatgctttg aaaaaatatc acgataatat    2940
ccattgttct cacggaagca cacgcgctga taaacagctg acatcaacta aaagtttcat    3000
taaatacttt gaaaaaagtt gttgacttaa aagaagctaa atgttatagt aattgtacag    3060
aatagtcttt taagtaagtc tactctgaat tttttaaaa ggagagggta aagagtgaga     3120
agcaaaaaat tgtggatcag cttgttgttt gcgttaacgt taatctttac gatggcgttc    3180
agcaacatgt ctgcgcaggc tgctgaagaa gcaaaagaaa aatatttaat tggctttaat    3240
gagcaggaag ctgtcagtga gtttgtagaa caagtagagg caaatgacga ggtcgccatt    3300
ctctctgagg aagaggaagt cgaaattgaa ttgcttcatg aatttgaaac gattcctgtt    3360
ttatccgttg agttaagccc agaagatgtg gacgcgcttg aactcgatcc agcgatttct    3420
tatattgaag aggatgcaga agtaacgaca atgcaacaaa cagtgccatg gggaattact    3480
cgtgtgcaag ccccagctgt tcataaccgt ggaattacag gttctggtgt aagagttgct    3540
atcctcgatt caggtatttc cacacatgaa gacttaaatg ttcgtggtgg cgttagcttt    3600
gtaccagggg aaccaacgta tgctgattta aatgggcatg gcacgcatgt ggctgggacg    3660
gtagctgctt taaacaattc gattggcgtt gttggcgtag caccgtcagc ggatctatac    3720
gctgttaaag tattaggggc gaatggtaga ggttcggtca gcgggattgc ccaaggattg    3780
gaatgggcag cacaaaataa catgcacatt gctaatatga gtttaggaac agatgcacca    3840 agttctcac ttgagcgtgc tgttaattat gcgacttcta gagatgttct tgttattgcg     3900
gcaactggga ataacggttc tggctcagta ggctatccgg cccgttatgc gaacgcaatg    3960
gcagtcggag ctactgacca aaacaacaga cgcgccaact tttcacagta tggcacgggg    4020
attgacattg tcgcaccagg tgtaaacgtg cagagcacat acccaggtaa ccgttatgtg    4080
agcatgaacg gtacatcgat ggctactcct catgttgcag gtgcagcagc ccttgttaaa    4140
caacgctatc catcttggaa tgcgactcaa atccgcgacc atctaaagaa tacggcaacg    4200
aatttaggaa actcttcaca atttggaagc ggacttgtca atgcagaagc ggcaacacgc    4260
taatctagat acataaaaaa ccggccttgg ccccgccggt tttttattat ttttcttcct    4320
ccgcatgttc aatccgctcc ataatcgacg gatggctccc tctgaaaatt ttaacgagaa    4380
acggcgggtt gacccggctc agtcccgtaa cggccaagtc ctgaaacgtc tcaatcgccg    4440
cttcccggtt tccggtcagc tcaatgccgt aacggtcggc ggcgtttcc tgataccggg     4500 agacggcatt cgtaatcaac gcctcactcc tcacatcaac ccgttacttc tattgtaatc    4560
ataaattcaa attcttagaa ccaagctgtg ttccgcactt ttccaccctt ttaagcatgg    4620
aaaccccgat cgctgggaaa actaacaatg tttggagtga tgcaaatgaa aaaaatagtg    4680
gcagccatcg tggtaatcgg tcttgtgttt atcgcatttt tttatcttta cagccgatca    4740
ggcgatgtgt atcaatcggt agacgcggat ttgatcacac tgtcttcaag cggccaggaa    4800
gatatcgaga ttgaaaaaag acagcacgtc aaagatatgc tggatattat gaatcaggga    4860
aaacaggtga agacagaaaa aacatcagcc cctgattacg aagggacaat caagtttcat    4920
aaagaccggt atgactcatt cagactatgg attgacggca gccagcaagc cgtttttttg    4980
aaggatggca catactacaa attaagcaaa aatgatacaa aggcgctgct aaatattatt    5040
```

-continued

```
aaaaaagaag caaaggattg aaaatgaaaa agcgaagcta accgcttcgc tttttcattt    5100
tattggggca aaatatctct cagtgcccgt ctgagcattt tccccgtcgc atttttcgga    5160
atatcgtcaa gaaacgtaat ggcggcaggc cgcttgtatt ttgccagatg cttttcgcag    5220
tgctgcatga tgtcctcctc tgttacccca gagcgtttcg gcaccacata tccctttacc    5280
gcttccccgc tttgggggtc cggcacgccg atgacaaccg cctccttgac gtccggatgg    5340
ctgtacagca cctcctccac ctcccgcgga tacacattgt atcctcctac aatgatcatg    5400 tctttttttcc ggtcaacaat gtaaaaatag ccgtcctcat cccgtcttgc caagtccccc    5460
gtataaagcc acccgtcttt taatgcatgc tctgtttcca tcggcatttt ataatagccc    5520
ttcatcacat tggggccttt cacgatcaat tcgccgacct ggtgagcggg cagctcgcgt    5580
ccgagcggat ctacgacctt gttttcgaca tgtaagatac ttgtcccgat ggagcccggc    5640
tttctgcccc tgtcaaacgg gttaaagcac gtgacgggtg atgcttccga gagcccgtag    5700
ccttccaaaa tggtaacacc gaattttttct tcaaacgccg tcagcaacgc gactggcatg    5760
gacgcgcctc ccgaaatgca cagccggatc gaagaaaaat catctttctt tccgtttttca    5820 tgctgaaaca agtagttata cattgtaggc acaccggcaa aaatggtcgc ctgctgctgc    5880
ttaacaagct taaaaacaga tgccggactg aattgaggct caatcaatac agttgcgccg    5940
ctcatcagcg gtgcattcat acagacggtt aaacaaaaca cgtgaaacat gggaagagcg    6000
cagaccacat tgtccctctc atccattccc aaatagcctg cgacatcgtt ggcattgctg    6060
tacaaattct gatgtgtcag catcgcgcct ttcggttttc cagtcgttcc tgacgtatat    6120
aaaataaccg cggtatcatc aggtacaggt tcttggtttt gtttagcggc agatgtcggc    6180
cgcaatattt ttgcaaacgt tgtcattttc atcctgacct ctgggtccgc agcttccggc    6240
tcggcctccc ccgtctggca taaaatgacg agctcaacct ttggcagcga ttcatgcatg    6300
ctctcataaa gcggcaaaag ctggctaacg cccacgattg cctttacatc gccatttgtc    6360
agcatataac caatttctgt cggcgtgtac aacggattga tgggaacaac tacgatccca    6420
gcttttaaag cgccaaaaaa cgcgatgata aaatcaggcg aattgccaag cagcaaagct    6480
aaatggtccc ctttctccat accggcttcc tgaaggccgt ccgcaaatcg ctgaatatat    6540
tcattcagct cttgatacgt catcatgtga tctttaaacc tgcatgcgat gctgtcgggc    6600
ttctcagatg ctgtttcttc caattttgaa acaagattca ttctcccacc ccttaagtga    6660
atgaatagtc attcattatt gaagccaagc tttcttctcc attatagaga aacagaaaaa    6720
aacactcaag agcaaaaagc cctgagtgtc agtactgtca tagtttcttc aatgcttcgg    6780
caatcggcgt atctccttct gtcagatcaa aggcccgatt ttccgtattc ttctcatcta    6840
aagaggcaat gaccgttttt gcaacgtcat cacgggaaat aaatccccgc tccagatcct    6900
tcgctgctga aacagttccc gttccaggct cattgcgaag gcctcccgga cggataatcg    6960
tataggttaa accgctcgct tccagaattt tatcagcata atgcttggcc acataataag    7020
gcttgagtgc ctcattccaa ttttcacggt tatgggcttg cagggcgctg accataataa    7080
accgtttgat tccggcaatg gccgcagctt caatggcttt tgccgctcca tcaagatcca    7140
ccagcagcgt tttatcatag cctgtgctgc cgccggaacc ggctgtgaaa atgatcgcgt    7200
cacaaccttt tgccgcagcg gcgatttctt ccgggctgcc ctccagattc gcaagcacag    7260
cttctgcacc ggcagcttca agagacgctt tctgttcttc ttttctgacc atcgctctga    7320
tggaatgatc aggattatct tggaataaag agacgagtct ttgcccgatt tgtccgttcg    7380
```

-continued

```
ctccgattaa aaacactttc atgtgaatcc ctcctgcctc cattatttca aaaacacaac      7440
cgctctttca aacgatgtgt tttgccttag taaatcagat caaggaaa                    7488

<210> SEQ ID NO 34
<211> LENGTH: 6017
<212> TYPE: DNA
<213> ORGANISM: artificial sequence
<220> FEATURE:
<223> OTHER INFORMATION: synthesized sequence

<400> SEQUENCE: 34
gatcaaaaga gggtatgtta tctatcaaac aaactcgttc agagttagtc gaatcaggta        60
tagaaggcct taaggatatt atcttaaaaa taaccggaga aaaagtgaaa agttttcata       120
ctgatttaag ctcccggaca ggtgaacgag tgatggtatt taaattatgt aatgatctag       180
agaaaaattt ggaaaagatc ttataatcta aagaaaataa atgttttgac ggtgtggaat       240
ttgttgtgaa ttgaacataa agaactgccg attcttttgt tttacaatta tggtatcatt       300
gataactttt attcatatcc taagcggaca taaagagatg tcaattcata gtacactgtc       360
atgttattcc tgtcgaaaga tctaacatcc gctgttgtta tgagcggatg ttttttttaca      420 tctattttaa atacatgaat ttgatgctgg tgattagtca cttgaacaat atttgaaaac       480
atccttgtca cctgccgggt ttccccaagt gtttagtgac atgattatga gaccaacttc       540
gtaaagcttg ctgataaatt taagcggtga acaaaattga tatgctgtct tcagtttcat       600
ttcacggaat tagtcagaga taaacctta attaaatata tccaaaaaac ggattgacat        660
atcgaaatat aacgatataa taatcgatat ggaaccaatt gaagtattca aagccttatc       720
aaatgaatca aggctgcaaa ttttacaatg gctgaaggag cccgatcgtc attttgcacc       780
ccatgaaggg attgatatga acacaatcgg ggtatgtgtc agtcaaataa cagacaaatt       840
gaaaatgacg caatcgacag cttctcaata tcttaccatc cttttaagag ccggcctaat       900
taaggcggag cgaatcggaa agtacacgta ttataaaaga gatgaagaag ccattgggaa       960
acttgctgac tttcttaaaa cagagatata aaaataaaca tcaaaagatg tttattttta      1020
caccatacat atcgacatat tacgatgtgt ttatttttt ataataacat atcgataatt       1080
cgtgatatgt ttattaataa ttaaggagtg aatgtttat gtctaacact tggaaaattt       1140 atatttttagc cattgtcagc ttttttagttg gaacctcaga gtacatcatt tccggaattt     1200
tggatcaaat tgctcatact ctcgggatca ctttagctgc cgcgggccag cttattacca      1260
ttttctcact tgtatatgct cttttctacac ccgtacttat ggcgttgaca gcaagtatgg     1320
atagacgcaa attgatgatg tatgccctag gtttgtttgt gttcggtaat gtcctggctt      1380
ttgtactgcc tggttatgga tggtttattg cagcgcggat cattatggcg atgggagcag      1440
gtgtggttgt tgtcaccgca ttaacgattg ccgctaagat tgcatcggaa gggaagcagg      1500
gcagtgccat cgctacggtc gtgatgggat ttaccgcttc tttaatcatt ggtgttccgc      1560
ttggaagaat gatagcagta gcattaggct ggaagtctgt atttggagcc attgctttgt      1620
tgggattgat cgcaatggtc gttattttct ttactcttcc gtatactgaa ggggataagc      1680
ctgtgccttt gcttcaacag cttgctcttt tcaaaaaacg gaaagtggct atgggattat      1740
caatcacttt cttctggctc gggggatatt ctgttgctta cacttatttg tcaccgtatc      1800
tcttgaacat ctcaggtata aatggcaagc tgctcagcgg tgttttgctt atatttggaa      1860
ttgccagttt ggttggatcg aagtttgggg gatatagcac cgataaatgg ggagtgccct      1920
ttacactcgt tggcgggatg acgttgcata tcgtcacact gattctgctg tcacttgtta     1980
```

-continued

```
ctcattccta tatcggagtg ttggtgattc tcatattatg gtcgtttgcc gcatggtcca   2040
ccggtccgac acagcaattt cacctggcta caatagaacc ggaaatgtca ggtgtttttgc  2100 ttagcatgaa tcagtcaatg atgcaattcg ccatggcggt cggcgcaggt ataggagggg   2160
tttttgtgga aaacgtatca ttggcctcga ttacctgggt tggtgcgtta ggggttatga   2220
ttgcaattat tgcatcattg ctgattttca attcgcaacc gaaacaagcg ctaaaagata   2280
tcaatcaata atttcgaaag ttctaacatc cgctcgttat acaagcgggt gtttttttta   2340
gcgtagtcag tccatgcatg agtcttccaa gggccgacat cgttctgtat gtgtcgaagg   2400
tgcactgaag ctgaatgaga tttcttaagg ctttgccgcg gcgagctgaa gtacagtacg   2460
attgccttga tcgaacactg gaaacacaag agaacgtaaa cctgaacatc cgcgtaaacg   2520
tcaaggaagt tgccacttgg ggagtaaaca cttgcatcat ctcgctgaaa ggcctagaca   2580
atgcggatga cagattcgta ttgccggaag taaacacagc gcttgctctg tttccgttgt   2640
cgattgcagc tgattgctta ctaatgctgc cctgcatctc ggttgtgatg tcgataagca   2700
gcgtaatgaa gagtgttact gtggagtaag atgtttaacc cctctggata ttttagccga   2760
aggggttttt agtatagata tttgatttaa attacaggag acttcattca tttaaccaaa   2820
gtcattgctt tcttaatcac taaagtttat ttgaaaataa tctcttgatt taatttcctc   2880
gaagagattt tttgtcaatc tattaggcat cagaattttt ataacataat ggaccgtctt   2940
tttgacgttt tgtttataga acaagaaaat attcaaaaca taagtggaaa attaggggtg   3000
agctccggtc cttcctataa gcaggaaggt tttttaatga aatatttttt tattagtagg   3060
taaattcatc aaatgttctg ctatgctcca aatgtacacc tttccgtaag ggcaaagtca   3120
aatgtgaaaa aaaactgttc caaagttaat cagaaattta ttttcatatt gtatccttcg   3180
gtatcaagtg aaaggagcat catatgaaaa cattatggaa agtcctcaaa attgtttttg   3240
tcagcttggc tgctttggtt ttgcttgtat ccgtctcggt atttatttat caccatttcc   3300
agctaaataa ggaggcggca ctgctgaaag gtaaaggcac agtagtcgat gttgacggta   3360
aaaagatgaa tgtgtatcaa gagggaagcg ggaaggatac gtttgtgttt atgtccggtt   3420
cgggtattgc tgcgcctgct tatgaaatga aggggctgta cagcaagttt tcaaaagaaa   3480
ataagattgc tgttgtagat cgggcaggtt atggatacag tgaagtgtct cacgatgaca   3540
gagatattga tacggtattg gaacagacga ggaaagcgct tatgaaaagc ggaaataagc   3600
ctccttatat tttaatgcct cattcgatat ccgggattga agcgatgtat tgggcacaga   3660
aatatcctaa ggaaatcaag gccattattg cgatggatat tggattgccc cagcagtacg   3720
tcacgtataa attgagcgga gttgaccgat tgaaagtgag agggttccac ctgttaacct   3780
cgattggttt tcatcggttt ataccttccg ctgtatataa tcctgaggtg attcgacagt   3840 cgttttttaac tgatgaagaa aaagaaatct ataaagccat taactttaag caattttttta  3900 atgcagatat ggagcatgag ctttttacagt cttaccaaaa cggcagcaaa tctgtgaatc   3960
tgcctgcgcc aaaggaaact cccgtcttga ttttagatgc agtctctgac caaaatagac   4020
attcaaagta tgctatacaa aaccgaaaag actatgaagc gtttgcggct caattcaata   4080
ctgccgatat aaaggaactg aggggaacac acagtattta tttatatcag cctgatcaaa   4140
tatataaact gtccatggag tttatgagaa aggttcgcta ggatgaaggg ttatcgtatt   4200
ttaatcgttg aggacgatgt gatgattggt gatttgctgc aaaagatttt gcagcgcgag   4260
ggatatcgtg tgatatggaa aacagatgga gcggatgtgc tttcggtgat tcagaaggtg   4320
```

```
gatttggtca ttatggatgt gatgctgccg ggtgaagacg ggtatcaaat gtctgcaaaa    4380
atcaaaaagc tggggctggg cattccggtt attttttctct cagcccgcaa tgacatggac    4440
agcaagcttc aaggtttgca gatcggcgag gattatatgg taaagccctt tgatccgaga    4500
gagctgctat taagaatgcg gaatatgctt gagcatcatt atgggacctt tacgcaaatc    4560
aaacatttgt atattgatgc ggtaacgaaa aaagtgttca atgaaagcct gcatgatgag    4620
gtattattta ctgcgattga gcggaaaatt ttctttttatt tatatgaaaa tagagacagt    4680
atcctgacaa aggaacattt ctttgaatat ctatggcagc tcgaagatag aaacccgaat    4740
attgtcaatg tgcatattaa aaaaattaga gctaaaatca atgatcaagc gggtgagatg    4800
attgaaaata tatatggaga agggtatcgg ctgaataccg ttgtgaagaa atgaagctca    4860
agacaaaata tcagttgtta ttgtttacgg ccgtcattag tgttccgatg ctattgctgg    4920
cggtcagtgt tttgatgtcg gtgatttatg acagcatgtt taaaccgatg aatcatggta    4980 tgcccttttca caggtcgttt gcatacccgg caatgatcgt tgtattttttg atatcactct    5040 tattgttagc tttttttattt tcaaagtcga ttcattctct gttgcataaa atcaatctat    5100
taaatcaaac cattcggcat ttggcgagtg atcaaagggt gcccgataaa attgaagtga    5160
agcgtgctga tgaaatcggg gaactgatca agtcggtcaa tttgttaatt gaacggacga    5220
catatcgtga actggagctg agacagcagg aggaaatcaa aaaggagctt ttgcaaaaac    5280
tgcggcatga cattaataca cctttaacgg ctctcaggct gcagttattt tatttggaag    5340
accaatgtca tggtcaggct gtattcgaat cattgtatca gcaaatcgaa tatatctcgg    5400
aattaactaa tgaattcaat ctatattccg ctgagacgct ggaaagctct tatattgtaa    5460
atgaagaagt gcgtctaaac gagctattag aaacagcggt gaaaaagtgg gattatttat    5520
acagtatgag tgggattgag ctgcactata agccggcaga tcaagatgtg atatggatga    5580
gcaacacgtt atggatggaa aggctgtttg ataatatttt tcaaaatacg ttaaggcatt    5640
caaaagctaa aaagatggaa gtcacgattg aacatggcga tgtttttatt cgtgatgacg    5700
gtattggatt tgatcggaat gagagcagtg agggacttgg gttaaagatt attgaggata    5760
catgcaggct gcttgcgatt acttatgagc tgcatacaaa tgataacgga acggggttct    5820
tgttttcaaa agagtgaccc cgctgatgtt tttctttctc ctataaaatt tatataatag    5880
ggagaaagaa atggggtgaa catcatatgt ttaaaaaaat catcaaaacg attaagtacc    5940
tctcaagcag ttctagtgac cgatatcgca gacaccggca ttacagcagc agccggcgca    6000
gacattatcg cagctac                                                     6017
```

<210> SEQ ID NO 35
<211> LENGTH: 3006
<212> TYPE: DNA
<213> ORGANISM: Bacillus subtilis

<400> SEQUENCE: 35

```
gatcaaaaga gggtatgtta tctatcaaac aaactcgttc agagttagtc gaatcaggta      60
tagaaggcct taaggatatt atcttaaaaa taaccggaga aaaagtgaaa agttttcata     120
ctgatttaag ctcccggaca ggtgaacgag tgatggtatt taaattatgt aatgatctag     180
agaaaaattt ggaaaagatc ttataatcta agaaaataa atgtttgac ggtgtggaat       240 ttgttgtgaa ttgaacataa agaactgccg attcttttgt tttacaatta tggtatcatt     300
gataactttt attcatatcc taagcggaca taaagagatg tcaattcata gtacactgtc     360
atgttattcc tgtcgaaaga tctaacatcc gctgttgtta tgagcggatg ttttttttaca    420
```

-continued

```
tctattttaa atacatgaat ttgatgctgg tgattagtca cttgaacaat atttgaaaac      480
atccttgtca cctgccgggt ttccccaagt gtttagtgac atgattatga gaccaacttc      540
gtaaagcttg ctgataaatt taagcggtga acaaaattga tatgctgtct tcagtttcat      600
ttcacggaat tagtcagaga taaaccttta attaaatata tccaaaaaac ggattgacat      660
atcgaaatat aacgatataa taatcgatat ggaaccaatt gaagtattca aagccttatc      720
aaatgaatca aggctgcaaa ttttacaatg gctgaaggag cccgatcgtc attttgcacc      780
ccatgaaggg attgatatga acacaatcgg ggtatgtgtc agtcaaataa cagacaaatt      840
gaaaatgacg caatcgacag cttctcaata tcttaccatc cttttaagag ccggcctaat      900
taaggcggag cgaatcggaa agtacacgta ttataaaaga gatgaagaag ccattgggaa      960
acttgctgac tttcttaaaa cagagatata aaaataaaca tcaaaagatg tttattttta     1020
caccatacat atcgacatat tacgatgtgt ttattttttt ataataacat atcgataatt     1080
cgtgatatgt ttattaataa ttaaggagtg aatgttttat gtctaacact tggaaaattt     1140
atattttagc cattgtcagc tttttagttg gaacctcaga gtacatcatt tccggaattt     1200
tggatcaaat tgctcatact ctcgggatca ctttagctgc cgcgggccag cttattacca     1260
ttttctcact tgtatatgct ctttctacac ccgtacttat ggcgttgaca gcaagtatgg     1320
atagacgcaa attgatgatg tatgccctag gtttgtttgt gttcggtaat gtcctggctt     1380
ttgtactgcc tggttatgga tggtttattg cagcgcggat cattatggcg atgggagcag     1440
gtgtggttgt tgtcaccgca ttaacgattg ccgctaagat tgcatcggaa gggaagcagg     1500
gcagtgccat cgctacggtc gtgatgggat ttaccgcttc tttaatcatt ggtgttccgc     1560
ttggaagaat gatagcagta gcattaggct ggaagtctgt atttggagcc attgctttgt     1620
tgggattgat cgcaatggtc gttattttct ttactcttcc gtatactgaa ggggataagc     1680
ctgtgccttt gcttcaacag cttgctcttt tcaaaaaacg gaaagtggct atgggattat     1740
caatcacttt cttctggctc gggggatatt ctgttgctta cacttatttg tcaccgtatc     1800
tcttgaacat ctcaggtata aatggcaagc tgctcagcgg tgtttttgctt atatttggaa     1860 ttgccagttt ggttggatcg aagtttgggg gatatagcac cgataaatgg ggagtgcect     1920 ttacactcgt tggcgggatg acgttgcata tcgtcacact gattctgctg tcacttgtta     1980
ctcattccta tatcggagtg ttggtgattc tcatattatg gtcgtttgcc gcatggtcca     2040
ccggtccgac acagcaattt cacctggcta caatagaacc ggaaatgtca ggtgttttgc     2100
ttagcatgaa tcagtcaatg atgcaattcg ccatggcggt cggcgcaggt ataggagggg     2160
tttttgtgga aaacgtatca ttggcctcga ttacctgggt tggtgcgtta ggggttatga     2220
ttgcaattat tgcatcattg ctgatttttca attcgcaacc gaaacaagcg ctaaaagata     2280
tcaatcaata atttcgaaag ttctaacatc cgctcgttat acaagcgggt gtttttttta     2340
gcgtagtcag tccatgcatg agtcttccaa gggccgacat cgttctgtat gtgtcgaagg     2400
tgcactgaag ctgaatgaga tttcttaagg ctttgccgcg gcgagctgaa gtacagtacg     2460
attgccttga tcgaacactg gaaacacaag agaacgtaaa cctgaacatc gcgtaaacg      2520 tcaaggaagt tgccacttgg ggagtaaaca cttgcatcat ctcgctgaaa ggcctagaca     2580
atgcggatga cagattcgta ttgccggaag taaacacagc gcttgctctg tttccgttgt     2640
cgattgcagc tgattgctta ctaatgctgc cctgcatctc ggttgtgatg tcgataagca     2700
gcgtaatgaa gagtgttact gtggagtaag atgtttaacc cctctggata ttttagccga     2760
```

-continued

| | | |
|---|---|---|
| aggggtttttt agtatagata tttgatttaa attacaggag acttcattca tttaaccaaa | 2820 | |
| gtcattgctt tcttaatcac taaagtttat ttgaaaataa tctcttgatt taatttcctc | 2880 | |
| gaagagattt tttgtcaatc tattaggcat cagaattttt ataacataat ggaccgtctt | 2940 | |
| tttgacgttt tgtttataga acaagaaaat attcaaaaca taagtggaaa attaggggtg | 3000 | |
| agctcc | 3006 | |

```
<210> SEQ ID NO 36
<211> LENGTH: 3032
<212> TYPE: DNA
<213> ORGANISM: Bacillus subtilis

<400> SEQUENCE: 36
```

| | | |
|---|---|---|
| ggaaaattag gggtgagctc cggtccttcc tataagcagg aaggtttttt aatgaaatat | 60 | |
| ttttttatta gtaggtaaat tcatcaaatg ttctgctatg ctccaaatgt acacctttcc | 120 | |
| gtaagggcaa agtcaaatgt gaaaaaaaac tgttccaaag ttaatcagaa atttattttc | 180 | |
| atattgtatc cttcggtatc aagtgaaagg agcatcatat gaaaacatta tggaaagtcc | 240 | |
| tcaaaattgt ttttgtcagc ttggctgctt tggttttgct tgtatccgtc tcggtattta | 300 | |
| tttatcacca tttccagcta aataaggagg cggcactgct gaaaggtaaa ggcacagtag | 360 | |
| tcgatgttga cggtaaaaag atgaatgtgt atcaagaggg aagcgggaag gatacgtttg | 420 | |
| tgtttatgtc cggttcgggt attgctgcgc ctgcttatga aatgaagggg ctgtacagca | 480 | |
| agttttcaaa agaaaataag attgctgttg tagatcgggc aggttatgga tacagtgaag | 540 | |
| tgtctcacga tgacagagat attgatacgg tattggaaca gacgaggaaa gcgcttatga | 600 | |
| aaagcggaaa taagcctcct tatattttaa tgcctcattc gatatccggg attgaagcga | 660 | |
| tgtattgggc acagaaatat cctaaggaaa tcaaggccat tattgcgatg gatattggat | 720 | |
| tgccccagca gtacgtcacg tataaattga gcggagttga ccgattgaaa gtgagagggt | 780 | |
| tccacctgtt aacctcgatt ggttttcatc ggtttatacc ttccgctgta tataatcctg | 840 | |
| aggtgattcg acagtcgttt ttaactgatg aagaaaaaga aatctataaa gccattaact | 900 | |
| ttaagcaatt tttttaatgca gatatggagc atgagctttt acagtcttac caaaacggca | 960 | |
| gcaaatctgt gaatctgcct gcgccaaagg aaactcccgt cttgatttta gatgcagtct | 1020 | |
| ctgaccaaaa tagacattca aagtatgcta tacaaaaccg aaaagactat gaagcgtttg | 1080 | |
| cggctcaatt caatactgcc gatataaagg aactgagggg aacacacagt atttatttat | 1140 | |
| atcagcctga tcaaatatat aaactgtcca tggagtttat gagaaaggtt cgctaggatg | 1200 | |
| aagggttatc gtattttaat cgttgaggac gatgtgatga ttggtgattt gctgcaaaag | 1260 | |
| attttgcagc gcgagggata tcgtgtgata tggaaaacag atggagcgga tgtgctttcg | 1320 | |
| gtgattcaga aggtggattt ggtcattatg gatgtgatgc tgccgggtga agacgggtat | 1380 | |
| caaatgtctg caaaaatcaa aaagctgggg ctgggcattc cggttatttt tctctcagcc | 1440 | |
| cgcaatgaca tggacagcaa gcttcaaggt ttgcagatcg gcgaggatta tatggtaaag | 1500 | |
| ccctttgatc cgagagagct gctattaaga atgcggaata tgcttgagca tcattatggg | 1560 | |
| acctttacgc aaatcaaaca tttgtatatt gatgcggtaa cgaaaaaagt gttcaatgaa | 1620 | |
| agcctgcatg atgaggtatt atttactgcg attgagcgga aaattttctt ttatttatat | 1680 | |
| gaaaatagag acagtatcct gacaaaggaa catttctttg aatatctatg gcagctcgaa | 1740 | |
| gatagaaacc cgaatattgt caatgtgcat attaaaaaaa ttagagctaa aatcaatgat | 1800 | |
| caagcgggtg agatgattga aaatatatat ggagaagggt atcggctgaa taccgttgtg | 1860 | |

-continued

```
aagaaatgaa gctcaagaca aaatatcagt tgttattgtt tacggccgtc attagtgttc      1920
cgatgctatt gctggcggtc agtgtttga tgtcggtgat ttatgacagc atgtttaaac      1980
cgatgaatca tggtatgccc tttcacaggt cgtttgcata cccggcaatg atcgttgtat      2040
ttttgatatc actcttattg ttagctttt tattttcaaa gtcgattcat tctctgttgc      2100
ataaaatcaa tctattaaat caaaccattc ggcatttggc gagtgatcaa agggtgcccg      2160
ataaaattga agtgaagcgt gctgatgaaa tcggggaact gatcaagtcg gtcaatttgt      2220
taattgaacg gacgacatat cgtgaactgg agctgagaca gcaggaggaa atcaaaaagg      2280
agcttttgca aaaactgcgg catgacatta atacaccttt aacggctctc aggctgcagt      2340
tattttattt ggaagaccaa tgtcatggtc aggctgtatt cgaatcattg tatcagcaaa      2400
tcgaatatat ctcggaatta actaatgaat tcaatctata ttccgctgag acgctggaaa      2460
gctcttatat tgtaaatgaa gaagtgcgtc taaacgagct attagaaaca gcggtgaaaa      2520
agtgggatta tttatacagt atgagtggga ttgagctgca ctataagccg gcagatcaag      2580
atgtgatatg gatgagcaac acgttatgga tggaaaggct gtttgataat atttttcaaa      2640
atacgttaag gcattcaaaa gctaaaaaga tggaagtcac gattgaacat ggcgatgttt      2700
ttattcgtga tgacggtatt ggatttgatc ggaatgagag cagtgaggga cttgggttaa      2760
agattattga ggatacatgc aggctgcttg cgattactta tgagctgcat acaaatgata      2820
acggaacggg gttcttgttt tcaaaagagt gaccccgctg atgttttct ttctcctata      2880 aaatttatat aatagggaga aagaaatggg gtgaacatca tatgtttaaa aaaatcatca      2940
aaacgattaa gtacctctca agcagttcta gtgaccgata tcgcagacac cggcattaca      3000
gcagcagccg gcgcagacat tatcgcagct ac                                    3032
```

<210> SEQ ID NO 37
<211> LENGTH: 6087
<212> TYPE: DNA
<213> ORGANISM: artificial sequence
<220> FEATURE:
<223> OTHER INFORMATION: synthesized sequence

<400> SEQUENCE: 37

```
cgcccggcaa gagaacaaga ccagatgcaa atgcagtgag gactaagccg ccttgcagat       60
acatcggcag aagcagcata gatgacagaa tgaccatcat acaaatgaac accatgatca      120
cacccaaaat aaacatcggg tatttgaacg cacggaggtt catcataggc tgcttcattg      180
tcagctggcg gattgaaaat aagataaggc cgacaacgcc gacaatcagc gacacgataa      240
cagtcgggct ggaccatccc ccggagcctt cacccgcgtt gctgaatccg aatacaatgc      300
cgccgaagcc aatcgtcgac aggatgatag acaatacatc gattttcggc tttgtcgttt      360
cagatacatt ttgcatatat gcgataccga aaacaagcgc cagcacaagg aatggaagag      420
agatccagaa aatccagtgc cagttgagat gctccagaac caatcctgag aaagttgggc      480
cgatggcggg cgcgaacata atgacaagcc cgatcgttcc cattgcggca ccccgtttat      540
gaggcgggaa aatcaccaag attgtgttaa acatcagcgg cagtaaaaga ccggttccaa      600
gtgcctgaac gatccttgcc gctaataaaa acgagaagc cggcgcaagc gccgcaatga      660
atgtacctaa aattgaaaag ataagtgaca cggtaaaaag ctgtcttgtt gtgaaccact      720
gcaacagcag tcctgaaaca ggaacaagga taccgagtac aagcaggtag cccgtcgtta      780
accattggac ggttgccgct gtaatgttca attccttcat aaggtcggtt aacgcaatat      840
```

-continued

```
tcagcgctgt ttcactgaac atgccgataa aaccggccaa cagcaaggaa atcataatcg      900
gcatcacttt gtattgctga gatgctttag ctgttgtttc caaaatcatt tcccctctct      960
atcaactgca tgtagtatgt cgtttttttt atctcttcag caggtcagga atgcagctgg     1020
agatatgaag gagcggcgta ctgttttttg ccgtcaaaga taaaaggatg ccgccttcaa     1080
tcatcgcgtt aaccacagtg ctggcttctt ttgcacggct ctcgctgcag ccagtctgcc     1140
gcagtttttc ctcatacaca gaggcccatt ctttgtaggc ttcatgacag gcttcgcgca     1200
acggttcgct tttcaatgac gtctcagccg ctagcaagcc cacaggcaag ccttcaatgt     1260
cttccgtaca tgaaaactgg caggagagct ccttcaaaaa ggcttgaatg ccttccgctg     1320
gatcggtgca ggcttccatg cagtccgcga tttctgacg gatatactcc ttcatctcat     1380
tcacggcttc gatcgcaagc tgttctttac ccccgggaaa gtggtagtaa agagagcctt     1440
taggcgcgcc gctttccttt ataatctggt tcagccccgt gccgtaatac ccttgcagct     1500
gaaaaagccg ggtagctgcc gaaaggattt tctcacggga atctccataa ctcataacat     1560
tcccacctta ctgaattgca atcaaaaata tagtgactgg tctattatct tgattcaatc     1620
atcaattgtc aagaaaaatt cattgtatga aaagacaaaa aaagaaggat atgacaacaa     1680
aaaatactga gagaaaagct gactgatctt ttgactgaat agataaaatg tacaatgatt     1740
aatcatcata tggatgtaag gagagaaata gatgaaaaaa caacgaatgc tcgtactttt     1800
taccgcacta ttgtttgttt ttaccggatg ttcacattct cctgaaacaa aagaatcccc     1860
gaaagaaaaa gctcagacac aaaaagtctc ttcggcttct gcctctgaaa aaaaggatct     1920
gccaaacatt agaattttag cgacaggagg cacgatagct ggtgccgatc aatcgaaaac     1980
ctcaacaact gaatataaag caggtgttgt cggcgttgaa tcactgatcg aggcagttcc     2040
agaaatgaag gacattgcaa acgtcagcgg cgagcagatt gttaacgtcg gcagcacaaa     2100
tattgataat aaaatattgc tgaagctggc gaaacgcatc aaccacttgc tcgcttcaga     2160
tgatgtagac ggaatcgtcg tgactcatgg aacagataca ttggaggaaa ccgcttattt     2220
tttgaatctt accgtgaaaa gtgataaacc ggttgttatt gtcggttcga tgagaccttc     2280
cacagccatc agcgctgatg ggccttctaa cctgtacaat gcagtgaaag tggcaggtgc     2340
ccctgaggca aaagggaaag ggacgcttgt tgttcttaac gaccggattg cctcagcccg     2400
atatgtcacc aaaacaaaca caactacaac agatacattt aaatcagaag aaatgggctt     2460
cgtcggaaca attgcagatg atatctattt taataatgag attacccgta agcatacgaa     2520
ggacacggat ttctcggttt ctaatcttga tgagctgccg caggttgaca ttatctatgg     2580
ataccaaaat gacggaagct acctgtttga cgctgctgta aaagccggag caaaggggat     2640
tgtatttgcc ggttctggga acgggtcttt atctgatgca gccgaaaaag gggcggacag     2700
cgcagtcaaa aaaggcgtta cagtggtgcg ctctacccgc acgggaaatg tgtcgtcac      2760 accaaaccaa gactatgcgg aaaaggactt gctggcatcg aactctttaa acccccaaaa     2820
agcacggatg ttgctgatgc ttgcgcttac caaaacaaat gatcctcaaa aaatccaagc     2880
ttatttcaat gagtattgaa gaaaagaagg cgaataagcc ttctttttttt tggctttta     2940 ggaccaataa tgacctctga atcttaaaat ttctttaaaa ataagccaaa attacccttt     3000
acttaattaa tttggtaacg taatataatt ggagaatttg gttattctgc tttcagcaca     3060
atggttttcg cagccatatc atgaacggtt tgtttttttct tcgtaaatgc ggcagtcaaa     3120
tagatcaggc gggagaacac atgcacccac gctatcaggt aacggacaat ggcttgcggg     3180
aaggatattt ttttatatgt ttcgtccctc acgatttgca gcccgatgat ttttttgccc     3240
```

-continued

```
agtgtgccct tccaatttgt cagcggcatc agcaaagggt acacaatcag catcaatatg    3300
gcgacaataa tgacaccggc ggacccatcg ccaaacgtaa atccggctgc caaaatcact    3360
gctgcggcaa tgattacatc aagtaaaaga gcgcaggcgc gcagcatgaa accagctagt    3420
tccaatagaa acactcctta aaatgttaaa taaacaccta atgattgtaa aaaagaaggg    3480
cctaaagtgg gaataggtga taagccttaa atcacaaaag ttggtgaaaa tgtcataggt    3540
aaattggcat aatcagccag cttatcacat taccaaattc ttttttagcc cgaaaccaag    3600
ccctcagaag ttattttttgt taaaatagaa aagttacaac agaattcgga gggtttattg    3660
tgggaaaagt gaaacgaaat gccccttgcc catgcggcag cggcaagaaa tataaaaaat    3720
gctgcggaag taaagttgtc gacttcccgg cggaactagc ggcaaaagaa gcgaaacaaa    3780
ttcaggaaga cttagtggag tatgccttca cagtacatag agaaagcatt tcaggcttta    3840
tcaaccagca tgattttctt tctgctatgg acagacagac gaaagacatc agcgtattta    3900
acttaggaat ctggggaatc ttcttccacc cgcttgctgg tgagaagaca atcttcgaag    3960
agtaccttca gaaaaaaggc gattcgatca ctcgtccgaa aacgcgtgag atcgtagaat    4020
catggcagag catgacgcct gctttattgc tgctgaagga cctgaaggaa ggcatcattc    4080
actttgaaga tgtcattacg gcaaaacaat tcgaagtgga aatggacgcc agcaatcaag    4140
accttcctcc agtgggaagc ctgattcttg gatacccaat ccacgaagcg gaaaaagcag    4200
aattcttcat gcagttcacg atcttcccgg tgaagagaac agaagcgctg atcagcaagg    4260
tgaagaaata tgcggatgcc gctgtgaagg acggcaaaac gccggaggac ttcatgaagc    4320
aggaattcaa caacgttctg ttcgcgttgt tagctgagaa agatgaagag ccacaagcag    4380
agaaagcgga agtaagcact gttgagtggg caaacgactt ggagaaagaa accgctgcgg    4440
ctattgaaga aggcatgagc ggggaagagt atccgactga attgatccca gctgttattg    4500
acatctggaa aacattctgc gagaaaaaat cacctgtcat cagaaagccg gaagcttttg    4560
cggcggcagt tgaatattat gtaaacgcaa tttctcttaa cggcgcgtcc gtttcccagg    4620
ctaaactggc gaaaaaatac ggcgttagcg catcaacgat ttccagccgt tacaaagaaa    4680
ttgaaagcac gctgcaagat gaagcagatc gttttgcaca agcgttatcc tcataatgga    4740
aaaaaccttg aaaagccagg cttttcaagg ttttttttatt tctgaaacgg aattttgatt    4800
tctaaccgga agatggggtg gcggtaggta aaatccagcc tgccaaaagc gcccttcacc    4860
agtttttgaa tgatatatgt gcccatgcct tcatgagcgc cgttttttcgt tgagcggcca    4920 aacgattgat aaattgtatc gagcacttttt gggtccatcc cgggagtgct gttttcacaa    4980
gtcagtacat aaagcccgct gcgcagtgaa gtctccagtt taatctctgc tttttctcgg    5040
gcctccgccg cgctgtcgag cgcatttttct aatatgttgc cgaccaagct gacctgatca    5100
gcaggcgaaa acggaaggga agaaagcggt gtatgcatat gcagcgaaac actcacattc    5160
gaggcgcggg cttttttctaa aaaatcataa agcaccccttg caacgtacgc gttctctcct    5220
ttcaaaaaac ggtcatattg gctgtattga tccgcccagt tttgaatata tgcttgtgta    5280
tctgccttgg gctgagctga tttgattgca gtgatatgtt tcattgtgtc atgattccgg    5340
cttctgacat caatcagcat ttgattggcg tgctgttcag cttgagtcag cttatcaatt    5400
tgatcagaaa gccttgcctg caaagcagac tgtccgatac ggagcccttc acaccctgca    5460
aatatcgcga ttacacataa taccggcatg atgtctgtgc caatcaacac cactcccacc    5520
gacatcactt gaatcaccgc aatccacgca caaagccctg aggaacagtg tttccacacc    5580
```

-continued

```
cgcttcgtat tccaaatgta caatcctgca gcagctgcgc ctaaagcagc ggcgagccaa    5640
gaggcggctg tgctgtgtga aaaagcagca gctccctgat aacatatgaa actaaataaa    5700
atcagataaa gacattgaaa aagggtaatc acgtactaaa ctcctcaaaa atagtagttt    5760
tgaaaataat caagctgctg cttagtgatc atcgcttttt tagacgttcc ctcaaaggaa    5820
actgtgaatg aatgcttggt ataagcggaa aaatgcttta tgtaatgaat gttgataata    5880
aaggaacgat gcgaacgaag aaaatctttt tcgggcaggt cgcctttaat atcatttaat    5940
gtttgatacg tttgcacctc ttcggcggtt gtcacaatcg tcgtcgaacg tcccgtccgt    6000
tctgcgaaaa taatatcctt cttttgcagg acgtgcattt cagacttttg ctttatcaat    6060
atacgcccat tcaaactcgt ttccgtt                                        6087

<210> SEQ ID NO 38
<211> LENGTH: 3040
<212> TYPE: DNA
<213> ORGANISM: Bacillus subtilis

<400> SEQUENCE: 38
cgcccggcaa gagaacaaga ccagatgcaa atgcagtgag gactaagccg ccttgcagat      60
acatcggcag aagcagcata gatgacagaa tgaccatcat acaaatgaac accatgatca     120
cacccaaaat aaacatcggg tatttgaacg cacggaggtt catcataggc tgcttcattg     180
tcagctggcg gattgaaaat aagataaggc cgacaacgcc gacaatcagc gacacgataa     240
cagtcgggct ggaccatccc ccggagcctt cacccgcgtt gctgaatccg aatacaatgc     300
cgccgaagcc aatcgtcgac aggatgatag acaatacatc gattttcggc tttgtcgttt     360
cagatacatt ttgcatatat gcgataccga aaacaagcgc cagcacaagg aatggaagag     420
agatccagaa aatccagtgc cagttgagat gctccagaac caatcctgag aaagttgggc     480
cgatggcggg cgcgaacata atgacaagcc cgatcgttcc cattgcggca ccccgtttat     540
gaggcgggaa aatcaccaag attgtgttaa acatcagcgg cagtaaaaga ccggttccaa     600
gtgcctgaac gatccttgcc gctaataaaa acgagaagct cggcgcaagc gccgcaatga     660
atgtacctaa aattgaaaag ataagtgaca cggtaaaaag ctgtcttgtt gtgaaccact     720
gcaacagcag tcctgaaaca ggaacaagga taccgagtac aagcaggtag cccgtcgtta     780
accattggac ggttgccgct gtaatgttca attccttcat aaggtcggtt aacgcaatat     840
tcagcgctgt ttcactgaac atgccgataa aaccggccaa cagcaaggaa atcataatcg     900
gcatcacttt gtattgctga gatgctttag ctgttgtttc caaaatcatt tcccctctct     960
atcaactgca tgtagtatgt cgtttttttt atctcttcag caggtcagga atgcagctgg    1020
agatatgaag gagcggcgta ctgttttttg ccgtcaaaga taaaaggatg ccgccttcaa    1080
tcatcgcgtt aaccacagtg ctggcttctt ttgcacggct ctcgctgcag ccagtctgcc    1140
gcagtttttc ctcatacaca gaggcccatt cttttgtaggc ttcatgacag gcttcgcgca    1200
acggttcgct tttcaatgac gtctcagccg ctagcaagcc cacaggcaag ccttcaatgt    1260
cttccgtaca tgaaaactgg caggagagct ccttcaaaaa ggcttgaatg ccttccgctg    1320
gatcggtgca ggcttccatg cagtccgcga ttttctgacg gatatactcc ttcatctcat    1380
tcacggcttc gatcgcaagc tgttctttac ccccgggaaa gtggtagtaa agagagcctt    1440
taggcgcgcc gctttccttt ataatctggt tcagccccgt gccgtaatac ccttgcagct    1500
gaaaaagccg ggtagctgcc gaaaggattt tctcacggga atctccataa ctcataacat    1560
tcccacctta ctgaattgca atcaaaaata tagtgactgg tctattatct tgattcaatc    1620
```

-continued

```
atcaattgtc aagaaaaatt cattgtatga aaagacaaaa aaagaaggat atgacaacaa      1680
aaaatactga gagaaaagct gactgatctt ttgactgaat agataaaatg tacaatgatt      1740
aatcatcata tggatgtaag gagagaaata gatgaaaaaa caacgaatgc tcgtactttt      1800
taccgcacta ttgtttgttt ttaccggatg ttcacattct cctgaaacaa aagaatcccc      1860
gaaagaaaaa gctcagacac aaaaagtctc ttcggcttct gcctctgaaa aaaaggatct      1920
gccaaacatt agaattttag cgacaggagg cacgatagcc ggtgccgatc aatcgaaaac      1980
ctcaacaact gaatataaag caggtgttgt cggcgttgaa tcactgatcg aggcagttcc      2040
agaaatgaag gacattgcaa acgtcagcgg cgagcagatt gttaacgtcg gcagcacaaa      2100
tattgataat aaaatattgc tgaagctggc gaaacgcatc aaccacttgc tcgcttcaga      2160
tgatgtagac ggaatcgtcg tgactcatgg aacagataca ttggaggaaa ccgcttattt      2220
tttgaatctt accgtgaaaa gtgataaacc ggttgttatt gtcggttcga tgagaccttc      2280
cacagccatc agcgctgatg ggccttctaa cctgtacaat gcagtgaaag tggcaggtgc      2340
ccctgaggca aaagggaaag ggacgcttgt tgttcttaac gaccggattg cctcagcccg      2400
atatgtcacc aaaacaaaca caactacaac agatacattt aaatcagaag aaatgggctt      2460
cgtcggaaca attgcagatg atatctattt taataatgag attacccgta agcatacgaa      2520
ggacacggat ttctcggttt ctaatcttga tgagctgccg caggttgaca ttatctatgg      2580
ataccaaaat gacggaagct acctgtttga cgctgctgta aaagccggag caaaggggat      2640
tgtatttgcc ggttctggga acgggtcttt atctgatgca gccgaaaaag gggcggacag      2700
cgcagtcaaa aaaggcgtta cagtggtgcg ctctacccgc acgggaaatg tgtcgtcac       2760 accaaaccaa gactatgcgg aaaaggactt gctggcatcg aactctttaa accccccaaaa     2820 agcacggatg ttgctgatgc ttgcgcttac caaaacaaat gatcctcaaa aaatccaagc      2880
ttatttcaat gagtattgaa gaaaagaagg cgaataagcc ttctttttttt tggctttttta    2940 ggaccaataa tgacctctga atcttaaaat ttctttaaaa ataagccaaa attacccttt      3000
acttaattaa tttggtaacg taatataatt ggagaatttg                            3040
```

```
<210> SEQ ID NO 39
<211> LENGTH: 3047
<212> TYPE: DNA
<213> ORGANISM: Bacillus subtilis

<400> SEQUENCE: 39
gttattctgc tttcagcaca atggtttttcg cagccatatc atgaacggtt tgtttttttct      60 tcgtaaatgc ggcagtcaaa tagatcaggc gggagaacac atgcacccac gctatcaggt       120
aacggacaat ggcttgcggg aaggatattt ttttatatgt ttcgtccctc acgatttgca       180
gcccgatgat ttttttgccc agtgtgccct tccaatttgt cagcggcatc agcaaagggt       240
acacaatcag catcaatatg gcgacaataa tgacaccggc ggaccatcg ccaaacgtaa        300 atccggctgc caaaatcact gctgcggcaa tgattacatc aagtaaaaga gcgcaggcgc       360
gcagcatgaa accagctagt tccaatagaa acactcctta aaatgttaaa taaacaccta       420
atgattgtaa aaaagaaggg cctaaagtgg gaataggtga taagccttaa atcacaaaag       480
ttggtgaaaa tgtcataggt aaattggcat aatcagccag cttatcacat taccaaattc       540
ttttttagcc cgaaaccaag ccctcagaag ttattttttgt taaaatagaa aagttacaac       600
agaattcgga gggtttattg tgggaaaagt gaaacgaaat gccccttgcc catgcggcag       660
```

-continued

```
cggcaagaaa tataaaaaat gctgcggaag taaagttgtc gacttcccgg cggaactagc       720
ggcaaaagaa gcgaaacaaa ttcaggaaga cttagtggag tatgccttca cagtacatag       780
agaaagcatt tcaggcttta tcaaccagca tgattttctt tctgctatgg acagacagac       840
gaaagacatc agcgtattta acttaggaat ctggggaatc ttcttccacc cgcttgctgg       900
tgagaagaca atcttcgaag agtaccttca gaaaaaaggc gattcgatca ctcgtccgaa       960
aacgcgtgag atcgtagaat catggcgagg catgacgcct gctttattgc tgctgaagga      1020
cctgaaggaa ggcatcattc actttgaaga tgtcattacg gcaaacaat tcgaagtgga       1080 aatggacgcc agcaatcaag accttcctcc agtgggaagc ctgattcttg gatacccaat      1140
ccacgaagcg gaaaaagcag aattcttcat gcagttcacg atcttcccgg tgaagagaac      1200
agaagcgctg atcagcaagg tgaagaaata tgcggatgcc gctgtgaagg acggcaaaac      1260
gccggaggac ttcatgaagc aggaattcaa caacgttctg ttcgcgttgt tagctgagaa      1320
agatgaagag ccacaagcag agaaagcgga agtaagcact gttgagtggg caaacgactt      1380
ggagaaagaa accgctgcgg ctattgaaga aggcatgagc ggggaagagt atccgactga      1440
attgatccca gctgttattg acatctggaa aacattctgc gagaaaaaat cacctgtcat      1500
cagaaagccg gaagcttttg cggcggcagt tgaatattat gtaaacgcaa tttctcttaa      1560
cggcgcgtcc gtttcccagg ctaaactggc gaaaaaatac ggcgttagcg catcaacgat      1620
ttccagccgt tacaaagaaa ttgaaagcac gctgcaagat gaagcagatc gttttgcaca      1680
agcgttatcc tcataatgga aaaaaccttg aaaagccagg ctttttcaagg tttttttatt      1740 tctgaaacgg aattttgatt ctaaccggaa agatgggtg gcggtaggta aaatccagcc       1800
tgccaaaagc gcccttcacc agtttttgaa tgatatatgt gcccatgcct tcatgagcgc      1860 cgttttttcgt tgagcggcca aacgattgat aaattgtatc gagcacttt gggtccatcc       1920 cgggagtgct gttttcacaa gtcagtacat aaagcccgct gcgcagtgaa gtctccagtt      1980
taatctctgc ttttttctcgg gcctccgccg cgctgtcgag cgcattttct aatatgttgc      2040
cgaccaagct gacctgatca gcaggcgaaa acggaaggga agaaagcggt gtatgcatat      2100
gcagcgaaac actcacattc gaggcgcggg ctttttctaa aaaatcataa agcacccctg      2160
caacgtacgc gttctctcct ttcaaaaaac ggtcatattg gctgtattga tccgcccagt      2220
tttgaatata tgcttgtgta tctgccttgg gctgagctga tttgattgca gtgatatgtt      2280
tcattgtgtc atgattccgg cttctgacat caatcagcat ttgattggcg tgctgttcag      2340
cttgagtcag cttatcaatt tgatcagaaa gccttgcctg caaagcagac tgtccgatac      2400
ggagcccttc acacctgca aatatcgcga ttacacataa taccggcatg atgtctgtgc        2460
caatcaacac cactcccacc gacatcactt gaatcaccgc aatccacgca caaagccctg      2520
aggaacagtg tttccacacc cgcttcgtat tccaaatgta caatcctgca gcagctgcgc      2580
ctaaagcagc ggcgagccaa gaggcggctg tgctgtgtga aaaagcagca gctccctgat      2640
aacatatgaa actaaataaa atcagataaa gacattgaaa aagggtaatc acgtactaaa      2700
ctcctcaaaa atagtagttt tgaaaataat caagctgctg cttagtgatc atcgcttttt      2760
tagacgttcc ctcaaaggaa actgtgaatg aatgcttggt ataagcggaa aaatgcttta      2820
tgtaatgaat gttgataata aaggaacgat gcgaacgaag aaaatctttt tcgggcaggt      2880
cgcctttaat atcatttaat gtttgatacg tttgcacctc ttcggcggtt gtcacaatcg      2940
tcgtcgaacg tcccgtccgt tctgcgaaaa taatatcctt ctttttgcagg acgtgcattt      3000 cagacttttg ctttatcaat atacgcccat tcaaactcgt ttccgtt                      3047
```

-continued

<210> SEQ ID NO 40
<211> LENGTH: 864
<212> TYPE: DNA
<213> ORGANISM: artificial sequence
<220> FEATURE:
<223> OTHER INFORMATION: synthesized sequence

<400> SEQUENCE: 40
gtgtcaacaa catatcctat tgtcctggta cacggccttt ctggtttcga tgacatcgta        60
ggataccctt attttatgg gattgccgac gccctggaga aagatggcca caaagttttt        120
acagcctcac tctctgcatt caattccaac gaagtccgtg gcgagcaatt atgggagttc       180
gtgcaaaaga ttctcaaaga gactaaagtc aaaaaggtga atttgatcgg gcactcccaa       240
ggtcctcttg cgtgtcgtta tgtggcggcc aagcatgcta aaagtattgc aagtgttaca       300
tctgtgaatg gagtgaatca cggtagcgaa atcgccgatc ttgtcagacg gattatgaga       360
aaagattctg tccctgagta tatcgcggac gcggtaatga aggctattgg cactataatc       420
agtactttta gcggaaatag aggaaaccct caagacgcta tagcagctct ggaggcctta       480
acgacggaaa acgtgatgga atttaacaaa aaatatcctc agggactgcc agcaattcgt       540
gggggtgaag gtaaagaagt cgtgaacggc gtacactact atagctttgg ttcttacata       600
cagggtctca tcgctggcga gaagggaaac ttgctcgatc ctaccacgc cgctatgcgc        660 gttttatccg cgtttttttc agaacgtgag aacgatggtt tagtaggacg gacttcaatg       720
cggctcggca agttaattaa agacgactac gctgaggatc atttagatat ggtcaatcaa       780
gttgcggggt tagttggacg cggggaggat ataattgcta tatatacgaa tcatgccaat       840
tttttagcgt caaaaaagct ctaa                                              864

<210> SEQ ID NO 41
<211> LENGTH: 7380
<212> TYPE: DNA
<213> ORGANISM: artificial sequence
<220> FEATURE:
<223> OTHER INFORMATION: synthesized sequence

<400> SEQUENCE: 41
gcttcaaagc acccgtctcg tcaacgcctg cctcagcaac attgaatttg cagaagaaaa        60
atggcggata aagactata atatcaacag ccacttatcc ggctttatca aataagaaaa       120
agacaggcgt ttgcctgtct tttcttttat ttcttagcag ccggcatctc tttttgaagc       180
tcgtccaaaa tggcattcgc cccgtctaca ctgcggcgca gagaccacac cgcacgatcc       240
acgtggtata catgcccgtt tttcactgcc ttcagttttt tccaaaggac attctttttcg      300 atcgggcgtt taccgtcggc gtcgaggtca tctgtttttc ctgtcatcag gatgatcaca       360
tccggatctg ttttcagcag ctgctccagt gtcattttca tattcacaga gtcgccgcca       420
ttgcttgaat cgctattgcc tgacgtactg attgcatatc ggtagccgac ctgtgttaaa       480
agtctcgatg taaagaagtt ttcatccctg gccataatgg tatcatttgt atttccgatc       540
aaaagcacgg actggctgtt cgcgctgatt ttctgctttg tctcgctaag cttttcttca      600
tgcgccgtca gcttttttctc catttccttc tccttgccga ctgcttttgc aatcgtaagc      660
gaagcgtcaa ttgtatcctg ataatcagca tttaaattat taagtgcaat cgtcggcgct      720
atttttttca gctgatcgta caccttctta tgccgggtcg tgtcagcaat aattaaatcg      780
ggttttaatg aagcgatttt ttccatgctt ggctgtgagc gagtgccgac agatgtgtag      840

```
ccgtcaattt tcttcagcac atccttgttg atcagctgct tcgctttgtt gtcatcggca      900
accccgacag gcgtaatgcc gagatcaagc agtgtatcaa taaaacctag ctcaagaaca      960
acaacccgct tcggatgctc aggcacattt gtcttcccta aatcatgtgt taccgccact     1020
ttatgttctt tactgttttg attgccgctt gaagacgagc aagcagccgt taagacagaa     1080
agaagtaaaa ctgtaagaat aatcagtgtt ttttttcatat gttccagtct ctcctgttgg    1140
tagtttctat ggttaagatg tccaagagta gtataacacg gaatgagaat cattatcacc     1200
aattattttt aaaatgagaa gagaaagttc ggcttacagg aaaatcttgt ttcgcgacac     1260
agcagttcag cagctgatca tcctgtccac aaaaaagctt gcagaaaaat aacattctct     1320
gcaagctgat cctgttaaag cttcacaatc actcttcctt gaatgcgatt ttgcaaaata     1380
tcttttaacg cacccggcgt ttcttccaat gatacttccc tgtccacgat ggtcagcagc     1440
tgatcaggct tgagatcaga agacatgcgc tcccaaacag cggctctgac gtccatcgga     1500
caatatactg aatcgattcc gagcaggctt actccgcgaa gaataaaagg atacacggtt     1560
gccggaactt ctcctccgcc ggttaagccg ctcactgcga cagatccgcc gtattgaatt     1620
ttgcttaaaa gcgaggcaag ctgttttccg ccgactggat caaccgctcc ctgccattgc     1680
tgcttggaca gcgccttaag cgttccgtca tagacatctt ccctgctgat tacttcgctt     1740
gcaccaagct gtttcaaata atcagccgcc tcccggtttc cggtacttgc caccacatca     1800
taaccccgct tgttcagcat cgataccgca attccgccga caccgccggt tgctcctgtg     1860
actagcacgc tgcctttttc cggagacaga ccgttctgtt caagccgatg cactgataac     1920
gccgcagtaa atcccgccgt tccgtacacc atcgcttctt ttaacgaaag attctgtggc     1980
aaaggcacca gccagtcacc aggcaccgaa gcgtattcac ttaatccgcc atcacgtgag     2040
acaccgagct catagcttgt cgcgatcacc tcatccccct ccgcaaaacg cggatcattg     2100
gaagagacga ccgtacccgc agcatcaatg cctaaaataa gcggatactc tctgacgata     2160
ttgcctcctg ctttttccggc cagaccatct ttgtaattaa tgccggaata agcaacttta     2220
atcaggacac catccttcgg caaatcctct gttgatatgg ttttcacatg gactgaaaca     2280
tcatcggcat ttttttctgc ctgcaaggct tgaaataacg ttgacattcg gcacactcct     2340
tttcatttat atcgtaaccg aagaacgttc aaaaaaccaa atcatcaagc cgccatttttc    2400 acttcgccgg cacattgaga caataatgga caaatccggt atcctcttca tagccgtttt     2460
gctcatacaa gcttcttgcc ttccggttgt ggtgctcagt ctgaagtgtt aaacattttg     2520
ccccgttttg ccctgcataa tcctttgcgg cagaaagcag ccggccgccg gctccctttg     2580
tacgcgcatg aggaacgaca aataagtcat ttaatatgta tatccttttc attgacacag     2640 aagaaacgt tggatagagc tgggtaaagc ctatgaattc tccattttct tctgctatca      2700
aaataacaga ctcgtgattt tccaaacgag ctttcaaaaa agcctctgcc ccttgcaaat     2760
cggatgcctg tctataaaat tcccgatatt ggttaaacag cggcgcaatg gcggccgcat     2820
ctgatgtctt tgcttggcga atgttcatct tatttcttcc tccctctcaa taattttttc     2880
attctatccc ttttctgtaa agtttatttt tcagaatact tttatcatca tgctttgaaa     2940
aaatatcacg ataatatcca ttgttctcac ggaagcacac gcgtcgctga taaacagctg     3000
acatcaatat cctatttttt caaaaaatat tttaaaagtt gttgacttaa aagaagctaa     3060
atgttatagt aataaaacag aatagtcttt taagtaagtc tactctgaat ttttttaaaa     3120
ggagagggta aagaaagccg ccaggaaaaa cttgtctgaa tagtacggtt gcaatttttta    3180 ggggaaacag atatacttaa gtgtacagaa tagtctttta agtaagtcta ctctgaattt     3240
```

```
ttttaaaagg agagggtaaa gagtgtcaac aacatatcct attgtcctgg tacacggcct    3300
ttctggtttc gatgacatcg taggataccc ttattttat gggattgccg acgccctgga     3360
gaaagatggc cacaaagttt ttacagcctc actctctgca ttcaattcca acgaagtccg    3420
tggcgagcaa ttatgggagt tcgtgcaaaa gattctcaaa gagactaaag tcaaaaaggt    3480
gaatttgatc gggcacgcgc aaggtcctct tgcgtgtcgt tatgtggcgg ccaagcatgc    3540
taaaagtatt gcaagtgtta catctgtgaa tggagtgaat cacggtagcg aaatcgccga    3600
tcttgtcaga cggattatga gaaaagattc tgtccctgag tatatcgcgg acgcggtaat    3660
gaaggctatt ggcactataa tcagtacttt tagcggaaat agaggaaacc ctcaagacgc    3720
tatagcagct ctggaggcct taacgacgga aaacgtgatg gaatttaaca aaaaatatcc    3780
tcagggactg ccagcaattc gtgggggtga aggtaaagaa gtcgtgaacg gcgtacacta    3840
ctatagcttt ggttcttaca tacagggtct catcgctggc gagaagggaa acttgctcga    3900
tcctacccac gccgctatgc gcgtttttatc cgcgttttttt tcagaacgtg agaacgatgg   3960
tttagtagga cggacttcaa tgcggctcgg caagttaatt aaagacgact acgctgagga    4020
tcatttagat atggtcaatc aagttgcggg gttagttgga cgcggggagg atataattgc    4080
tatatatacg aatcatgcca attttttagc gtcaaaaaag ctctaatcta gatacataaa    4140
aaaccggcct tggccccgcc ggttttttat tattttttctt cctccgcatg ttcaatccgc    4200
tccataatcg acggatggct ccctctgaaa attttaacga gaaacggcgg gttgacccgg    4260
ctcagtcccg taacggccaa gtcctgaaac gtctcaatcg ccgcttcccg gtttccggtc    4320
agctcaatgc cgtaacggtc ggcggcgttt tcctgatacc gggagacggc attcgtaatc    4380
aacgcctcac tcctcacatc aacccgttac ttctattgta atcataaatt caaattctta    4440
gaaccaagct gtgttccgca cttttccacc cttttaagca tggaaacccc gatcgctggg    4500
aaaactaaca atgtttggag tgatgcaaat gaaaaaaata gtggcagcca tcgtggtaat    4560
cggtcttgtg tttatcgcat ttttttatct ttacagccga tcaggcgatg tgtatcaatc    4620
ggtagacgcg gatttgatca cactgtcttc aagcggccag gaagatatcg agattgaaaa    4680
aagacagcac gtcaaagata tgctggatat tatgaatcag ggaaaacagg tgaagacaga    4740
aaaaacatca gccctgatt acgaagggac aatcaagttt cataaagacc ggtatgactc     4800
attcagacta tggattgacg gcagccagca agccgttttt ttgaaggatg gcacatacta    4860
caaattaagc aaaaatgata caaaggcgct gctaaatatt attaaaaaag aagcaaagga    4920
ttgaaaatga aaaagcgaag ctaaccgctt cgctttttca ttttattggg gcaaaatatc    4980
tctcagtgcc cgtctgagca ttttccccgt cgcattttttc ggaatatcgt caagaaacgt    5040
aatggcggca ggccgcttgt attttgccag atgcttttcg cagtgctgca tgatgtcctc    5100
ctctgttacc ccagagcgtt tcggcaccac atatcccttt accgcttccc cgctttgggg    5160
gtccggcacg ccgatgacaa ccgcctcctt gacgtccgga tggctgtaca gcacctcctc    5220
cacctcccgc ggatacacat tgtatcctcc tacaatgatc atgtcttttt tccggtcaac    5280
aatgtaaaaa tagccgtcct catcccgtct tgccaagtcc cccgtataaa gccaccgtc     5340 ttttaatgca tgctctgttt ccatcggcat tttataatag cccttcatca cattggggcc    5400
tttcacgatc aattcgccga cctggtgagc gggcagctcg cgtccgagcg gatctacgac    5460
cttgttttcg acatgtaaga tacttgtccc gatggagccc ggctttctgc ccctgtcaaa    5520
cgggttaaag cacgtgacgg gtgatgcttc cgagagcccg tagccttcca aaatggtaac    5580
```

```
accgaatttt tcttcaaacg ccgtcagcaa cgcgactggc atggacgcgc ctcccgaaat      5640
gcacagccgg atcgaagaaa aatcatcttt ctttccgttt tcatgctgaa acaagtagtt      5700
atacattgta ggcacaccgg caaaaatggt cgcctgctgc tgcttaacaa gcttaaaaac      5760
agatgccgga ctgaattgag gctcaatcaa tacagttgcg ccgctcatca gcggtgcatt      5820
catacagacg gttaaacaaa acacgtgaaa catgggaaga gcgcagacca cattgtccct      5880
ctcatccatt cccaaatagc ctgcgacatc gttggcattg ctgtacaaat tctgatgtgt      5940
cagcatcgcg cctttcggtt ttccagtcgt tcctgacgta tataaaataa ccgcggtatc      6000
atcaggtaca ggttcttggt tttgtttagc ggcagatgtc ggccgcaata tttttgcaaa      6060
cgttgtcatt ttcatcctga cctctgggtc cgcagcttcc ggctcggcct cccccgtctg      6120
gcataaaatg acgagctcaa cctttggcag cgattcatgc atgctctcat aaagcggcaa      6180
aagctggcta acgcccacga ttgcctttac atcgccattt gtcagcatat aaccaatttc      6240
tgtcggcgtg tacaacggat tgatgggaac aactacgatc ccagctttta aagcgccaaa      6300
aaacgcgatg ataaaatcag gcgaattgcc aagcagcaaa gctaaatggt cccctttctc      6360
cataccggct tcctgaaggc cgtccgcaaa tcgctgaata tattcattca gctcttgata      6420
cgtcatcatg tgatctttaa acctgcatgc gatgctgtcg ggcttctcag atgctgtttc      6480
ttccaatttt gaaacaagat tcattctccc accccttaag tgaatgaata gtcattcatt      6540
attgaagcca agctttcttc tccattatag agaaacagaa aaaaacactc aagagcaaaa      6600
agccctgagt gtcagtactg tcatagtttc ttcaatgctt cggcaatcgg cgtatctcct      6660
tctgtcagat caaaggcccg attttccgta ttcttctcat ctaaagaggc aatgaccgtt      6720
tttgcaacgt catcacggga aataaatccc cgctccagat ccttcgctgc tgaaacagtt      6780
cccgttccag gctcattgcg aaggcctccc ggacggataa tcgtataggt taaaccgctc      6840
gcttccagaa ttttatcagc ataatgcttg gccacataat aaggcttgag tgcctcattc      6900
caattttcac ggttatgggc ttgcaggcg ctgaccataa taaaccgttt gattccggca      6960
atggccgcag cttcaatggc ttttgccgct ccatcaagat ccaccagcag cgttttatca      7020
tagcctgtgc tgccgccgga accggctgtg aaaatgatcg cgtcacaacc ttttgccgca      7080
gcggcgattt cttccgggct gccctccaga ttcgcaagca cagcttctgc accggcagct      7140
tcaagagacg ctttctgttc ttcttttctg accatcgctc tgatggaatg atcaggatta      7200
tcttggaata aagagacgag tctttgcccg atttgtccgt tcgctccgat taaaaacact      7260
ttcatgtgaa tccctcctgc ctccattatt tcaaaaacac aaccgctctt tcaaacgatg      7320
tgttttgcct tagtaaatca gatcaaggaa atcctctttc gtaatgttcc caaagtaatg      7380
```

<210> SEQ ID NO 42
<211> LENGTH: 94
<212> TYPE: DNA
<213> ORGANISM: artificial sequence
<220> FEATURE:
<223> OTHER INFORMATION: synthesized sequence

<400> SEQUENCE: 42

```
gtcgctgata aacagctgac atcaatatcc tatttttca aaaatattt taaaagttgt         60 tgacttaaaa gaagctaaat gttatagtaa taaa                                    94
```

<210> SEQ ID NO 43
<211> LENGTH: 39
<212> TYPE: DNA
<213> ORGANISM: artificial sequence

```
<220> FEATURE:
<223> OTHER INFORMATION: synthesized sequence

<400> SEQUENCE: 43
cacgcaagag gaccttgcgc gtgcccgatc aaattcacc                          39

<210> SEQ ID NO 44
<211> LENGTH: 3516
<212> TYPE: DNA
<213> ORGANISM: artificial sequence
<220> FEATURE:
<223> OTHER INFORMATION: synthesized sequence

<400> SEQUENCE: 44
gcttcaaagc acccgtctcg tcaacgcctg cctcagcaac attgaatttg cagaagaaaa     60
atggcggata aaagactata atatcaacag ccacttatcc ggctttatca aataagaaaa    120
agacaggcgt ttgcctgtct tttcttttat ttcttagcag ccggcatctc tttttgaagc    180
tcgtccaaaa tggcattcgc cccgtctaca ctgcggcgca gagaccacac cgcacgatcc    240
acgtggtata catgcccgtt tttcactgcc ttcagttttt tccaaaggac attctttttcg    300 atcgggcgtt taccgtcggc gtcgaggtca tctgtttttc ctgtcatcag gatgatcaca    360
tccggatctg ttttcagcag ctgctccagt gtcattttca tattcacaga gtcgccgcca    420
ttgcttgaat cgctattgcc tgacgtactg attgcatatc ggtagccgac ctgtgttaaa    480
agtctcgatg taaagaagtt ttcatccctg gccataatgg tatcatttgt atttccgatc    540
aaaagcacgg actggctgtt cgcgctgatt ttctgctttg tctcgctaag cttttcttca    600
tgcgccgtca gctttttctc catttccttc tccttgccga ctgcttttgc aatcgtaagc    660
gaagcgtcaa ttgtatcctg ataatcagca tttaaattat taagtgcaat cgtcggcgct    720 attttttttca gctgatcgta caccttctta tgccgggtcg tgtcagcaat aattaaatcg    780
ggttttaatg aagcgatttt ttccatgctt ggctgtgagc gagtgccgac agatgtgtag    840
ccgtcaattt tcttcagcac atccttgttg atcagctgct tcgctttgtt gtcatcggca    900
accccgacag gcgtaatgcc gagatcaagc agtgtatcaa taaaacctag ctcaagaaca    960
acaacccgct tcggatgctc aggcacattt gtcttcccta aatcatgtgt taccgccact   1020
ttatgttctt tactgttttg attgccgctt gaagacgagc aagcagccgt taagacagaa   1080
agaagtaaaa ctgtaagaat aatcagtgtt tttttcatat gttccagtct ctcctgttgg   1140
tagtttctat ggttaagatg tccaagagta gtataacacg gaatgagaat cattatcacc   1200
aattattttt aaaatgagaa gagaaagttc ggcttacagg aaaatcttgt ttcgcgacac   1260
agcagttcag cagctgatca tcctgtccac aaaaaagctt gcagaaaaat aacattctct   1320
gcaagctgat cctgttaaag cttcacaatc actcttcctt gaatgcgatt ttgcaaaata   1380
tcttttaacg cacccggcgt ttcttccaat gatacttccc tgtccacgat ggtcagcagc   1440
tgatcaggct tgagatcaga agacatgcgc tcccaaacag cggctctgac gtccatcgga   1500
caatatactg aatcgattcc gagcaggctt actccgcgaa gaataaaagg atacacggtt   1560
gccggaactt ctcctccgcc ggttaagccg ctcactgcga cagatccgcc gtattgaatt   1620
ttgcttaaaa gcgaggcaag ctgttttccg ccgactggat caaccgctcc ctgccattgc   1680
tgcttggaca gcgccttaag cgttccgtca tagacatctt ccctgctgat tacttcgctt   1740
gcaccaagct gtttcaaata atcagccgcc tcccggtttc cggtacttgc caccacatca   1800
taaccccgct tgttcagcat cgataccgca attccgcga caccgccggt tgctcctgtg   1860
```

-continued

```
actagcacgc tgcctttttc cggagacaga ccgttctgtt caagccgatg cactgataac      1920
gccgcagtaa atcccgccgt tccgtacacc atcgcttctt ttaacgaaag attctgtggc      1980
aaaggcacca gccagtcacc aggcaccgaa gcgtattcac ttaatccgcc atcacgtgag      2040
acaccgagct catagcttgt cgcgatcacc tcatccccct ccgcaaaacg cggatcattg      2100
gaagagacga ccgtacccgc agcatcaatg cctaaaataa gcggatactc tctgacgata      2160
ttgcctcctg cttttccggc cagaccatct ttgtaattaa tgccggaata agcaacttta      2220
atcaggacac catccttcgg caaatcctct gttgatatgg ttttcacatg gactgaaaca      2280
tcatcggcat ttttttctgc ctgcaaggct tgaaataacg ttgacattcg gcacactcct      2340
tttcatttat atcgtaaccg aagaacgttc aaaaaaccaa atcatcaagc cgccattttc      2400
acttcgccgg cacattgaga caataatgga caaatccggt atcctcttca tagccgtttt      2460
gctcatacaa gcttcttgcc ttccggttgt ggtgctcagt ctgaagtgtt aaacattttg      2520
ccccgttttg ccctgcataa tcctttgcgg cagaaagcag ccggccgccg gctccctttg      2580
tacgcgcatg aggaacgaca aataagtcat ttaatatgta tatccttttc attgacacag      2640 aagaaacgt tggatagagc tgggtaaagc ctatgaattc tccattttct tctgctatca      2700
aaataacaga ctcgtgattt tccaaacgag cttttcaaaaa agcctctgcc ccttgcaaat      2760
cggatgcctg tctataaaat tcccgatatt ggttaaacag cggcgcaatg gcggccgcat      2820
ctgatgtctt tgcttggcga atgttcatct tatttcttcc tccctctcaa taattttttc      2880
attctatccc ttttctgtaa agtttatttt tcagaatact tttatcatca tgctttgaaa      2940
aaatatcacg ataatatcca ttgttctcac ggaagcacac gcgtcgctga taaacagctg      3000
acatcaatat cctattttttt caaaaaatat tttaaaagtt gttgacttaa aagaagctaa      3060
atgttatagt aataaaacag aatagtcttt taagtaagtc tactctgaat ttttttaaaa      3120
ggagagggta aagaaagccg ccaggaaaaa cttgtctgaa tagtacggtt gcaattttta      3180
ggggaaacag atatacttaa gtgtacagaa tagtctttta agtaagtcta ctctgaattt      3240
ttttaaaagg agagggtaaa gagtgtcaac aacatatcct attgtcctgg tacacggcct      3300
ttctggtttc gatgacatcg taggataccc ttattttttat gggattgccg acgccctgga      3360
gaaagatggc cacaaagttt ttacagcctc actctctgca ttcaattcca acgaagtccg      3420
tggcgagcaa ttatgggagt tcgtgcaaaa gattctcaaa gagactaaag tcaaaaaggt      3480
gaatttgatc gggcacgcgc aaggtcctct tgcgtg                                3516
```

```
<210> SEQ ID NO 45
<211> LENGTH: 39
<212> TYPE: DNA
<213> ORGANISM: artificial sequence
<220> FEATURE:
<223> OTHER INFORMATION: synthesized sequence

<400> SEQUENCE: 45
ggtgaatttg atcgggcacg cgcaaggtcc tcttgcgtg                               39

<210> SEQ ID NO 46
<211> LENGTH: 28
<212> TYPE: DNA
<213> ORGANISM: artificial sequence
<220> FEATURE:
<223> OTHER INFORMATION: synthesized sequence

<400> SEQUENCE: 46
cattactttg ggaacattac gaaagagg                                           28
```

<210> SEQ ID NO 47
<211> LENGTH: 3903
<212> TYPE: DNA
<213> ORGANISM: artificial sequence
<220> FEATURE:
<223> OTHER INFORMATION: synthesized sequence

<400> SEQUENCE: 47

```
ggtgaatttg atcgggcacg cgcaaggtcc tcttgcgtgt cgttatgtgg cggccaagca      60
tgctaaaagt attgcaagtg ttacatctgt gaatggagtg aatcacggta gcgaaatcgc     120
cgatcttgtc agacggatta tgagaaaaga ttctgtccct gagtatatcg cggacgcggt     180
aatgaaggct attggcacta taatcagtac ttttagcgga aatagaggaa accctcaaga     240
cgctatagca gctctggagg ccttaacgac ggaaaacgtg atggaattta acaaaaaata     300
tcctcaggga ctgccagcaa ttcgtggggg tgaaggtaaa gaagtcgtga acggcgtaca     360
ctactatagc tttggttctt acatacaggg tctcatcgct ggcgagaagg gaaacttgct     420
cgatcctacc cacgccgcta tgcgcgtttt atccgcgttt ttttcagaac gtgagaacga     480
tggtttagta ggacggactt caatgcggct cggcaagtta attaaagacg actacgctga     540
ggatcattta gatatggtca atcaagttgc ggggttagtt ggacgcgggg aggatataat     600
tgctatatat acgaatcatg ccaatttttt agcgtcaaaa aagctctaat ctagatacat     660
aaaaaaccgg ccttggcccc gccggttttt tattattttt cttcctccgc atgttcaatc     720
cgctccataa tcgacggatg gctccctctg aaaattttaa cgagaaacgg cgggttgacc     780
cggctcagtc ccgtaacggc caagtcctga aacgtctcaa tcgccgcttc ccggtttccg     840
gtcagctcaa tgccgtaacg gtcggcggcg ttttcctgat accgggagac ggcattcgta     900
atcaacgcct cactcctcac atcaacccgt tacttctatt gtaatcataa attcaaattc     960
ttagaaccaa gctgtgttcc gcactttttc cccttttaa gcatggaaac cccgatcgct    1020
gggaaaacta acaatgtttg gagtgatgca aatgaaaaaa atagtggcag ccatcgtggt    1080
aatcggtctt gtgtttatcg catttttta tctttacagc cgatcaggcg atgtgtatca    1140
atcggtagac gcggatttga tcacactgtc ttcaagcggc caggaagata tcgagattga    1200
aaaaagacag cacgtcaaag atatgctgga tattatgaat cagggaaaac aggtgaagac    1260
agaaaaaaca tcagcccctg attacgaagg gacaatcaag tttcataaag accggtatga    1320
ctcattcaga ctatggattg acggcagcca gcaagccgtt tttttgaagg atggcacata    1380
ctacaaatta agcaaaaatg atacaaaggc gctgctaaat attattaaaa aagaagcaaa    1440
ggattgaaaa tgaaaaagcg aagctaaccg cttcgctttt tcattttatt ggggcaaaat    1500
atctctcagt gcccgtctga gcattttccc cgtcgcattt ttcggaatat cgtcaagaaa    1560
cgtaatggcg gcaggccgct tgtattttgc cagatgcttt tcgcagtgct gcatgatgtc    1620
ctcctctgtt accccagagc gtttcggcac cacatatccc tttaccgctt ccccgctttg    1680
ggggtccggc acgccgatga caaccgcctc cttgacgtcc ggatggctgt acagcacctc    1740
ctccacctcc cgcggataca cattgtatcc tcctacaatg atcatgtctt ttttccggtc    1800
aacaatgtaa aaatagccgt cctcatcccg tcttgccaag tccccgtat aaagccaccc     1860 gtcttttaat gcatgctctg tttccatcgg cattttataa tagcccttca tcacattggg    1920
gcctttcacg atcaattcgc cgacctggtg agcgggcagc tcgcgtccga gcggatctac    1980
gaccttgttt tcgacatgta agatacttgt cccgatggag cccggctttc tgcccctgtc    2040
```

-continued

```
aaacgggtta aagcacgtga cgggtgatgc ttccgagagc ccgtagcctt ccaaaatggt     2100
aacaccgaat ttttcttcaa acgccgtcag caacgcgact ggcatggacg cgcctcccga     2160
aatgcacagc cggatcgaag aaaaatcatc tttctttccg ttttcatgct gaaacaagta     2220
gttatacatt gtaggcacac cggcaaaaat ggtcgcctgc tgctgcttaa caagcttaaa     2280
aacagatgcc ggactgaatt gaggctcaat caatacagtt gcgccgctca tcagcggtgc     2340
attcatacag acggttaaac aaaacacgtg aaacatggga agagcgcaga ccacattgtc     2400
cctctcatcc attcccaaat agcctgcgac atcgttggca ttgctgtaca aattctgatg     2460
tgtcagcatc gcgcctttcg gttttccagt cgttcctgac gtatataaaa taaccgcggt     2520
atcatcaggt acaggttctt ggttttgttt agcggcagat gtcggccgca atattttttgc     2580 aaacgttgtc attttcatcc tgacctctgg gtccgcagct tccggctcgg cctcccccgt     2640
ctggcataaa atgacgagct caacctttgg cagcgattca tgcatgctct cataaagcgg     2700
caaaagctgg ctaacgccca cgattgcctt tacatcgcca tttgtcagca tataaccaat     2760
ttctgtcggc gtgtacaacg gattgatggg aacaactacg atcccagctt ttaaagcgcc     2820
aaaaaacgcg atgataaaat caggcgaatt gccaagcagc aaagctaaat ggtccccttt     2880
ctccataccg gcttcctgaa ggccgtccgc aaatcgctga atatattcat tcagctcttg     2940
atacgtcatc atgtgatctt taaacctgca tgcgatgctg tcgggcttct cagatgctgt     3000
ttcttccaat tttgaaacaa gattcattct cccacccctt aagtgaatga atagtcattc     3060
attattgaag ccaagctttc ttctccatta tagagaaaca gaaaaaaaca ctcaagagca     3120
aaaagccctg agtgtcagta ctgtcatagt ttcttcaatg cttcggcaat cggcgtatct     3180
ccttctgtca gatcaaaggc ccgattttcc gtattcttct catctaaaga ggcaatgacc     3240
gtttttgcaa cgtcatcacg ggaaataaat ccccgctcca gatccttcgc tgctgaaaca     3300
gttcccgttc caggctcatt gcgaaggcct cccggacgga taatcgtata ggttaaaccg     3360
ctcgcttcca gaattttatc agcataatgc ttggccacat aataaggctt gagtgcctca     3420
ttccaatttt cacggttatg ggcttgcagg gcgctgacca taataaaccg tttgattccg     3480
gcaatggccg cagcttcaat ggcttttgcc gctccatcaa gatccaccag cagcgtttta     3540
tcatagcctg tgctgccgcc ggaaccggct gtgaaaatga tcgcgtcaca accttttgcc     3600
gcagcggcga tttcttccgg gctgccctcc agattcgcaa gcacagcttc tgcaccggca     3660
gcttcaagag acgctttctg ttcttctttt ctgaccatcg ctctgatgga atgatcagga     3720
ttatcttgga ataaagagac gagtctttgc ccgatttgtc cgttcgctcc gattaaaaac     3780
actttcatgt gaatccctcc tgcctccatt atttcaaaaa cacaaccgct ctttcaaacg     3840
atgtgttttg ccttagtaaa tcagatcaag gaaatcctct ttcgtaatgt tcccaaagta     3900
atg                                                                                                              3903
```

```
<210> SEQ ID NO 48
<211> LENGTH: 7334
<212> TYPE: DNA
<213> ORGANISM: artificial sequence
<220> FEATURE:
<223> OTHER INFORMATION: synthesized sequence

<400> SEQUENCE: 48
tcgtcaacgc ctgcctcagc aacattgaat ttgcagaaga aaaatggcgg ataaaagact       60
ataatatcaa cagccactta tccggcttta tcaaataaga aaaagacagg cgtttgcctg      120
tcttttcttt tatttcttag cagccggcat ctcttttttga agctcgtcca aaatggcatt      180
```

```
cgccccgtct acactgcggc gcagagacca caccgcacga tccacgtggt atacatgccc     240
gtttttcact gccttcagtt ttttccaaag gacattcttt tcgatcgggc gtttaccgtc     300
ggcgtcgagg tcatctgttt ttcctgtcat caggatgatc acatccggat ctgttttcag     360
cagctgctcc agtgtcattt tcatattcac agagtcgccg ccattgcttg aatcgctatt     420
gcctgacgta ctgattgcat atcggtagcc gacctgtgtt aaaagtctcg atgtaaagaa     480
gttttcatcc ctggccataa tggtatcatt tgtatttccg atcaaaagca cggactggct     540
gttcgcgctg attttctgct ttgtctcgct aagctttct tcatgcgccg tcagcttttt      600
ctccatttcc ttctccttgc cgactgcttt tgcaatcgta agcgaagcgt caattgtatc     660
ctgataatca gcatttaaat tattaagtgc aatcgtcggc gctatttttt tcagctgatc     720
gtacaccttc ttatgccggg tcgtgtcagc aataattaaa tcgggtttta atgaagcgat     780
tttttccatg cttggctgtg agcgagtgcc gacagatgtg tagccgtcaa ttttcttcag     840
cacatccttg ttgatcagct gcttcgcttt gttgtcatcg gcaaccccga caggcgtaat     900
gccgagatca agcagtgtat caataaaacc tagctcaaga acaacaaccc gcttcggatg     960
ctcaggcaca tttgtcttcc ctaaatcatg tgttaccgcc actttatgtt ctttactgtt    1020
ttgattgccg cttgaagacg agcaagcagc cgttaagaca gaaagaagta aaactgtaag    1080
aataatcagt gtttttttca tatgttccag tctctcctgt tggtagtttc tatggttaag    1140
atgtccaaga gtagtataac acggaatgag aatcattatc accaattatt tttaaaatga    1200
gaagagaaag ttcggcttac aggaaaatct tgtttcgcga cacagcagtt cagcagctga    1260
tcatcctgtc cacaaaaaag cttgcagaaa aataacattc tctgcaagct gatcctgtta    1320
aagcttcaca atcactcttc cttgaatgcg attttgcaaa atatctttta acgcacccgg    1380
cgtttcttcc aatgatactt ccctgtccac gatggtcagc agctgatcag gcttgagatc    1440
agaagacatg cgctcccaaa cagcggctct gacgtccatc ggacaatata ctgaatcgat    1500
tccgagcagg cttactccgc gaagaataaa aggatacacg gttgccggaa cttctcctcc    1560
gccggttaag ccgctcactg cgacagatcc gccgtattga attttgctta aaagcgaggc    1620
aagctgtttt ccgccgactg gatcaaccgc tccctgccat tgctgcttgg acagcgcctt    1680
aagcgttccg tcatagacat cttccctgct gattacttcg cttgcaccaa gctgtttcaa    1740
ataatcagcc gcctcccggt ttccggtact tgccaccaca tcataacccc gcttgttcag    1800
catcgatacc gcaattccgc cgacaccgcc ggttgctcct gtgactagca cgctgccttt    1860
ttccggagac agaccgttct gttcaagccg atgcactgat aacgccgcag taaatcccgc    1920
cgttccgtac accatcgctt cttttaacga aagattctgt ggcaaaggca ccagccagtc    1980
accaggcacc gaagcgtatt cacttaatcc gccatcacgt gagacaccga gctcatagct    2040
tgtcgcgatc acctcatccc cctccgcaaa acgcggatca ttggaagaga cgaccgtacc    2100
cgcagcatca atgcctaaaa taagcggata ctctctgacg atattgcctc ctgcttttcc    2160
ggccagacca tctttgtaat taatgccgga ataagcaact ttaatcagga caccatcctt    2220
cggcaaatcc tctgttgata tggttttcac atggactgaa acatcatcgg catttttttc    2280
tgcctgcaag gcttgaaata acgttgacat tcggcacact ccttttcatt tatatcgtaa    2340
ccgaagaacg ttcaaaaaac caaatcatca agccgccatt ttcacttcgc cggcacattg    2400
agacaataat ggacaaatcc ggtatcctct tcatagccgt tttgctcata caagcttctt    2460
gccttccggt tgtggtgctc agtctgaagt gttaaacatt ttgccccgtt ttgccctgca    2520
```

-continued

```
taatcctttg cggcagaaag cagccggccg ccggctccct ttgtacgcgc atgaggaacg   2580
acaaataagt catttaatat gtatatcctt ttcattgaca cagaagaaaa cgttggatag   2640
agctgggtaa agcctatgaa ttctccattt tcttctgcta tcaaaataac agactcgtga   2700
ttttccaaac gagctttcaa aaaagcctct gccccttgca aatcggatgc ctgtctataa   2760
aattcccgat attggttaaa cagcggcgca atggcggccg catctgatgt ctttgcttgg   2820
cgaatgttca tcttatttct tcctccctct caataatttt ttcattctat ccctttctg    2880 taaagtttat ttttcagaat acttttatca tcatgctttg aaaaaatatc acgataatat   2940
ccattgttct cacggaagca cacgcgtcgc tgataaacag ctgacatcaa tatcctattt   3000
tttcaaaaaa tattttaaaa gttgttgact aaaagaagc taaatgttat agtaataaaa    3060
cagaatagtc ttttaagtaa gtctactctg aattttttta aaaggagagg gtaaagaaag   3120
ccgccaggaa aaacttgtct gaatagtacg gttgcaattt ttaggggaaa cagatatact   3180
taagtgtaca gaatagtctt ttaagtaagt ctactctgaa tttttttaaa aggagagggt   3240
aaagagtgtc aacaacatat cctattgtcc tggtacacgg cctttctggt ttcgatgaca   3300
tcgtaggata cccttatttt tatgggattg ccgacgccct ggagaaagat ggccacaaag   3360
tttttacagc ctcactctct gcattcaatt ccaacgaagt ccgtggcgag caattatggg   3420
agttcgtgca aaagattctc aaagagacta aagtcaaaaa ggtgaatttg atcgggcacg   3480
cgcaaggtcc tcttgcgtgt cgttatgtgg cggccaagca tgctaaaagt attgcaagtg   3540
ttacatctgt gaatggagtg aatcacggta gcgaaatcgc cgatcttgtc agacggatta   3600
tgagaaaaga ttctgtccct gagtatatcg cggacgcggt aatgaaggct attggcacta   3660
taatcagtac ttttagcgga aatagaggaa accctcaaga cgctatagca gctctggagg   3720
ccttaacgac ggaaaacgtg atggaattta acaaaaaata tcctcaggga ctgccagcaa   3780
ttcgtggggg tgaaggtaaa gaagtcgtga acggcgtaca ctactatagc tttggttctt   3840
acatacaggg tctcatcgct ggcgagaagg gaaacttgct cgatcctacc cacgccgcta   3900
tgcgcgtttt atccgcgttt ttttcagaac gtgagaacga tggtttagta ggacggactt   3960
caatgcggct cggcaagtta attaaagacg actacgctga ggatcattta gatatggtca   4020
atcaagttgc ggggttagtt ggacgcgggg aggatataat tgctatatat acgaatcatg   4080
ccaatttttt agcgtcaaaa aagctctaat ctagatacat aaaaaaccgg ccttggcccc   4140
gccggttttt tattattttt cttcctccgc atgttcaatc cgctccataa tcgacggatg   4200
gctccctctg aaaattttaa cgagaaacgg cgggttgacc cggctcagtc ccgtaacggc   4260
caagtcctga aacgtctcaa tcgccgcttc ccggtttccg gtcagctcaa tgccgtaacg   4320
gtcggcggcg ttttcctgat accgggagac ggcattcgta atcaacgcct cactcctcac   4380
atcaacccgt tacttctatt gtaatcataa attcaaattc ttagaaccaa gctgtgttcc   4440
gcacttttcc acccttttaa gcatggaaac cccgatcgct gggaaaacta acaatgtttg   4500
gagtgatgca aatgaaaaaa atagtggcag ccatcgtggt aatcggtctt gtgtttatcg   4560
cattttttta tctttacagc cgatcaggcg atgtgtatca atcggtagac gcggatttga   4620
tcacactgtc ttcaagcggc caggaagata tcgagattga aaaagacag cacgtcaaag    4680 atatgctgga tattatgaat cagggaaaac aggtgaagac agaaaaaaca tcagcccctg   4740
attacgaagg gacaatcaag tttcataaag accggtatga ctcattcaga ctatggattg   4800
acggcagcca gcaagccgtt tttttgaagg atggcacata ctacaaatta agcaaaaatg   4860
atacaaaggc gctgctaaat attattaaaa aagaagcaaa ggattgaaaa tgaaaaagcg   4920
```

```
aagctaaccg cttcgctttt tcattttatt ggggcaaaat atctctcagt gcccgtctga   4980
gcattttccc cgtcgcattt ttcggaatat cgtcaagaaa cgtaatggcg gcaggccgct   5040
tgtattttgc cagatgcttt tcgcagtgct gcatgatgtc ctcctctgtt accccagagc   5100
gtttcggcac cacatatccc tttaccgctt ccccgctttg ggggtccggc acgccgatga   5160
caaccgcctc cttgacgtcc ggatggctgt acagcacctc ctccacctcc cgcggataca   5220
cattgtatcc tcctacaatg atcatgtctt ttttccggtc aacaatgtaa aaatagccgt   5280
cctcatcccg tcttgccaag tcccccgtat aaagccaccc gtcttttaat gcatgctctg   5340
tttccatcgg cattttataa tagcccttca tcacattggg gcctttcacg atcaattcgc   5400
cgacctggtg agcgggcagc tcgcgtccga gcggatctac gaccttgttt tcgacatgta   5460
agatacttgt cccgatggag cccggctttc tgcccctgtc aaacgggtta aagcacgtga   5520
cgggtgatgc ttccgagagc ccgtagcctt ccaaaatggt aacaccgaat ttttcttcaa   5580
acgccgtcag caacgcgact ggcatggacg cgcctcccga aatgcacagc cggatcgaag   5640
aaaaatcatc tttctttccg ttttcatgct gaaacaagta gttatacatt gtaggcacac   5700
cggcaaaaat ggtcgcctgc tgctgcttaa caagcttaaa aacagatgcc ggactgaatt   5760
gaggctcaat caatacagtt gcgccgctca tcagcggtgc attcatacag acggttaaac   5820
aaaacacgtg aaacatggga agagcgcaga ccacattgtc cctctcatcc attcccaaat   5880
agcctgcgac atcgttggca ttgctgtaca aattctgatg tgtcagcatc gcgcctttcg   5940
gttttccagt cgttcctgac gtatataaaa taaccgcggt atcatcaggt acaggttctt   6000
ggttttgttt agcggcagat gtcggccgca atattttgc aaacgttgtc attttcatcc   6060
tgacctctgg gtccgcagct tccggctcgg cctcccccgt ctggcataaa atgacgagct   6120
caacctttgg cagcgattca tgcatgctct cataaagcgg caaaagctgg ctaacgccca   6180
cgattgcctt tacatcgcca tttgtcagca tataaccaat ttctgtcggc gtgtacaacg   6240
gattgatggg aacaactacg atcccagctt ttaaagcgcc aaaaaacgcg atgataaaat   6300
caggcgaatt gccaagcagc aaagctaaat ggtccccttt ctccataccg gcttcctgaa   6360
ggccgtccgc aaatcgctga atatattcat tcagctcttg atacgtcatc atgtgatctt   6420
taaacctgca tgcgatgctg tcgggcttct cagatgctgt ttcttccaat tttgaaacaa   6480
gattcattct cccaccccctt aagtgaatga atagtcattc attattgaag ccaagctttc   6540
ttctccatta tagagaaaca gaaaaaaaca ctcaagagca aaaagccctg agtgtcagta   6600
ctgtcatagt ttcttcaatg cttcggcaat cggcgtatct ccttctgtca gatcaaaggc   6660
ccgattttcc gtattcttct catctaaaga ggcaatgacc gttttgcaa cgtcatcacg   6720 ggaaataaat ccccgctcca gatccttcgc tgctgaaaca gttcccgttc caggctcatt   6780
gcgaaggcct cccggacgga taatcgtata ggttaaaccg ctcgcttcca gaattttatc   6840
agcataatgc ttggccacat aataaggctt gagtgcctca ttccaatttt cacggttatg   6900
ggcttgcagg gcgctgacca taataaaccg tttgattccg gcaatggccg cagcttcaat   6960 ggctttgcc gctccatcaa gatccaccag cagcgtttta tcatagcctg tgctgccgcc   7020
ggaaccggct gtgaaaatga tcgcgtcaca acctttgcc gcagcggcga tttcttccgg   7080
gctgccctcc agattcgcaa gcacagcttc tgcaccggca gcttcaagag acgctttctg   7140
ttcttctttt ctgaccatcg ctctgatgga atgatcagga ttatcttgga ataaagagac   7200
gagtctttgc ccgatttgtc cgttcgctcc gattaaaaac actttcatgt gaatccctcc   7260
```

-continued

```
tgcctccatt atttcaaaaa cacaaccgct ctttcaaacg atgtgttttg ccttagtaaa     7320
tcagatcaag gaaa                                                       7334

<210> SEQ ID NO 49
<211> LENGTH: 25
<212> TYPE: DNA
<213> ORGANISM: artificial sequence
<220> FEATURE:
<223> OTHER INFORMATION: synthesized sequence

<400> SEQUENCE: 49
gaagctgaat gagatttctt aaggc                                                 25

<210> SEQ ID NO 50
<211> LENGTH: 23
<212> TYPE: DNA
<213> ORGANISM: artificial sequence
<220> FEATURE:
<223> OTHER INFORMATION: synthesized sequence

<400> SEQUENCE: 50
aaggaggctt atttccgctt ttc                                                   23
```